United States Patent
Okada et al.

(10) Patent No.: US 11,786,194 B2
(45) Date of Patent: Oct. 17, 2023

(54) RADIATION DETECTOR COMPRISING A REINFORCEMENT SUBSTRATE, RADIOGRAPHIC IMAGING DEVICE, AND MANUFACTURING METHOD

(71) Applicant: FUJIFILM Corporation, Tokyo (JP)

(72) Inventors: Yoshihiro Okada, Kanagawa (JP); Keiichi Akamatsu, Kanagawa (JP); Shinichi Ushikura, Kanagawa (JP); Munetaka Kato, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 133 days.

(21) Appl. No.: 17/025,566

(22) Filed: Sep. 18, 2020

(65) Prior Publication Data

US 2021/0096271 A1    Apr. 1, 2021

Related U.S. Application Data

(63) Continuation of application No. PCT/JP2019/009427, filed on Mar. 8, 2019.

(30) Foreign Application Priority Data

Mar. 19, 2018 (JP) .................................. 2018-051690
Jun. 22, 2018 (JP) .................................. 2018-119356
(Continued)

(51) Int. Cl.
   *A61B 6/00*   (2006.01)
   *G01T 1/20*   (2006.01)
   *G01T 1/161*  (2006.01)

(52) U.S. Cl.
   CPC .......... *A61B 6/4233* (2013.01); *A61B 6/4208* (2013.01); *A61B 6/4283* (2013.01);
   (Continued)

(58) Field of Classification Search
   CPC ....... A61B 6/42; A61B 6/4208; A61B 6/4233; A61B 6/54; A61B 6/542; A61B 6/545;
   (Continued)

(56) References Cited

U.S. PATENT DOCUMENTS 8,946,634 B2 * 2/2015 Watano ..................... G01T 1/16
                                                    250/370.15
9,140,809 B2 * 9/2015 Nakahashi ............. A61B 6/102
(Continued)

FOREIGN PATENT DOCUMENTS

EP    3067332 A1    9/2016
JP    2004-179266 A  6/2004
(Continued)

OTHER PUBLICATIONS

An English Translation of JP2012108158A by Patent Translate. (Year: 2022).*
(Continued)

*Primary Examiner* — Allen C. Ho
(74) *Attorney, Agent, or Firm* — Studebaker & Brackett PC

(57) ABSTRACT

A radiation detector including: a substrate formed with plural pixels that accumulate electrical charges generated in response to light converted from radiation in a pixel region at an opposite-side surface of a base member to a surface including a fine particle layer; the base member being flexible and is made of resin and that includes a fine particle layer containing inorganic fine particles having a mean particle size of from 0.05 μm to 2.5 μm, a conversion layer provided at the surface of the base member provided with the pixel region and configured to convert the radiation into light; and a reinforcement substrate provided to at least one out of a surface on the substrate side of a stacked body configured by stacking the substrate and the conversion
(Continued)

layer, or a surface on the conversion layer side of the stacked body.

20 Claims, 60 Drawing Sheets

(30) Foreign Application Priority Data

| Nov. 22, 2018 | (JP) | ................................ | 2018-219696 |
| Nov. 22, 2018 | (JP) | ................................ | 2018-219699 |
| Feb. 8, 2019 | (JP) | ................................ | 2019-022126 |
| Feb. 8, 2019 | (JP) | ................................ | 2019-022148 |

(52) U.S. Cl.
CPC ............... *A61B 6/54* (2013.01); *G01T 1/161* (2013.01); *G01T 1/20* (2013.01); *G01T 1/2002* (2013.01); *G01T 1/2006* (2013.01); *G01T 1/2018* (2013.01); *G01T 1/20183* (2020.05); *G01T 1/20184* (2020.05); *G01T 1/20186* (2020.05); *G01T 1/20188* (2020.05)

(58) Field of Classification Search
CPC ....... A61B 6/4283; G01T 1/20; G01T 1/2002; G01T 1/2006; G01T 1/2018; G01T 1/20183; G01T 1/20184; G01T 1/20188; G01T 1/20182; G01T 1/20185; G01T 1/20186; G01T 1/20187; G01T 1/20181
USPC ..................................... 378/98.8; 250/370.09
See application file for complete search history.

(56) References Cited

U.S. PATENT DOCUMENTS

| 9,269,741 | B2 * | 2/2016 | Furui | .................... G01T 1/2018 |
| 9,442,200 | B2 * | 9/2016 | Watano | ................. G01T 1/2018 |
| 10,132,937 | B2 * | 11/2018 | Tanino | ...................... G01T 1/20 |
| 10,838,082 | B2 * | 11/2020 | Ushikura | ............. H01L 31/102 |
| 11,221,421 | B2 * | 1/2022 | Iwakiri | ............ H01L 27/14663 |
| 11,262,461 | B2 * | 3/2022 | Ushikura | ............ G01T 1/20188 |
| 11,415,715 | B2 * | 8/2022 | Iwakiri | ............... G01T 1/20184 |
| 11,417,440 | B2 * | 8/2022 | Nakatsugawa | ..... G01T 1/20188 |
| 11,428,827 | B2 * | 8/2022 | Ushikura | ............. G01T 1/1612 |
| 11,520,057 | B2 * | 12/2022 | Iwakiri | .................... A61B 6/00 |
| 11,624,716 | B2 * | 4/2023 | Ushikura | .............. G01T 1/2018 378/62 |
| 11,630,221 | B2 * | 4/2023 | Kato | .................. G01T 1/20181 250/366 |
| 11,633,162 | B2 * | 4/2023 | Kato | ..................... G01T 1/2002 378/62 |
| 2012/0256091 | A1 | 10/2012 | Nakahashi | |
| 2013/0154039 | A1 | 6/2013 | Furui et al. | |
| 2013/0264461 | A1 | 10/2013 | Okada et al. | |
| 2015/0060678 | A1 | 3/2015 | Watano | |

FOREIGN PATENT DOCUMENTS

| JP | 2009-025258 A | 2/2009 |
| JP | 2012-047723 A | 3/2012 |
| JP | 2012-108158 A | 6/2012 |
| JP | 2012-128091 A | 7/2012 |
| JP | 2012-189487 A | 10/2012 |
| JP | 2012-220659 A | 11/2012 |
| JP | 2013-217769 A | 10/2013 |
| JP | 2014-081364 A | 5/2014 |
| JP | 2015-045615 A | 3/2015 |

OTHER PUBLICATIONS

An English Translation of JP2012047723A by Patent Translate. (Year: 2022).*
An English translation of JP2012189487A by Patent Translate. (Year: 2023).*
An English translation of JP2012128091A by Patent Translate. (Year: 2023).*
The extended European search report issued by the European Patent Office dated Mar. 31, 2021, which corresponds to European Patent Application No. 19771992.5-1001 and is related to U.S. Appl. No. 17/025,566.
An Office Action mailed by the Japanese Patent Office dated Apr. 13, 2021, which corresponds to Japanese Patent Application No. 2020-508196 and is related to U.S. Appl. No. 17/025,566; with English language tanslation.
International Search Report issued in PCT/JP2019/009427; dated Jun. 4, 2019.
International Preliminary Report On Patentability and Written Opinion issued in PCT/JP2019/009427; dated Sep. 22, 2020.
Office Action issued in JP 2020-508196; mailed by the Japanese Patent Office dated Dec. 1, 2020.
Communication pursuant to Article 94(3) EPC issued by the European Patent Office dated Oct. 27, 2022, which corresponds to European Patent Application No. 19771992.5-1001 and is related to U.S. Appl. No. 17/025,566.
An Office Action issued by Taiwan Intellectual Property Office dated Aug. 1, 2022, which corresponds to Taiwanese Patent Application No. 108108544 and is related to U.S. Appl. No. 17/025,566; with partial English language translation.

* cited by examiner

RADIATION DETECTOR COMPRISING A REINFORCEMENT SUBSTRATE, RADIOGRAPHIC IMAGING DEVICE, AND MANUFACTURING METHOD

CROSS-REFERENCE TO RELATED APPLICATIONS

This application is a continuation application of International Application No. PCT/JP2019/009427, filed on Mar. 8, 2019, which is incorporated herein by reference in its entirety. Further, this application claims priority from Japanese Patent Application No. 2018-051690, filed on Mar. 19, 2018, Japanese Patent Application No. 2018-119356, filed on Jun. 22, 2018, Japanese Patent Application No. 2018-219696, filed on Nov. 22, 2018, Japanese Patent Application No. 2018-219699, filed on Nov. 22, 2018, Japanese Patent Application No. 2019-022148, filed on Feb. 8, 2019, and Japanese Patent Application No. 2019-022126, filed on Feb. 8, 2019, the disclosure of which are incorporated by reference herein.

BACKGROUND

Technical Field

The present invention relates to a radiation detector, a radiographic imaging device, and a manufacturing method.

Related Art

Radiographic imaging devices that perform radiographic imaging for medical diagnostic purposes are known. In such radiographic imaging devices, a radiation detector is employed to generate radiographic images by detecting radiation that has passed through an imaging subject.

Such radiation detectors may include a conversion layer such as a scintillator to convert radiation into light, and a substrate including a pixel region on a base member, the pixel region being provided with plural pixels that accumulate electrical charges generated in response to light converted by the conversion layer. The use of a flexible base member as the base member of the substrate of such a radiation detector is known (for example, see Japanese Patent Application Laid-Open (JP-A) No. 2013-217769). Employing a flexible base member may for example enable a reduction in weight of the radiographic imaging device (radiation detector) or facilitate imaging of the imaging subject.

However, the radiation detector may be handled on its own during processes to manufacture the radiographic imaging device and the like.

In radiographic imaging devices in which the radiation detector and electric circuitry are arranged in a direction intersecting a stacking direction in which the conversion layer and the substrate are stacked, and a bending adjustment member is provided spanning over the entirety of the radiation detector and the electric circuitry, consideration is not given to the radiation detector being handled on its own. In radiographic imaging devices configured as described above, there is therefore a concern regarding breakage of the conversion layer when the radiation detector is handled on its own.

SUMMARY

An object of the present disclosure is to provide a radiation detector, a radiographic imaging device, and a manufacturing method that are better capable of suppressing breakage of a conversion layer when the radiation detector is on its own than in a radiographic imaging device in which a radiation detector and electric circuitry are arranged in a direction intersecting a stacking direction in which a conversion layer and a substrate are stacked and a bending adjustment member is provided spanning over the entirety of the radiation detector and the electric circuitry.

A first aspect of the present disclosure is a radiation detector including: a substrate formed with plural pixels that accumulate electrical charges generated in response to light converted from radiation in a pixel region at an opposite-side surface of a base member to a surface including a fine particle layer; the base member being flexible and is made of resin and that includes a fine particle layer containing inorganic fine particles having a mean particle size of from 0.05 μm to 2.5 μm, a conversion layer provided at the surface of the base member provided with the pixel region and configured to convert the radiation into light; and a reinforcement substrate provided to at least one out of a surface on the substrate side of a stacked body configured by stacking the substrate and the conversion layer, or a surface on the conversion layer side of the stacked body.

A radiation detector of a second aspect of the present disclosure is the radiation detector of the first aspect, wherein the base member has a coefficient of thermal expansion no greater than 20 ppm/K at 300° C. to 400° C.

A radiation detector of a third aspect of the present disclosure is the radiation detector of the first aspect or the radiation detector of the second aspect, wherein the base member satisfies at least one condition out of: having a heat shrinkage ratio in a machine direction at 400° C. and at a thickness of 25 μm of no greater than 0.5%; or having a modulus of elasticity at 500° C. of no less than 1 GPa.

A radiation detector of a fourth aspect of the present disclosure is the radiation detector of any one of the first aspect to the third aspect, wherein the fine particles include an element having an atomic number that is greater than an atomic number of elements configuring the base member and that is an atomic number not exceeding 30.

A radiation detector of a fifth aspect of the present disclosure is the radiation detector of any one of the first aspect to the fourth aspect, wherein the reinforcement substrate has a bending elastic modulus of from 150 MPa to 2500 MPa.

A radiation detector of a sixth aspect of the present disclosure is the radiation detector of any one of the first aspect to the fifth aspect, wherein a ratio of a coefficient of thermal expansion of the reinforcement substrate with respect to a coefficient of thermal expansion of the conversion layer is from 0.5 to 2.

A radiation detector of a seventh aspect of the present disclosure is the radiation detector of any one of the first aspect to the sixth aspect, wherein the reinforcement substrate has a coefficient of thermal expansion of from 30 ppm/K to 80 ppm/K.

A radiation detector of an eighth aspect of the present disclosure is the radiation detector of any one of the first aspect to the seventh aspect, wherein the reinforcement substrate contains a material having a yield point.

A radiation detector of a ninth aspect of the present disclosure is the radiation detector of any one of the first aspect to the eighth aspect, wherein the reinforcement substrate has a higher rigidity than the base member.

A radiation detector of a tenth aspect of the present disclosure is the radiation detector of any one of the first aspect to the ninth aspect, wherein a thickness of the reinforcement substrate is thicker than a thickness of the base member.

A radiation detector of an eleventh aspect of the present disclosure is the radiation detector of any one of the first aspect to the tenth aspect, wherein: the conversion layer covers the pixel region and is provided in a region corresponding to part of the surface of the base member provided with the pixel region; and the reinforcement substrate is provided in a wider region than the region where the conversion layer is provided.

A radiation detector of a twelfth aspect of the present disclosure is the radiation detector of any one of the first aspect to the eleventh aspect, wherein: the reinforcement substrate is provided at the substrate-side surface of the stacked body configured by stacking the substrate and the conversion layer, and at the conversion layer-side surface of the stacked body; and a thickness of the reinforcement substrate provided at the conversion layer-side surface is thicker than a thickness of the reinforcement substrate provided on the substrate-side surface.

A radiation detector of a thirteenth aspect of the present disclosure is the radiation detector of any one of the first aspect to the twelfth aspect, wherein the reinforcement substrate is a substrate employing plastic as a material.

A radiation detector of a fourteenth aspect of the present disclosure is the radiation detector of the thirteenth aspect, wherein the plastic is at least one out of polycarbonate or polyethylene terephthalate.

A radiation detector of a fifteenth aspect of the present disclosure is the radiation detector of the thirteenth aspect or the fourteenth aspect, wherein the plastic is at least one out of a styrene, acrylic, polyacetal, or Nylon plastic.

A radiation detector of a sixteenth aspect of the present disclosure is the radiation detector of any one of the thirteenth aspect to the fifteenth aspect, wherein the plastic is at least one out of a polypropylene, ABS, engineering plastic, polyethylene terephthalate, or polyphenylene ether plastic.

A radiation detector of a seventeenth aspect of the present disclosure is the radiation detector of the thirteenth aspect, wherein the plastic is a thermoplastic resin.

A radiation detector of an eighteenth aspect of the present disclosure is the radiation detector of any one of the first aspect to the seventeenth aspect, further including a buffer layer provided between the substrate and the conversion layer, the buffer layer buffers a difference between a coefficient of thermal expansion of the conversion layer and a coefficient of thermal expansion of the substrate.

A radiation detector of a nineteenth aspect of the present disclosure is the radiation detector of any one of the first aspect to the eighteenth aspect, wherein each of the pixels includes: a sensor section generating an electrical charge according to a radiation amount of irradiated radiation and to accumulate the generated electrical charge; and a switching element that reads the electrical charge accumulated by the sensor section.

A radiation detector of a twentieth aspect of the present disclosure is the radiation detector of any one of the first aspect to the nineteenth aspect, wherein: the switching element is a transistor including a gate electrode; and the substrate is provided with a layer configured by an inorganic material between the base member and the gate electrode.

A radiation detector of a twenty-first aspect of the present disclosure is the radiation detector of any one of the first aspect to the twentieth aspect, wherein: the reinforcement substrate is provided at the substrate-side surface of the stacked body stacked with the conversion layer; and a sealing member is further provided between the reinforcement substrate and the conversion layer-side surface of the substrate so as to seal a side face of the conversion layer.

A radiation detector of a twenty-second aspect of the present disclosure is the radiation detector of any one of the first aspect to the twenty-first aspect, wherein: the stacked body further includes a location on the conversion layer side where a reflective adhesion layer for reflecting light converted by the conversion layer, a bonding layer covering a region including a region spanning from an end portion of the adhesion layer to a front surface of the substrate, and a protective layer covering the adhesion layer and the bonding layer are stacked in this sequence; and the reinforcement substrate is provided to at least one out of the substrate-side surface of the stacked body or a surface on the protective layer side of the stacked body.

A radiation detector of a twenty-third aspect of the present disclosure is the radiation detector of any one of the first aspect to the twenty-first aspect, wherein: the stacked body further includes a location on the conversion layer side where a reflective adhesion layer for reflecting light converted by the conversion layer and covering a region including a region including the entire conversion layer and spanning a front surface of the substrate, and a protective layer covering the adhesion layer are stacked in this sequence; and the reinforcement substrate is provided to at least one out of the substrate-side surface of the stacked body or a surface on the protective layer side of the stacked body.

A radiation detector of a twenty-fourth aspect of the present disclosure is the radiation detector of any one of the first aspect to the twenty-third aspect, wherein the conversion layer includes columnar crystals of CsI.

A radiographic imaging device of a twenty-fifth aspect of the present disclosure includes the radiation detector of any one of the first aspect to the twenty-fourth aspect, a control section that outputs a control signal for reading the electrical charges accumulated in the plural pixels; a drive section that reads the electrical charges from the plural pixels in response to the control signal; and a signal processing section that is input with an electrical signal according to the electrical charges read from the plural pixels, and that generates image data according to the input electrical signal and output the image data to the control section.

A radiographic imaging device of a twenty-sixth aspect of the present disclosure is the radiographic imaging device of the twenty-fifth aspect, further including a case that includes an irradiated face for irradiation with radiation, and that houses the radiation detector in a state in which out of the sensor substrate and the conversion layer of the radiation detector it is the sensor substrate that opposes the irradiated face.

A twenty-seventh aspect of the present disclosure is a manufacturing method for a radiation detector, the manufacturing method including: a process of coating an adhesion layer onto a reinforcement substrate having a size according to the size of a radiation detector; a process of forming a substrate on a support body with a separation layer interposed between the support body and the substrate, the substrate being provided with a base member that is flexible and made of resin and that is provided with a fine particle layer including inorganic fine particles having a mean particle size of from 0.05 µm to 2.5 µm, and provided with a plural pixels configured to accumulate electrical charge generated in response to light converted from radiation in a pixel region on an opposite-side surface of the base member to a surface including the fine particle layer; a process of forming a conversion layer configured to convert the radiation into light on the surface of the base member provided with the pixel region; a process of connecting wiring to the substrate in order to connect the pixels to a circuit section; a process of affixing the reinforcement substrate to an opposite-side surface of the conversion layer to a surface opposing the substrate; and a process of separating the substrate provided with the conversion layer and the reinforcement substrate and to which the wiring is connected from the support body.

The present disclosure may suppress breakage of the conversion layer when the radiation detector is on its own, than in a radiographic imaging device in which the radiation detector and electric circuitry are arranged in a direction intersecting a stacking direction in which a conversion layer and a substrate are stacked and a bending adjustment member is provided spanning over the entirety of the radiation detector and the electric circuitry.

DESCRIPTION OF EMBODIMENTS

Detailed explanation follows regarding exemplary embodiments of the present invention, with reference to the drawings. Note that the present invention is not limited to these exemplary embodiments.

First Exemplary Embodiment

A radiation detector 10 of the present exemplary embodiment has a function of outputting image information expressing radiographic images of an imaging subject by detecting radiation that has passed through the imaging subject. The radiation detector 10 of the present exemplary embodiment includes a thin film transistor (TFT) substrate 12 and a conversion layer 14 configured to convert radiation into light (a TFT substrate 12 and a conversion layer 14 of a radiation detector 10, see FIG. 4).

Figure 1:
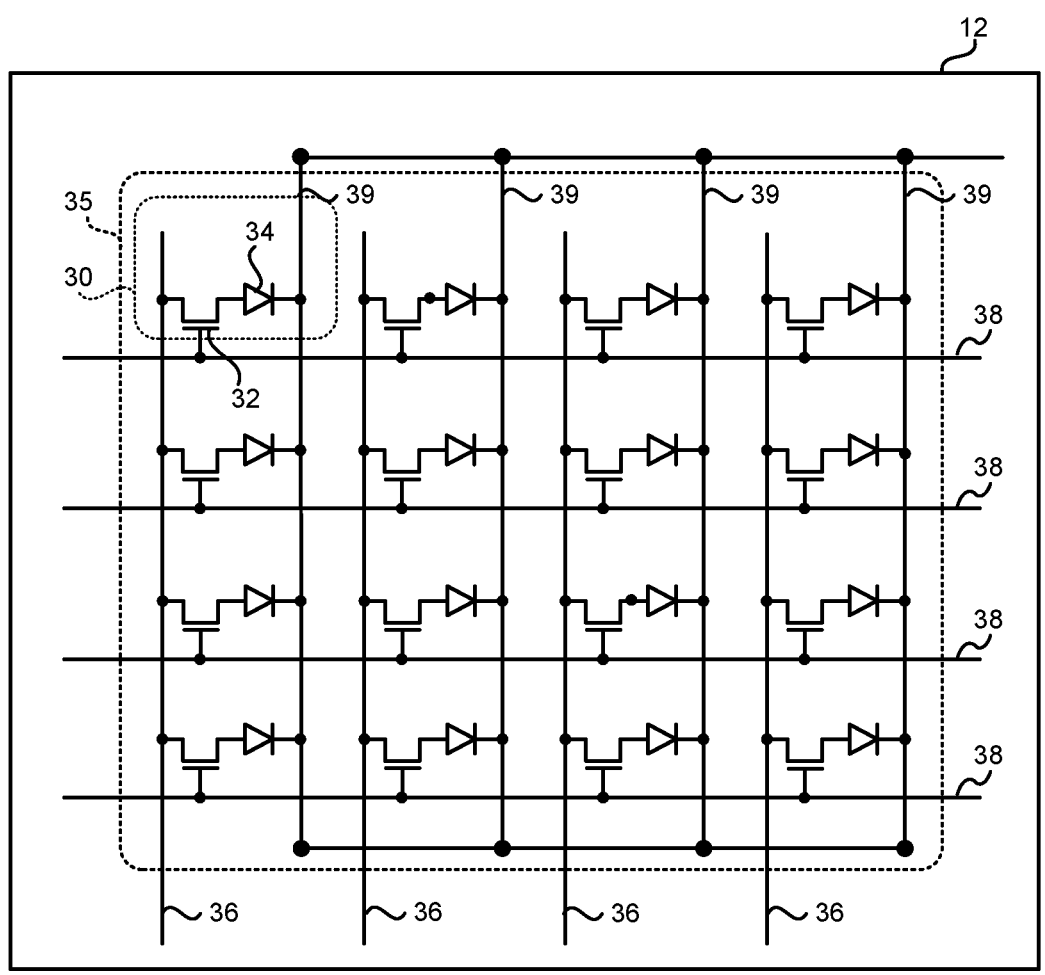
FIG. 1 is a configuration diagram illustrating an example of configuration of a thin film transistor (TFT) substrate of a radiation detector of a first exemplary embodiment.

First, explanation follows regarding an example of configuration of the TFT substrate 12 of the radiation detector of the present exemplary embodiment, with reference to FIG. 1. Note that the TFT substrate 12 of the present exemplary embodiment is a substrate in which a pixel array 31 including plural pixels 30 is formed in a pixel region 35 of a base member 11. Accordingly, the expression "pixel region 35" is synonymous with the "pixel array 31". The TFT substrate 12 of the present exemplary embodiment is an example of a substrate of technology disclosed herein.

The base member 11 is made of resin, and is flexible. For example, the base member 11 is a resin sheet including a plastic such as polyimide. The thickness of the base member 11 may be any thickness that enables the desired flexibility to be obtained, set according to the hardness of the material, the size of the TFT substrate 12, and the like. For example, in cases in which the base member 11 is configured by a resin sheet, the base member 11 should have a thickness of from 5 µm to 125 µm, and more preferably has a thickness of from 20 µm to 50 µm.

Note that the base member 11 has characteristics capable of withstanding manufacture of the pixels 30, as will be described in detail later, and in the present exemplary embodiment, has characteristics capable of withstanding the manufacture of amorphous silicon TFTs (a-Si TFTs). Preferable characteristics of the base member 11 are a coefficient of thermal expansion in a temperature range from 300° C. to 400° C. that is similar to that of an amorphous silicon (Si) wafer (for example ±5 ppm/K), and more specifically preferably no greater than 20 ppm/K. The heat shrinkage ratio of the base member 11 in a machine direction (MD) at 400° C. and at a thickness of 25 µm is preferably a heat shrinkage ratio of no greater than 0.5%. Moreover, the modulus of elasticity of the base member 11 preferably does not have a transition point in a temperature region of from 300° C. to 400° C., as is typical of an ordinary polyimide, and preferably has a modulus of elasticity at 500° C. of no less than 1 GPa.

Figure 2A:
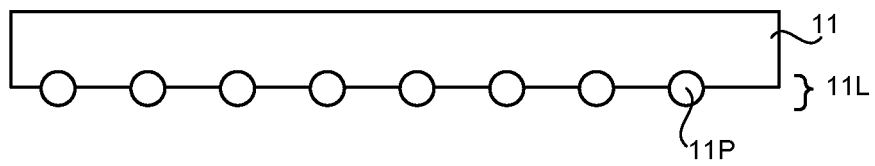
FIG. 2A is a cross-section to explain an example of a base member of an exemplary embodiment.
Figure 2B:
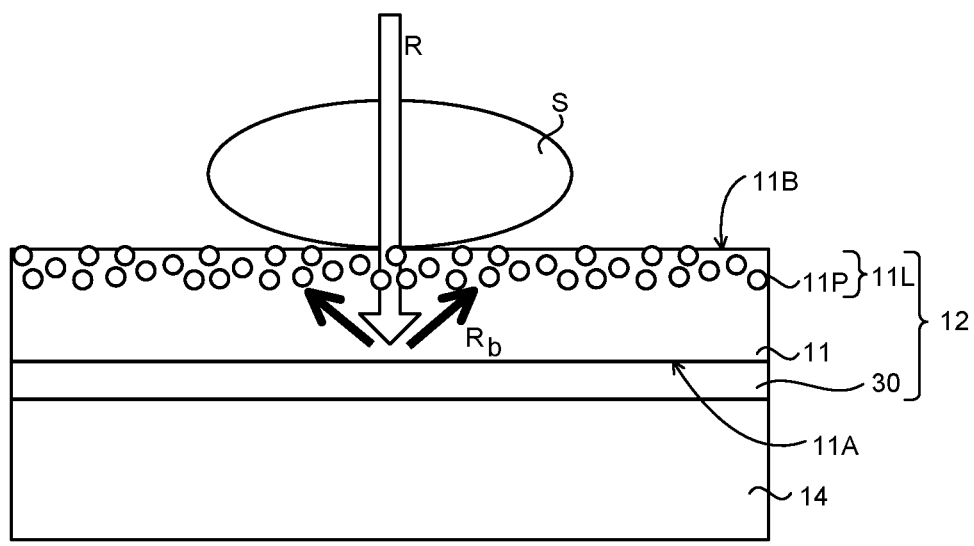
FIG. 2B is an explanatory diagram to explain back-scattered radiation generated within a base member including a fine particle layer by radiation that has passed through an imaging subject.

Moreover, as illustrated in FIG. 2A and FIG. 2B, the base member 11 of the present exemplary embodiment preferably includes a fine particle layer 11L containing inorganic fine particles 11P having a mean particle size of from 0.05 μm to 2.5 μm on an opposite-side surface to the side provided with the conversion layer 14.

Figure 2C:
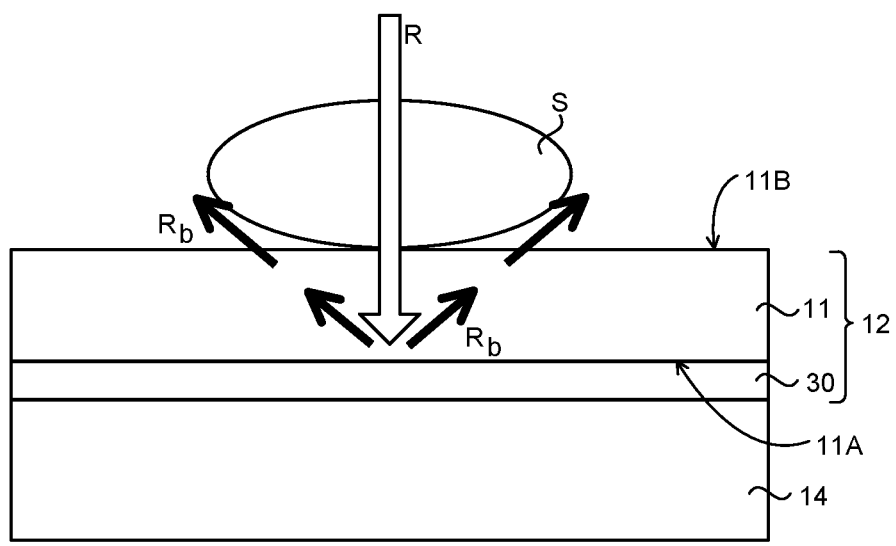
FIG. 2C is an explanatory diagram to explain back-scattered radiation generated within a base member not including a fine particle layer by radiation that has passed through an imaging subject.

Note that FIG. 2B and FIG. 2C illustrate examples of cases in which the radiation detector 10 of the present exemplary embodiment is applied as a radiation detector employing an irradiation side sampling (ISS) approach in which radiation R is irradiated from the TFT substrate 12 side.

As illustrated in FIG. 2B and FIG. 2C, the radiation R that has passed through an imaging subject S causes back-scattered radiation Rb in the base member 11. In cases in which the base member 11 is configured from a resin such as a PI, this being an organic material, the back-scattered radiation Rb of atoms of C, H, O, N and the like configuring the organic material and that have comparatively small atomic numbers increases due to the Compton effect.

As illustrated in FIG. 2B, in cases in which the base member 11 includes the fine particle layer 11L containing the fine particles 11P to absorb the back-scattered radiation Rb generated within the base member 11, then the back-scattered radiation Rb is suppressed from passing through the base member 11 and being scattered at the back of the base member 11 in comparison to cases in which the base member 11 does not include the fine particle layer 11L as illustrated in FIG. 2D. The inclusion of the fine particle layer 11L is thus preferable.

The fine particles 11P are preferably configured by an inorganic material containing atoms that cause little back-scattered radiation Rb in their own right, that absorb the back-scattered radiation Rb, and that absorb little of the radiation R that has passed through the imaging subject S. Note that there is a trade-off relationship between suppressing back-scattered radiation Rb and allowing the radiation R to pass through. From the perspective of suppressing the back-scattered radiation Rb, the fine particles 11P preferably include elements having atomic numbers greater than those of the C, H, O, N, and the like configuring the resin of the base member 11. Although the ability to absorb the back-scattered radiation Rb increases the greater the atomic number, if the atomic number exceeds 30, the amount of radiation R absorbed increases, and there is a marked decrease in the amount of radiation R that reaches the conversion layer 14, and so this is not preferable. Accordingly, in cases in which the base member 11 is made of resin, an inorganic material that has an atomic number greater than the atoms configuring the organic material that is the base member 11, but does not exceed 30, is preferably employed as the fine particles 11P. Specific examples of such fine particles 11P include $SiO_2$ that is an oxide of silicon having the atomic number 14, MgO that is an oxide of Mg having the atomic number 12, $Al_2O_3$ that is an oxide of Al having the atomic number 13, and $TiO_2$ that is an oxide of Ti having the atomic number 22.

XENOMAX (registered trademark) is a specific example of a resin sheet having the characteristics listed above.

Note that the thickness discussed in the present exemplary embodiment is measured using a micrometer. The coefficient of thermal expansion is measured according to JIS K7197: 1991. In this measurement, test pieces are cut from a main face of the base member 11 while changing the angle thereof by 15 degrees each time, the coefficient of thermal expansion is measured for each of the cut test pieces, and the highest value obtained is taken to be the coefficient of thermal expansion of the base member 11. The measurements of the coefficient of thermal expansion in the machine direction (MD) and a transverse direction (TD) are performed at 10° C. intervals over a range of from −50° C. to 450° C. with ppm/° C. converted into ppm/K. A TMA4000S instrument made by MAC Science Co., Ltd. is employed to measure the coefficient of thermal expansion using a sample length of 10 mm, a sample width of 2 mm, an initial load of 34.5 g/mm², a rate of temperature increase of 5° C./min, and an argon atmosphere. The modulus of elasticity is measured according to JIS K7171:2016. Note that in this measurement, test pieces are cut from a main face of the base member 11 while changing the angle thereof by 15 degrees each time, a stretch test is performed on each of the cut test pieces, and the highest value obtained is taken to be the modulus of elasticity of the base member 11.

Note that unevenness may arise on the front surface of the base member 11 due to the fine particles 11P contained in the fine particle layer 11L. Formation of the pixels 30 sometimes becomes difficult in a state in which such unevenness has arisen on the front surface of the base member 11. Accordingly, as illustrated in FIG. 2B, the fine particle layer 11L is preferably included on a second surface 11B on the opposite side of the base member 11 to a first surface 11A on which the pixels 30 are formed, namely on the second surface 11B on the opposite side to the first surface 11A provided with the conversion layer 14.

In order to sufficiently absorb the back-scattered radiation Rb generated within the base member 11, the fine particle layer 11L is preferably included on the surface of the base member 11 on the side that is closer to the imaging subject S. As illustrated in FIG. 2B, in the ISS-approach radiation detector 10, the fine particle layer 11L, is preferably included on the second surface 11B.

Thus, in the ISS-approach radiation detector 10, the base member 11 includes the fine particle layer 11L on the second surface 11B, enabling the pixels 30 to be formed with good precision, and also enabling back-scattered radiation Rb to be effectively suppressed.

Each of the pixels 30 includes a sensor section 34 that accumulates an electrical charge generated in response to light converted by the conversion layer, and a switching element 32 that reads the accumulated electrical charge from the sensor section 34. As an example, in the present exemplary embodiment, a thin film transistor (TFT) is employed as the switching element 32. The switching element 32 is thus referred to as the "TFT 32" hereafter.

The plural pixels 30 are arranged along one direction (a scan line direction corresponding to the lateral direction in FIG. 1, hereafter also referred to as the "row direction") and along a direction intersecting the row direction (a signal line direction corresponding to the longitudinal direction in FIG. 1, hereafter also referred to as the "column direction") to form a two-dimensional pattern in the pixel region 35 of the TFT substrate 12. Although the array of the pixels 30 is simplified in the illustration of FIG. 1, for example 1024× 1024 of the pixels 30 are arranged along the row direction and the column direction.

The radiation detector 10 is further provided with plural scan lines 38 to control switching states (ON and OFF states) of the TFTs 32, and plural signal lines 36 that intersect the plural scan lines 38 and correspond to each column of the pixels 30 to read the accumulated electrical charges from the sensor sections 34. Each of the plural scan lines 38 is connected to a drive section (a drive section 103, see FIG. 18 and FIG. 19) provided externally to the radiation detector 10 through a pad (not illustrated in the drawings) provided on the TFT substrate 12, so as to allow a flow of control signals output from the drive section to control the switching states of the TFTs 32. Moreover, each of the plural signal lines 36 is connected to a signal processing section (a signal processing section 104, see FIG. 19 and FIG. 19) provided externally to the radiation detector 10 through a pad (not illustrated in the drawings) provided on the TFT substrate 12, such that electrical charges read from the pixels 30 are output to the signal processing section.

Common lines 39 are provided along the wiring direction of the signal lines 36 to the sensor sections 34 of the corresponding pixels 30 in order to apply a bias voltage to the corresponding pixels 30. Each of the common lines 39 is connected to a bias power source provided externally to the radiation detector 10 through a pad (not illustrated in the drawings) provided on the TFT substrate 12, such that the bias voltage from the bias power source is applied to the corresponding pixels 30.

Figure 3:
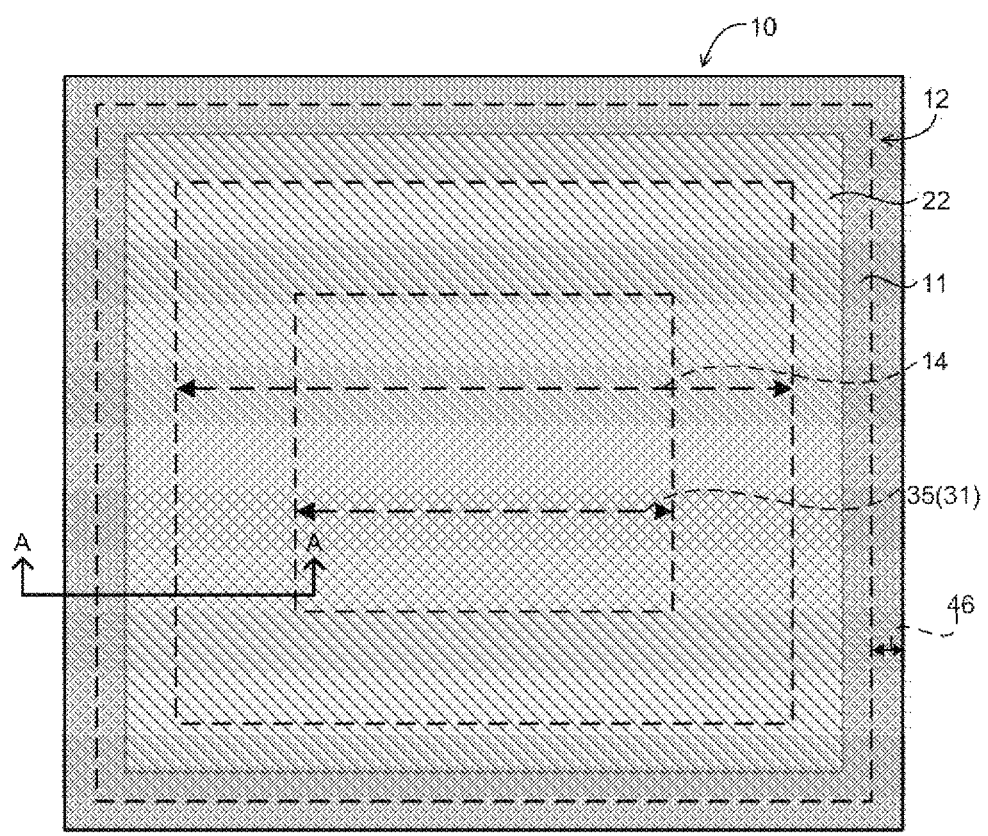
FIG. 3 is a plan view illustrating an example of a radiation detector of the first exemplary embodiment as viewed from a side provided with a conversion layer.
Figure 4:
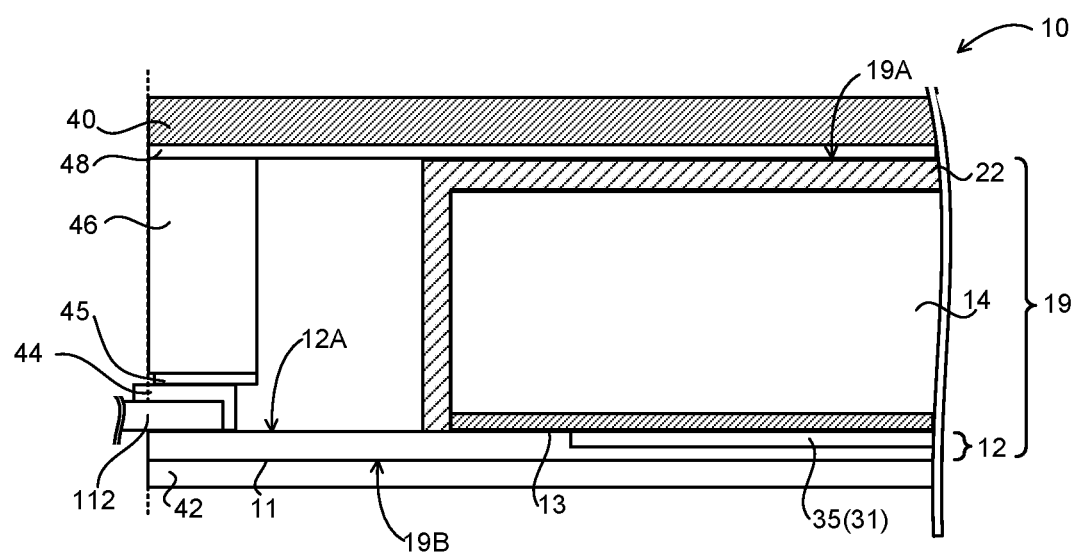
FIG. 4 is a cross-section of the radiation detector illustrated in FIG. 3, as sectioned along line A-A.

In the radiation detector 10 of the present exemplary embodiment, the conversion layer is formed on top of the TFT substrate 12. FIG. 3 is a plan view illustrating the radiation detector 10 of the present exemplary embodiment as viewed from a side formed with the conversion layer 14. FIG. 4 is a cross-section of the radiation detector 10 illustrated in FIG. 3, as sectioned along line A-A. In the following explanation, reference to "on top" with respect to the structure of the radiation detector 10 refers being on top in a positional relationship referenced against the TFT substrate 12 side.

As illustrated in FIG. 3 and FIG. 4, the conversion layer 14 of the present exemplary embodiment is provided on top of a region configuring a portion of the first surface 12A of the TFT substrate 12 that includes the pixel region 35. Thus, the conversion layer 14 of the present exemplary embodiment is not provided on top of a region corresponding to an outer peripheral portion of the first surface 12A of the TFT substrate 12.

In the present exemplary embodiment, a scintillator containing cesium iodide (CsI) is employed as an example of the conversion layer 14. For example, the scintillator preferably contains thallium-doped cesium iodide (CsI:Tl) or sodium-doped cesium iodide (CsI:Na) that has light emission spectra of from 400 nm to 700 nm when irradiated with X-rays. Note that the peak light emission wavelength of CsI:Tl in the visible light region is 565 nm.

As in the example illustrated in FIG. 4, in the radiation detector 10 of the present exemplary embodiment, the conversion layer 14 is formed from strip shaped columnar crystals 14A (see FIG. 9) formed directly on top of the TFT substrate 12 using a vapor phase deposition method such as a vacuum deposition method, a sputtering method, or a chemical vapor deposition (CVD) method. As an example of the formation method of the conversion layer 14, in cases in which CsI:Tl is used as the conversion layer 14, a vacuum deposition method may be applied in which the CsI:Tl is heated and vaporized, for example using a resistance heating crucible under environmental conditions of a vacuum of from 0.01 Pa to 10 Pa, and the CsI:Tl is deposited on top of the TFT substrate 12 with the TFT substrate 12 at a temperature between room temperature (20° C.) and 300° C. The thickness of the conversion layer 14 is preferably from 100 μm to 800 μm.

Note that in the present exemplary embodiment, end portions on a growth direction base side of the columnar crystals 14A (see FIG. 9) of the conversion layer 14 (on the TFT substrate 12 side in the present exemplary embodiment) are referred to as the base, and peaked end portions on the opposite side to the base in the growth direction are referred to as the tips. In the present exemplary embodiment, as illustrated in FIG. 4, for example, a buffer layer 13 is provided between the TFT substrate 12 and the conversion layer 14. A polyimide (PI) film or a Parylene (registered trademark) film may be employed as the buffer layer 13.

A protective layer 22 of the present exemplary embodiment has a function of protecting the conversion layer 14 from moisture such as humidity. Examples of materials that may be employed as the material of the protective layer 22 include organic films such as single layer films or stacked films of polyethylene terephthalate (PET), polyphenylene sulfide (PPS), oriented polypropylene (OPP), polyethylene naphthalate (PEN), PI, and the like. Moreover, an ALPET (registered trademark) sheet in which aluminum is stacked by for example bonding aluminum foil to an insulating sheet (film) such as PET may be employed as the protective layer 22.

A stacked body 19 configured by stacking the TFT substrate 12, the buffer layer 13, the conversion layer 14, and the protective layer 22 includes a first surface 19A, this being a surface on the conversion layer 14 side. A reinforcement substrate 40 is provided on the first surface 19A using an adhesion layer 48 or the like.

The reinforcement substrate 40 has a higher rigidity than the base member 11, such that dimensional change (deformation) with respect to force applied in a direction perpendicular to a surface opposing the first surface 19A is smaller than the dimensional change of the base member 11 with respect to force applied in a direction perpendicular to the first surface 19A. The thickness of the reinforcement substrate 40 of the present exemplary embodiment is also thicker than the thickness of the base member 11.

More specifically, the reinforcement substrate 40 of the present exemplary embodiment preferably employs a material having a bending elastic modulus of from 150 MPa to 2500 MPa. The bending elastic modulus is, for example, measured according to the method set out in JIS K7171: 2016. The reinforcement substrate 40 preferably has a higher bending rigidity than the base member 11 from the perspective of suppressing bending of the base member 11. Note that since the bending rigidity decreases as the bending elastic modulus decreases, the thickness of the reinforcement substrate 40 has to be increased in order to obtain the desired bending rigidity, causing an increase in the overall thickness of the radiation detector 10. Considering the materials of the reinforcement substrate 40 described above, the thickness of the reinforcement substrate 40 tends to become comparatively large when attempting to obtain a bending rigidity in excess of 140,000 Pa·cm$^4$. Accordingly, in consideration of both obtaining an appropriate rigidity and the overall thickness of the radiation detector 10, the material employed for the reinforcement substrate 40 preferably has a bending elastic modulus of from 150 MPa to 2500 MPa. The bending rigidity of the reinforcement substrate 40 is preferably from 540 Pa·cm$^4$ to 140,000 Pa·cm$^4$.

The coefficient of thermal expansion of the reinforcement substrate 40 of the present exemplary embodiment is preferably close to the coefficient of thermal expansion of the material of the conversion layer 14, and more preferably the ratio of the coefficient of thermal expansion of the reinforcement substrate 40 with respect to the coefficient of thermal expansion of the conversion layer 14 (the coefficient of thermal expansion of the reinforcement substrate 40 divided by the coefficient of thermal expansion of the conversion layer 14) is from 0.5 to 2. The coefficient of thermal expansion of the reinforcement substrate 40 is preferably from 30 ppm/K to 80 ppm/K. For example, in cases in which CsI:Tl is employed as the material of the conversion layer 14, the coefficient of thermal expansion thereof is 50 ppm/K. In such cases, examples of materials comparatively close to that of the conversion layer 14 include polyvinyl chloride (PVC) with a coefficient of thermal expansion of from 60 ppm/K to 80 ppm/K, acrylic with a coefficient of thermal expansion of from 70 ppm/K to 80 ppm/K, PET with a coefficient of thermal expansion of from 65 ppm/K to 70 ppm/K, PC with a coefficient of thermal expansion of 65 ppm/K, and TEFLON (registered trademark) with a coefficient of thermal expansion of from 45 ppm/K to 70 ppm/K.

In consideration of the bending elastic modulus mentioned above, the material of the reinforcement substrate 40 preferably contains at least one material out of PET, PC, or LDPE.

From the perspective of elasticity, the reinforcement substrate 40 preferably contains a material having a yield point. In the present exemplary embodiment, the "yield point" refers to the point at which stress does not increase but strain does increase on a curve expressing the relationship between stress and strain in the phenomenon in which stress suddenly decreases when the material is applied with tension, and is the apex of the stress-strain curve when the material is tested for tensile strength. Examples of resins having a yield point are generally hard resins with high viscosity, and soft resins with high viscosity and moderate strength. PC is an example of a hard resin with high viscosity. Polypropylene is an example of a soft resin with high toughness and moderate strength.

A plastic is employed as the material of the substrate configuring the reinforcement substrate 40 of the present exemplary embodiment. The plastic employed as the material of the reinforcement substrate 40 is preferably a thermoplastic resin for the above reasons, and examples thereof include at least one out of a polycarbonate (PC), PET, styrene, acrylic, polyacetal, Nylon, polypropylene, acrylonitrile butadiene styrene (ABS), engineering plastic, PET, or polyphenylene ether plastic. Note that of the above, the reinforcement substrate 40 is preferably configured from at least one out of a polypropylene, ABS, engineering plastic, PET, or polyphenylene ether plastic. The reinforcement substrate 40 is more preferably configured from at least one out of a styrene, acrylic, polyacetal, or Nylon plastic, and is more preferably configured from at least one out of PC or PET.

As illustrated in FIG. 3 and FIG. 4, the reinforcement substrate 40 of the present exemplary embodiment is provided over a wider region of the first surface 12A of the TFT substrate 12 than the region provided with the conversion layer 14. Thus, as illustrated in FIG. 3 and FIG. 4, an end portion of the reinforcement substrate 40 projects out further toward an outer side (an outer peripheral portion side of the TFT substrate 12) than an outer peripheral portion of the conversion layer 14.

A flexible cable 112, described in detail later, is connected to the outer peripheral portion of the TFT substrate 12. The flexible cable 112, an anti-moisture agent 44, and an adhesion layer 45 are sandwiched between the reinforcement substrate 40 and the first surface 12A of the TFT substrate 12, and a spacer 46 is provided to seal a side face of the conversion layer 14. The spacer 46 of the present exemplary embodiment is an example of a sealing member of the present disclosure.

The method of providing the spacer 46 is not particularly limited, and for example the spacer 46 may be affixed to the adhesion layer 48 at an end portion of the reinforcement substrate 40, and the reinforcement substrate 40 may then be affixed to the TFT substrate 12 in a state in which the spacer 46 has been provided to the reinforcement substrate 40 and in a state in which the stacked body 19, the flexible cable 112, the anti-moisture agent 44, and the adhesion layer 45 have been provided to the TFT substrate 12, such that the spacer 46 is thus provided between the TFT substrate 12 and the reinforcement substrate 40. Note that the width of the spacer 46 (in a direction intersecting the stacking direction of the stacked body 19) is not limited to the example illustrated in FIG. 4. For example, the width of the spacer 46 may be increased to a position closer to the conversion layer 14 than that illustrated in the example of FIG. 4.

A protective film 42 that has a function of protecting from moisture such as humidity is provided on a second surface 19B, this being a surface on the TFT substrate 12 side of the stacked body 19 of the present exemplary embodiment. Materials configuring the protective film 42 may, for example, be the same as the materials employed for the protective layer 22.

Explanation follows regarding an example of a manufacturing method of the radiation detector 10 of the present exemplary embodiment.

Figure 5:
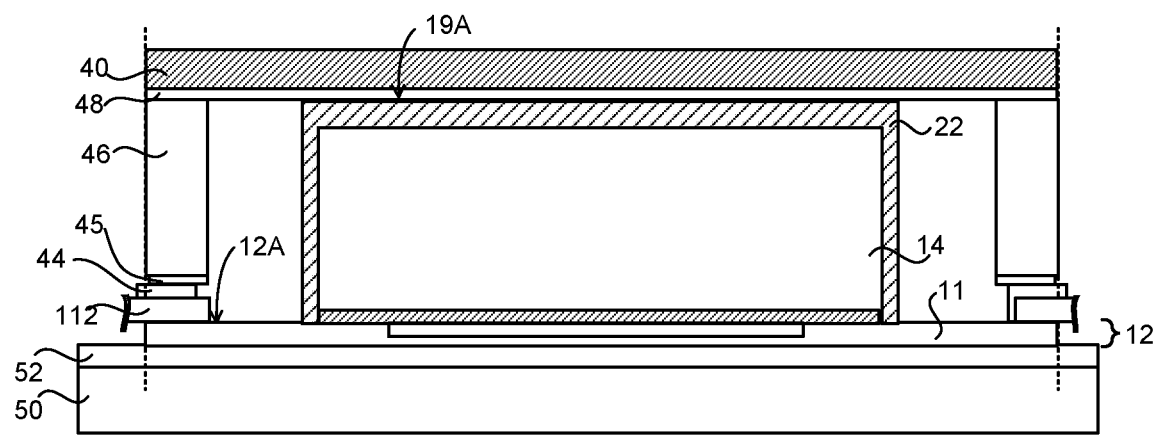
FIG. 5 is an explanatory diagram to explain an example of a manufacturing method of a radiation detector of the first exemplary embodiment.

First, the adhesion layer 48 is coated onto the reinforcement substrate 40 that has been configured at a desired size suited to that of the radiation detector 10 in advance, and the spacer 46 is provided to the adhesion layer 48. As illustrated in FIG. 5, the TFT substrate 12 is formed on a support body 50 such as a glass substrate with a thicker thickness than the base member 11 by a lamination method or the like, with a separation layer 52 interposed therebetween. Then, as described previously, the conversion layer 14 is formed directly on top of the TFT substrate 12 by a vapor phase deposition method, and the flexible cable 112, the anti-moisture agent 44, and the adhesion layer 45 are then provided.

The reinforcement substrate 40 provided with the spacer 46 is then affixed to the TFT substrate 12 on which the conversion layer 14 has been formed, thus sealing the conversion layer 14. Note that this affixing may be performed under atmospheric pressure or under a reduced pressure (in a vacuum). Reduced pressure is preferable in order to suppress air and the like from being incorporated between affixed components.

The TFT substrate 12 is then separated from the support body 50 using the separation layer 52. There is no particular limitation to the separation method. For example, in a mechanical separation method, separation may be started at any of the four edges of the TFT substrate 12 (base member 11) to gradually peel the TFT substrate 12 away from the support body 50 from the start edge toward the edge opposing the start edge. As another example, in a laser separation (laser lift-off) method, the TFT substrate 12 may be separated from the support body 50 by shining a laser onto a back face (an opposite-side surface to the surface provided with the TFT substrate 12) of the support body 50 and breaking down the separation layer 52 with the laser that has passed through the support body 50.

Note that the mechanical separation or laser separation described above is preferably performed after bonding the flexible cable 112 to the TFT substrate 12 by thermal compression or the like. In cases in which the flexible cable 112 is bonded to the TFT substrate 12 after the TFT substrate 12 has been separated from the support body 50, the TFT substrate 12 bends, making the flexible cable 112 more difficult to connect, and more susceptible to positional misalignment. As will be described later, in a radiographic imaging device 1 of the present exemplary embodiment, the drive section 103, the signal processing section 104 (both of which will be described in detail later), and the like are configured using what is referred to as chip-on-film (COF) technology, namely as chips provided on top of the flexible cable 112. Since the chips configuring the drive section 103, the signal processing section 104, and the like are heavy, the TFT substrate 12 readily bends under the weight of the flexible cable 112. In particular, in cases in which plural COF flexible cables 112 are connected to the TFT substrate 12, the weight of previously connected flexible cables 112 causes the TFT substrate 12 to bend, which could make positional misalignment of subsequently connected flexible cables 112 more likely. Accordingly, as described above, the TFT substrate 12 is preferably separated from the support body 50 after connecting the flexible cable 112 to the TFT substrate 12. Note that the flexible cable 112 of the present exemplary embodiment is an example of wiring of the present disclosure, and the drive section 103 and the signal processing section 104 of the present exemplary embodiment are an example of circuit sections of the present disclosure.

Note that when separating the TFT substrate 12 from the support body 50, due to the flexibility of the base member 11, the TFT substrate 12 bends readily. When the TFT substrate 12 bends greatly, there is a concern regarding breakage of the conversion layer 14 as a result of the TFT substrate 12 bending greatly. Moreover, there is a concern regarding breakage of the conversion layer 14 due to bending of the TFT substrate 12 not only when separating the TFT substrate 12 from the support body 50, but also when the radiation detector 10 is handled on its own such as during manufacturing processes of the radiographic imaging device 1. To address this, in the radiation detector 10 of the present exemplary embodiment, the reinforcement substrate 40 is provided to the first surface 19A, this being the surface on the conversion layer 14 side of the stacked body 19. This thereby enables the TFT substrate 12 to be suppressed from bending greatly, enabling breakage of the conversion layer 14 to be suppressed.

Second Exemplary Embodiment

Next, explanation follows regarding a second exemplary embodiment. Note that since a stacked body 19 of a radiation detector 10 of the present exemplary embodiment differs from that of the first exemplary embodiment, the stacked body 19 will be explained with reference to the drawings.

Figure 6:
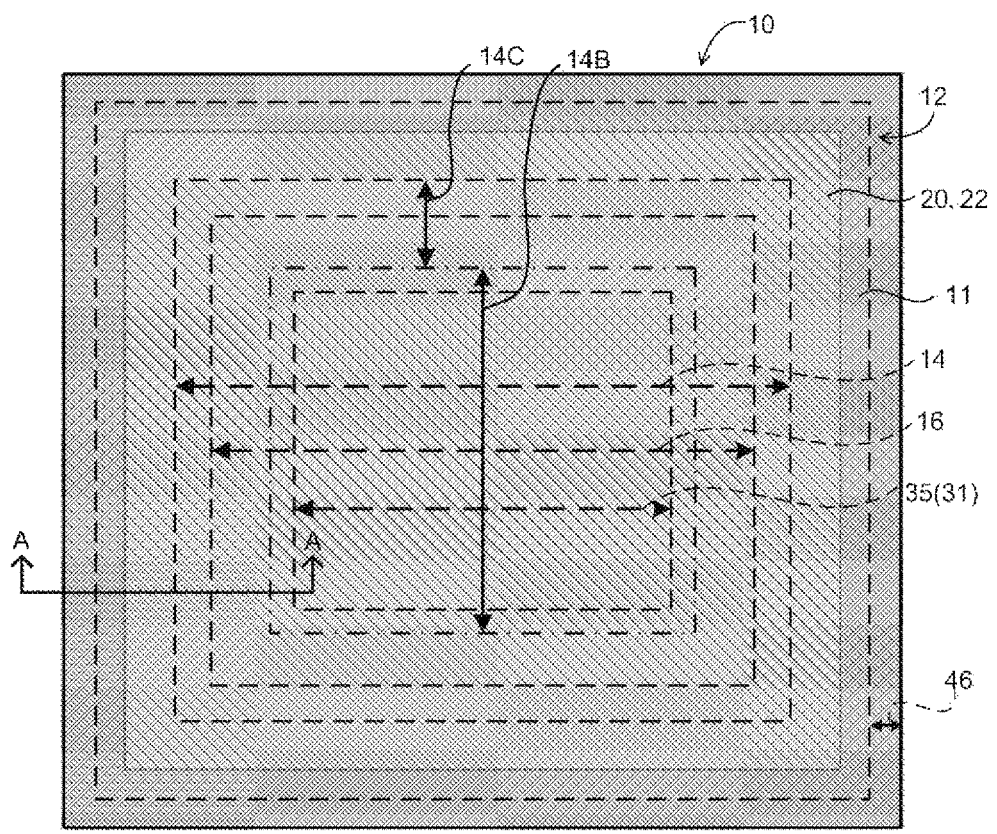
FIG. 6 is a plan view illustrating an example of a radiation detector of the first exemplary embodiment as viewed from a side provided with a conversion layer.
Figure 7:
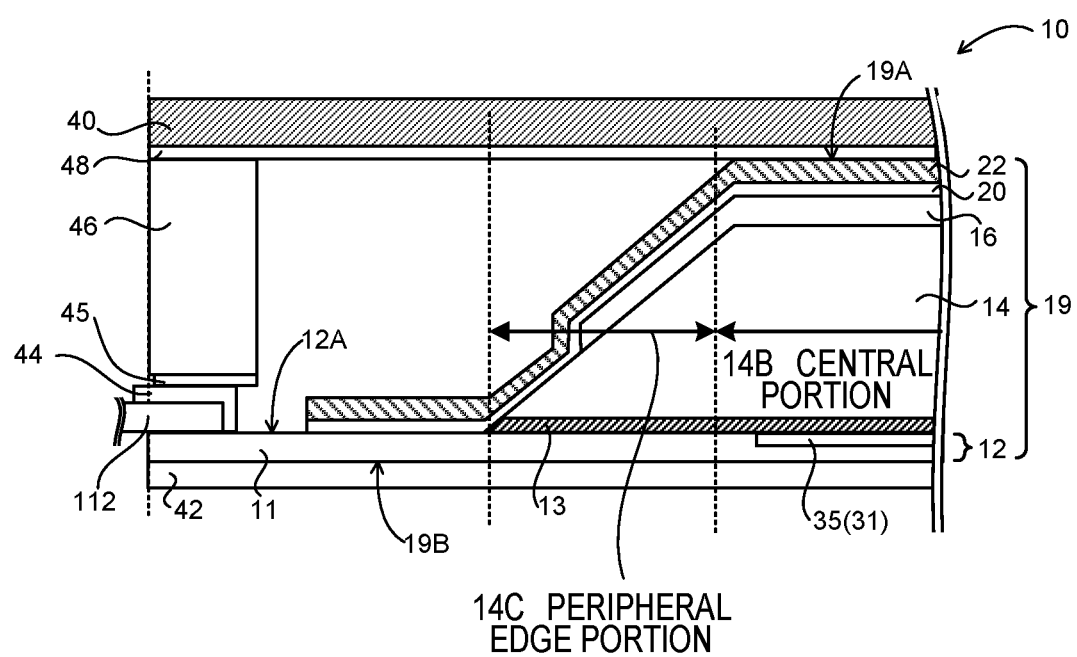
FIG. 7 is a cross-section of the radiation detector illustrated in FIG. 6, as sectioned along line A-A.

FIG. 6 is a plan view illustrating an example of the radiation detector 10 of the present exemplary embodiment, as viewed from the side formed with the conversion layer 14. FIG. 7 is a cross-section of the radiation detector 10, as sectioned along line A-A in FIG. 6.

Figure 8:
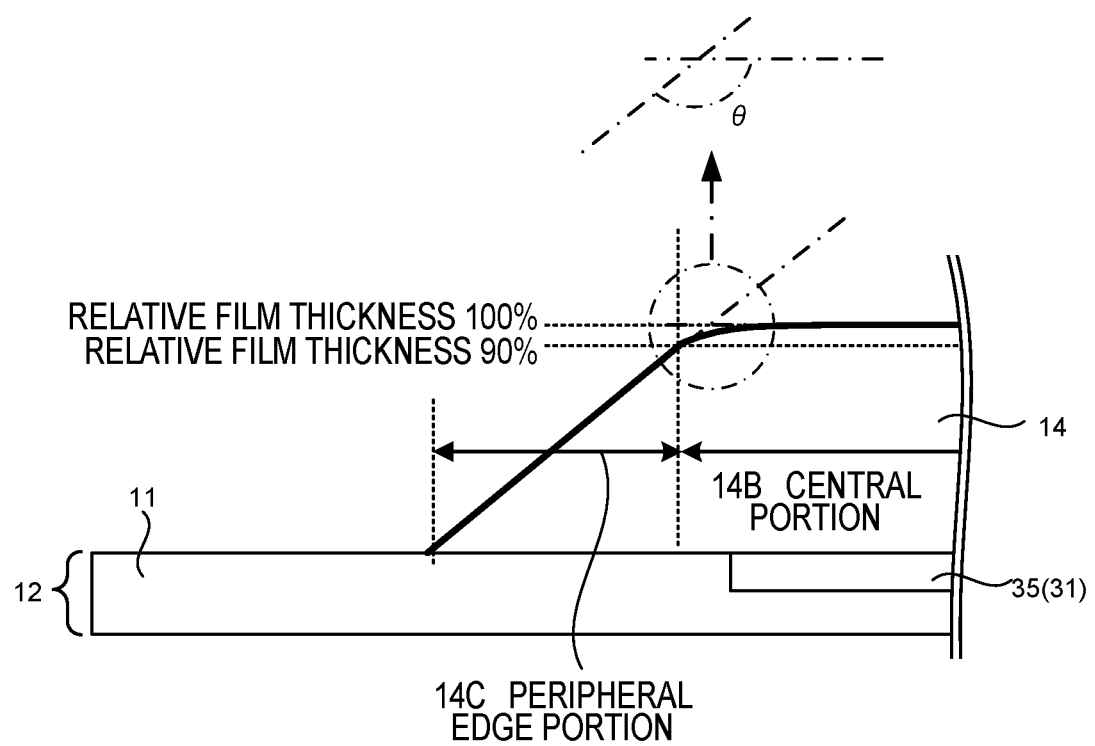
FIG. 8 is a cross-section to explain a peripheral edge portion and a central portion of a conversion layer of a second exemplary embodiment.

As illustrated in FIG. 7, the region at the outer periphery of the conversion layer 14 of the present exemplary embodiment tends to decrease in thickness on progression toward the outside when viewed as a whole, and thereby takes the form of a slope with decreasing thickness on progression toward the outside. In the present exemplary embodiment, an average value of the thickness of the conversion layer 14 within a predetermined range from the center of the conversion layer 14, where the thickness may be regarded as substantially constant if manufacturing error and measurement error are ignored, is taken as a reference. As illustrated in the example in FIG. 8, an outer peripheral region of the conversion layer 14 with a film thickness of no greater than 90% relative to the reference thickness (hereafter referred to as relative film thickness) is referred to as a peripheral edge portion (peripheral edge portion 14C). As illustrated in FIG. 8, a region of the conversion layer 14 surrounded by the peripheral edge portion 14C is referred to as a central portion (central portion 14B). In other words, the central portion refers to a region that includes at least a portion of the conversion layer 14 where the thickness is substantially constant, and also includes a portion where the relative film thickness exceeds 90%. Note that in the present exemplary embodiment, as illustrated in FIG. 7 and FIG. 8, the pixel region 35 is smaller than the central portion 14B, and the pixel region 35 is covered by the central portion 14B.

In the present exemplary embodiment as a specific example, an outer peripheral region that is in a region within 5 mm from the outer periphery of the conversion layer 14 and that has a relative film thickness of no greater than 90% is referred to as the peripheral edge portion (peripheral edge portion 14C). Thus, as illustrated in FIG. 7, FIG. 8, and so on, at the peripheral edge portion 14C, the conversion layer 14 tends to gradually decrease in thickness on progression toward the outer periphery (edge).

Note that although an example of a configuration in which the outer periphery has a constant slope at an incline angle of θ and gradually decreases in thickness has been given as an example of the thickness of the conversion layer 14 decreasing on progression toward its outer periphery in the present exemplary embodiment, there is no limitation to this configuration. For example, an embodiment may be applied in which the thickness changes with a stepped profile.

Although the method used to measure the incline angle θ is not particularly limited, as an example in the present exemplary embodiment, the incline angle θ is measured by taking samples by separating parts of an end portion of the conversion layer 14 from the TFT substrate 12 at positions at four locations at uniform intervals along one edge of the rectangular conversion layer 14. The four samples are polished and sectioned, and then inspected under an optical microscope to obtain a measurement. The average of the values measured for the four samples is taken as the incline angle θ of the edge of the conversion layer 14 from which the samples were taken.

Figure 10:
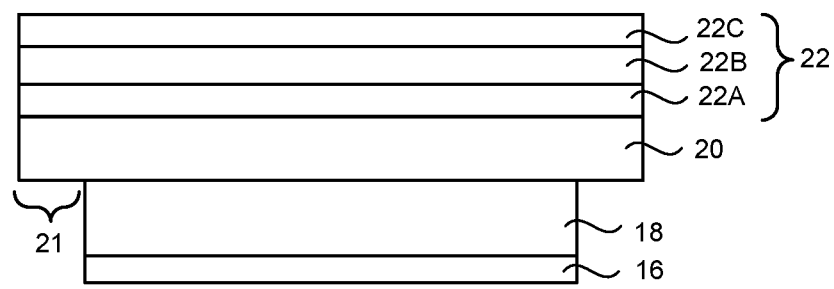
FIG. 10 is a cross-section schematically illustrating an example of an adhesion layer, a bonding layer, and a protective layer of the second exemplary embodiment.

As illustrated in FIG. 6 and FIG. 7, the stacked body 19 of the radiation detector 10 of the present exemplary embodiment differs from the stacked body 19 of the first exemplary embodiment in that an adhesion layer 16 and a bonding layer 20 are further provided. FIG. 10 is a cross-section schematically illustrating an example of a cross-section of the adhesion layer 16, the bonding layer 20, and the protective layer 22 of the present exemplary embodiment. As illustrated in FIG. 10, in the present exemplary embodiment, as an example the protective layer 22 is a stacked film configured by stacking a PET film 22A, an aluminum foil film 22B, and a PET film 22C.

Figure 9:
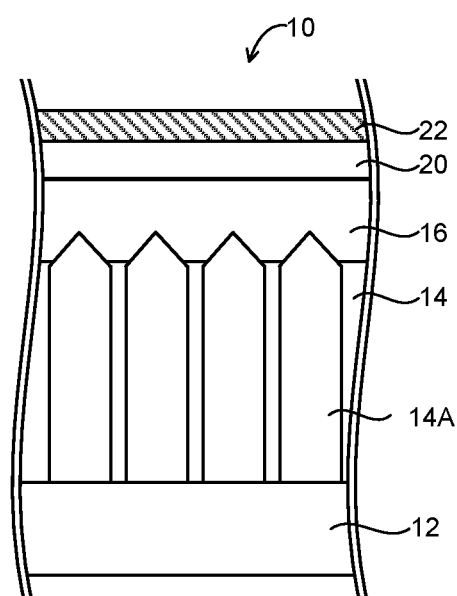
FIG. 9 is a cross-section illustrating an example of a stacked state of an adhesion layer, a bonding layer, and a protective layer in a radiation detector of the second exemplary embodiment.

As illustrated in the example of FIG. 6 and FIG. 7, the adhesion layer 16 is provided on top of a region including part of the peripheral edge portion 14C and the entirety of the central portion 14B of the conversion layer 14. In other words, the adhesion layer 16 covers the central portion 14B and part of the peripheral edge portion 14C of the conversion layer 14. As illustrated in FIG. 9, the tips of the conversion layer 14 intrude into the adhesion layer 16 in the radiation detector 10 of the present exemplary embodiment.

The adhesion layer 16 of the present exemplary embodiment is a reflective adhesion layer that reflects light converted by the conversion layer 14. In the present exemplary embodiment, as an example a white adhesion layer in which an inorganic white powder is dispersed in an adhesive resin is employed as the adhesion layer 16. In the present exemplary embodiment, "white" refers to a state in which all wavelengths of visible light are diffusely reflected, whereas a state in which reflection of light is directional is referred to as a "mirror". "Reflectivity" when the adhesion layer 16 and the like reflect light refers to a state in which an average of at least 80% of light from 500 nm to 550 nm is reflected.

The "adhesion layer" and the "bonding layer" have a function of making directly contacting layers less liable to detach, and in the present exemplary embodiment this applies to the detachment of the conversion layer 14 and a base member 18 from the adhesion layer 16. The "adhesion layer" and the "bonding layer" refer to layers in a state joined to a solid surface by some force, this not being limited to a chemical bond.

Examples of adhesive resins include acrylic glues. Examples of inorganic white powders include powders containing at least one out of titanium oxide ($TiO_2$), barium sulfate ($BaSO_4$), alumina ($Al_2O_3$), magnesium oxide (MgO), or calcium oxide (CaO). As an example, in the present exemplary embodiment a white powder filler is dispersed in a transparent glue (resin) to obtain the white adhesion layer.

As illustrated in FIG. 10, the adhesion layer 16 of the present exemplary embodiment is formed on the base member 18. The base member 18 is disposed on the bonding layer 20 side, and the adhesion layer 16 is disposed on the conversion layer 14 side (not illustrated in FIG. 10). Examples of the material of the base member 18 include reflective white polyethylene terephthalate (PET) that reflects light. The present exemplary embodiment is not limited thereto, and the base member 18 does not have to be reflective, and specifically, a material that does not reflect the light converted by the conversion layer 14, for example a light-transmitting material, may be employed therefor. However, a reflective material as employed in the present exemplary embodiment is preferable. Thus, light that could not be fully reflected by the adhesion layer 16 (that has leaked) can be reflected by the base member 18, enabling the overall reflectivity of the adhesion layer 16 and the base member 18 to be enhanced.

Note that white PET is PET to which a white pigment, such as $TiO_2$, barium sulfate, or the like, has been added. A highly reflective polyester sheet is a sheet (film) having a multi-layered structure of plural overlapping thin polyester sheets. A foamed white PET is a white PET with a porous surface.

The thicker the combined thickness of the adhesion layer 16 and the base member 18, the larger a step between an upper face of an outer peripheral portion of the adhesion layer 16 and the base member 18 and an upper face of the conversion layer 14. If this step is large, the protective layer 22 may lift up from the conversion layer 14 at this step portion when bonding the adhesion layer 16 with the protective layer 22 affixed thereto to the TFT substrate 12 formed with the conversion layer 14. Moreover, the thicker the combined thickness of the adhesion layer 16 and the base member 18, the greater the stiffness, making bending to follow the slope of the peripheral edge portion 14C of the conversion layer 14 more difficult, and making processing more difficult. On the other hand, the thinner the thickness of the adhesion layer 16, the lower the reflectivity. When the reflectivity decreases, there tends to be a reduction in the image quality of the radiographic images obtained by the radiation detector 10. The thickness of the adhesion layer 16 and the base member 18 is accordingly preferably set from the perspective of a desired reflectivity (for example, 80%) in consideration of the image quality of the radiographic images obtained by the radiation detector 10, and also from the perspectives of manufacturing and processing.

As in the example illustrated in FIG. 6 and FIG. 7, the bonding layer 20 covers a region including a region spanning from an end portion of the adhesion layer 16 to the front surface of the TFT substrate 12, and more specifically covers the entire conversion layer 14 where the adhesion layer 16 is provided and part of the front surface of the TFT substrate 12. In other words, in the radiation detector 10 of the present exemplary embodiment, the bonding layer 20 that covers the entire conversion layer 14 where the adhesion layer 16 is provided is fixed (bonded) directly to part of the front surface of the TFT substrate 12. The bonding layer 20 has a function of fixing the adhesion layer 16 and the protective layer 22 to the TFT substrate 12 and the conversion layer 14. Examples of materials that may be employed for the bonding layer 20 include acrylic-based adhesives, hot-melt-based adhesives, silicone-based bonding agents, and the like. Examples of acrylic-based adhesives include urethane acrylates, acrylic resin acrylates, epoxy acrylates, and the like. Examples of hot-melt-based adhesives include thermoplastic plastics such as copolymer resins of ethylene vinyl acetate (EVA), copolymer resins of ethylene and acrylic acid (EAA), copolymer resins of ethylene and ethyl acrylate (EEA), and copolymers of ethylene/methyl methacrylate (EMMA), and the like. Note that in the present exemplary embodiment, the bonding strength of the bonding layer 20 is stronger than the bonding strength of the adhesion layer 16.

The following is an example of a manufacturing method of the radiation detector 10 of the present exemplary embodiment.

The adhesion layer 16 is coated on the base member 18 that has been configured at a desired size suited to that of the radiation detector 10 in advance. The protective layer 22 is coated on the bonding layer 20 that has been configured at a desired size suited to that of the radiation detector 10. The base member 18 coated with the adhesion layer 16 and the protective layer 22 coated with the bonding layer 20 are then affixed to each other to prepare a stacked film in the state illustrated in FIG. 10. In the present exemplary embodiment, as illustrated in FIG. 10 the base member 18 and the adhesion layer 16 are smaller than the bonding layer 20 and the protective layer 22, and a bonding portion 21 is provided at the periphery of the base member 18 and the adhesion layer 16.

The stacked film is then disposed on the TFT substrate 12 formed with the conversion layer 14 similarly to in the radiation detector 10 of the first exemplary embodiment, such that the stacked film covers the entire conversion layer 14. The bonding portion 21 is affixed to the TFT substrate 12 so as to seal the conversion layer 14, thereby forming the stacked body 19.

The reinforcement substrate 40 provided with the spacer 46, prepared similarly to in the first exemplary embodiment, is then affixed to the TFT substrate 12 formed with the stacked body 19, thereby sealing the stacked body 19. The TFT substrate 12 is then separated from the support body 50 (see FIG. 5) using the separation layer 52 (see FIG. 5).

In the radiation detector 10 of the present exemplary embodiment, the bonding layer 20 and the protective layer 22 cover the entire adhesion layer 16. The bonding layer 20 and the protective layer 22 are also fixed directly on top of the TFT substrate 12.

Covering the top of the peripheral edge portion 14C of the conversion layer 14 with the adhesion layer 16 that has a light-reflecting function in order to gather (reflect) more of the light converted by the conversion layer 14 on top of the TFT substrate 12 tends to make the adhesion layer 16 more susceptible to detachment from the conversion layer 14 at the sloped peripheral edge portion 14C. Since the base member 11 of the TFT substrate 12 is flexible, bending of the TFT substrate 12 tends to make the adhesion layer 16 more susceptible to detachment from the conversion layer 14. To address this, the radiation detector 10 of the present exemplary embodiment suppresses such detachment of the adhesion layer 16 using the above configuration, thus suppressing detachment of the conversion layer 14.

In the radiation detector 10 of the present exemplary embodiment, the adhesion layer 16 includes the functionality of both a layer with a light-reflecting function and an adhesive layer. This enables the thickness of the adhesion layer 16 to be increased in comparison to cases in which separate layers are provided. Accordingly, the adhesive force in the radiation detector 10 of the present exemplary embodiment can be increased, discouraging detachment of the adhesion layer 16.

The spacing between the conversion layer 14 and the layer with a light-reflecting function is preferably narrow from the perspectives of modulation transfer function (MTF) and detective quantum efficiency (DQE). In the radiation detector 10 of the present exemplary embodiment, the reflective adhesion layer 16 with a light-reflecting function is formed directly on top of the conversion layer 14. Accordingly, the radiation detector 10 of the present exemplary embodiment enables the spacing between the conversion layer 14 and the layer with a light-reflecting function to be narrowed. Accordingly, the radiation detector 10 of the present exemplary embodiment is better capable of suppressing detachment of the layer with a light-reflecting function without a reduction in the image quality of the radiographic images than in cases in which an adhesive layer is provided between the layer with a light-reflecting function and the conversion layer.

As illustrated in FIG. 7, the radiation detector 10 of the present exemplary embodiment is also provided with the reinforcement substrate 40 on the first surface 19A of the stacked body 19. Accordingly, the radiation detector 10 of the present exemplary embodiment is also capable of suppressing the TFT substrate 12 from bending greatly, enabling breakage of the conversion layer 14 to be suppressed.

Third Exemplary Embodiment

Figure 11:
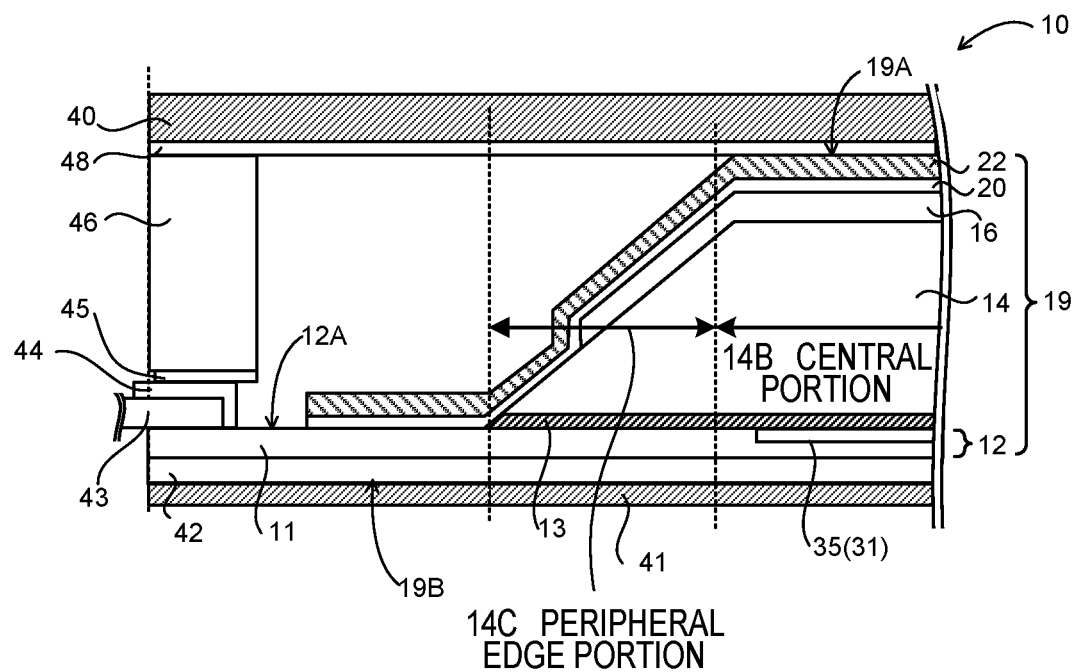
FIG. 11 is a cross-section illustrating an example of a radiation detector of a third exemplary embodiment.

Next, explanation follows regarding a third exemplary embodiment. FIG. 11 is a cross-section illustrating an example of a radiation detector 10 of the present exemplary embodiment.

As illustrated in FIG. 11, in the radiation detector 10 of the present exemplary embodiment, a reinforcement substrate 41 is provided to the second surface 19B, this being the surface on the TFT substrate 12 side of the stacked body 19. In the radiation detector 10 of the present exemplary embodiment, as illustrated in FIG. 11, the protective film 42 is provided between the TFT substrate 12 and the reinforcement substrate 41, similarly to in the exemplary embodiments described above.

Similarly to the reinforcement substrate 40, the reinforcement substrate 41 has a higher rigidity than the base member 11, such that dimensional change (deformation) with respect to force applied in a direction perpendicular to a surface opposing the first surface 19B is smaller than the dimensional change of the base member 11 with respect to force applied in a direction perpendicular to the first surface 19B. The thickness of the reinforcement substrate 41 of the present exemplary embodiment is thicker than the thickness of the base member 11, and thinner than the thickness of the reinforcement substrate 40. Note that the reinforcement substrate 41 preferably has similar characteristics to those of the reinforcement substrate 40. The material employed for the reinforcement substrate 41 of the present exemplary embodiment is preferably a thermoplastic resin, and similar materials to those of the reinforcement substrate 40 may be employed, or alternatively the reinforcement substrate 40 and the reinforcement substrate 41 may be configured from different materials to each other.

In the radiation detector 10 of the present exemplary embodiment, a similar manufacturing method to the manufacturing method of the radiation detector 10 described above in the first exemplary embodiment may employed to affix the reinforcement substrate 40 provided with the spacer 46 to the TFT substrate 12 provided with the stacked body 19, and then separate the TFT substrate 12 from the support body 50. The radiation detector 10 of the present exemplary embodiment can then be manufactured by performing coating or the like to provide the protective film 42 and the reinforcement substrate 41 on the first surface 19A of the TFT substrate 12.

In the radiation detector 10 of the present exemplary embodiment, the reinforcement substrate 40 is provided on the first surface 19A of the stacked body 19, and the reinforcement substrate 41 is provided on the second surface 19B of the stacked body 19. This enables the TFT substrate 12 to be further suppressed from bending greatly, thus enabling breakage of the conversion layer 14 to be suppressed, compared to the radiation detector 10 of the exemplary embodiment described above.

Fourth Exemplary Embodiment

Figure 12:
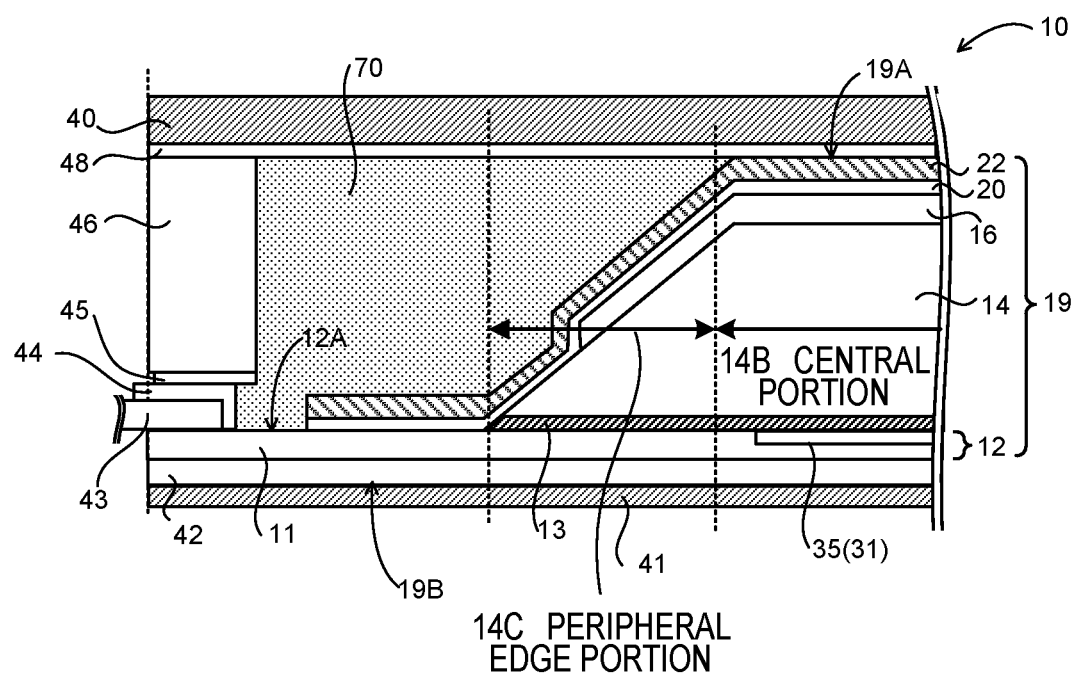
FIG. 12 is a cross-section illustrating an example of a radiation detector of a fourth exemplary embodiment.

Next, explanation follows regarding a fourth exemplary embodiment. FIG. 12 is a cross-section illustrating an example of a radiation detector 10 of the present exemplary embodiment.

As illustrated in FIG. 12, in the radiation detector 10 of the present exemplary embodiment, a filler 70 is filled between the adhesion layer 48 and the first surface 12A of the TFT substrate 12 formed with the stacked body 19. Namely, the radiation detector 10 of the present exemplary embodiment differs from the radiation detector 10 of the second exemplary embodiment (see FIG. 7) in that a space that is present between the reinforcement substrate 40 (adhesion layer 48) and the TFT substrate 12 formed with the stacked body 19 is filled with the filler 70.

The material of the filler 70 is not particularly limited, and a general semiconductor material sealant or the like may be employed therefor. The method of providing the filler 70 is not particularly limited. For example, the filler 70 may be provided by pouring flowable filler 70 into the space (gap) between the TFT substrate 12 on which the stacked body 19 is stacked and the reinforcement substrate 40 provided with the adhesion layer 48, and then curing the filler 70. Alternatively, for example, after forming the stacked body 19 on the TFT substrate 12, the filler 70 may be provided by placing flowable filler 70 at a location to be filled using the filler 70, and then affixing the reinforcement substrate 40 provided with the spacer 46 on top of the stacked body 19 and the filler 70.

Thus, in the radiation detector 10 of the present exemplary embodiment, the filler 70 is filled between the stacked body 19 and the reinforcement substrate 40, such that the reinforcement substrate 40 that projects beyond the central portion 14B of the conversion layer 14 (toward the end portion side of the TFT substrate 12) is supported by the filler 70. Thus, in the radiation detector 10 of the present exemplary embodiment, the reinforcement substrate 40 is stably provided and is less liable to detach from the TFT substrate 12 and the stacked body 19. Moreover, in the radiation detector 10 of the present exemplary embodiment, the stacked body 19 is fixed to the TFT substrate 12 by both the reinforcement substrate 40 and the filler 70, such that the conversion layer 14 is less liable to detach from the TFT substrate 12.

Note that although the space between the TFT substrate 12 formed with the stacked body 19 and the reinforcement substrate 40 is entirely filled with the filler 70 without leaving any gaps in the example illustrated in FIG. 12, there is no limitation to the embodiment illustrated in FIG. 12. For example, a local gap (a region where the filler 70 is not formed) may be left between the TFT substrate 12 formed with the stacked body 19 and the reinforcement substrate 40.

In the radiation detector 10 of the present exemplary embodiment, due to providing the reinforcement substrate 40 on the first surface 19A of the stacked body 19, the TFT substrate 12 can be suppressed from bending greatly, similarly to in the radiation detectors 10 of the exemplary embodiments described above, thus enabling breakage of the conversion layer 14 to be suppressed.

Fifth Exemplary Embodiment

Figure 13:
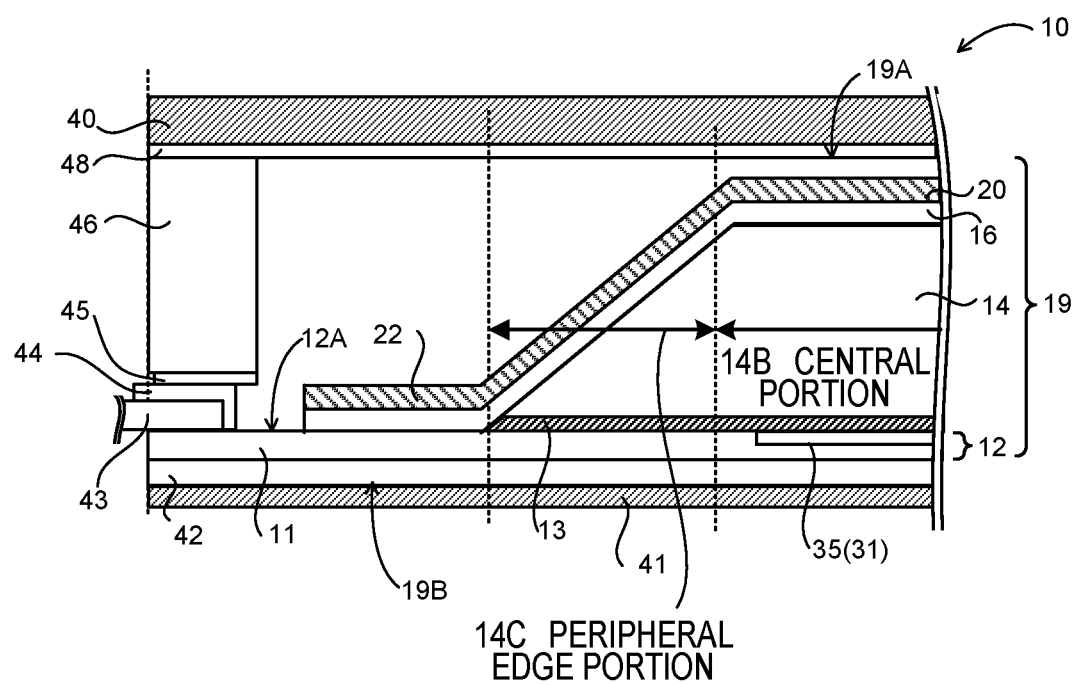
FIG. 13 is a cross-section illustrating an example of a radiation detector of a fifth exemplary embodiment.
Figure 14:
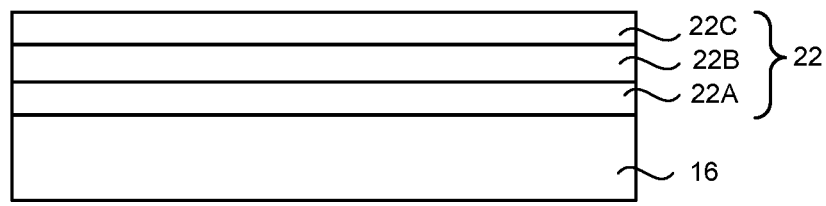
FIG. 14 is a cross-section illustrating an example of a stacked state of an adhesion layer and a protective layer in a radiation detector of the fifth exemplary embodiment.

Next, explanation follows regarding a fifth exemplary embodiment. In a radiation detector 10 of the present exemplary embodiment, the configuration of the adhesion layer 16 and the region where the adhesion layer 16 is provided differ from those in the second to the fourth exemplary embodiments, and so explanation follows regarding the configuration of the adhesion layer 16 and the region where the adhesion layer 16 is provided, with reference to the drawings. FIG. 13 is a cross-section illustrating an example of the radiation detector 10 of the present exemplary embodiment. FIG. 14 is a cross-section schematically illustrating an example of a cross-section through the adhesion layer 16 and the protective layer 22 of the present exemplary embodiment.

As illustrated in FIG. 13, in the radiation detector 10 of the present exemplary embodiment, the adhesion layer 16 is provided over the entirety of a region on top of the conversion layer 14 including the central portion 14B and the peripheral edge portion 14C, and a region on top of the TFT substrate 12 in the vicinity of the outer periphery of the conversion layer 14. As illustrated in FIG. 13 and FIG. 14, the radiation detector 10 of the present exemplary embodiment differs from the radiation detectors 10 of the second to fourth exemplary embodiments in that the protective layer 22 is provided directly on top of the adhesion layer 16, and the bonding layer 20 is not provided.

In the present exemplary embodiment, an adhesion layer configured of a thermoplastic resin in which an inorganic white powder is dispersed is employed as an example of the adhesion layer 16. What is referred to as a hot melt resin may be employed as the thermoplastic resin, and more specifically, polyolefin-based, polyester-based, EVA, or the like may be employed therefor. Similarly to in the adhesion layer 16 of the first to third exemplary embodiments described above, examples of the inorganic white powder include powders containing at least one out of titanium oxide ($TiO_2$), barium sulfate ($BaSO_4$), alumina ($Al_2O_3$), magnesium oxide (MgO), or calcium oxide (CaO).

As illustrated in FIG. 14, as an example the protective layer 22 of the radiation detector 10 of the present exemplary embodiment is also a stacked film in which the protective layer 22 is configured by stacking the PET film 22A, the aluminum foil film 22B, and the PET film 22C.

Explanation follows regarding an example of a manufacturing method of the radiation detector 10 of the present exemplary embodiment.

The adhesion layer 16 is coated directly onto the protective layer 22 that has been configured at a desired size suited to that of the radiation detector 10 in advance. Note that in the radiation detector 10 of the present exemplary embodiment, since the adhesion layer 16 also serves to seal the end portion of the protective layer 22, the adhesion layer 16 is coated over the entire surface of the protective layer 22. The stacked body 19 is formed on top of the TFT substrate 12 as described previously. The adhesion layer 16 coated on the protective layer 22 is then affixed to the TFT substrate 12 to seal the conversion layer 14.

In the radiation detector 10 of the present exemplary embodiment, the adhesion layer 16 covers the entire conversion layer 14, and also covers the front surface of the base member 11, enabling the adhesion layer 16 to be sufficiently fixed to the TFT substrate 12 and the conversion layer 14. Moreover, in the radiation detector 10 of the present exemplary embodiment, the adhesion layer 16 is provided directly to the conversion layer 14. Accordingly, the radiation detector 10 of the present exemplary embodiment is capable of suppressing detachment of the adhesion layer 16 without a reduction in the image quality of the radiographic images, similarly to the radiation detectors 10 of the second to fourth exemplary embodiments described above.

As described above, the radiation detectors 10 of the exemplary embodiments described above each include the TFT substrate 12 including the base member 11 that is flexible and made of resin and that includes the fine particle layer 11L containing the inorganic fine particles 11P having a mean particle size of from 0.05 μm to 2.5 μm, and is formed with the plural pixels 30 configured to accumulate electrical charge generated in response to light converted from radiation in the pixel region 35 on the first surface 12A of the TFT substrate 12 on the opposite side to the surface including the fine particle layer 11L. The radiation detectors 10 also include the conversion layer 14 that is provided on the first surface 12A of the base member 11 provided with the pixel region 35 and that converts radiation into light, and at least one out of the reinforcement substrate 41 provided on the second surface 19B, this being the surface on the TFT substrate 12 side of the stacked body 19 configured by stacking the TFT substrate 12 and the conversion layer 14, or the reinforcement substrate 40 provided on the surface that is the first surface 19A, this being the surface on the conversion layer 14 side of the stacked body 19.

In the radiation detectors 10 of the exemplary embodiments described above, providing at least one out of the reinforcement substrate 40 or the reinforcement substrate 41 to the stacked body 19 enables the TFT substrate 12 to be suppressed from bending greatly. Accordingly, the radiation detectors 10 of the exemplary embodiments described above are each capable of suppressing breakage of the conversion layer 14 when the radiation detector 10 is on its own.

Note that it is sufficient that the radiation detector 10 include at least one out of the reinforcement substrate 40 or the reinforcement substrate 41. There is accordingly no limitation to the exemplary embodiments described above, and the radiation detector 10 may include the reinforcement substrate 41 alone.

Figure 15:
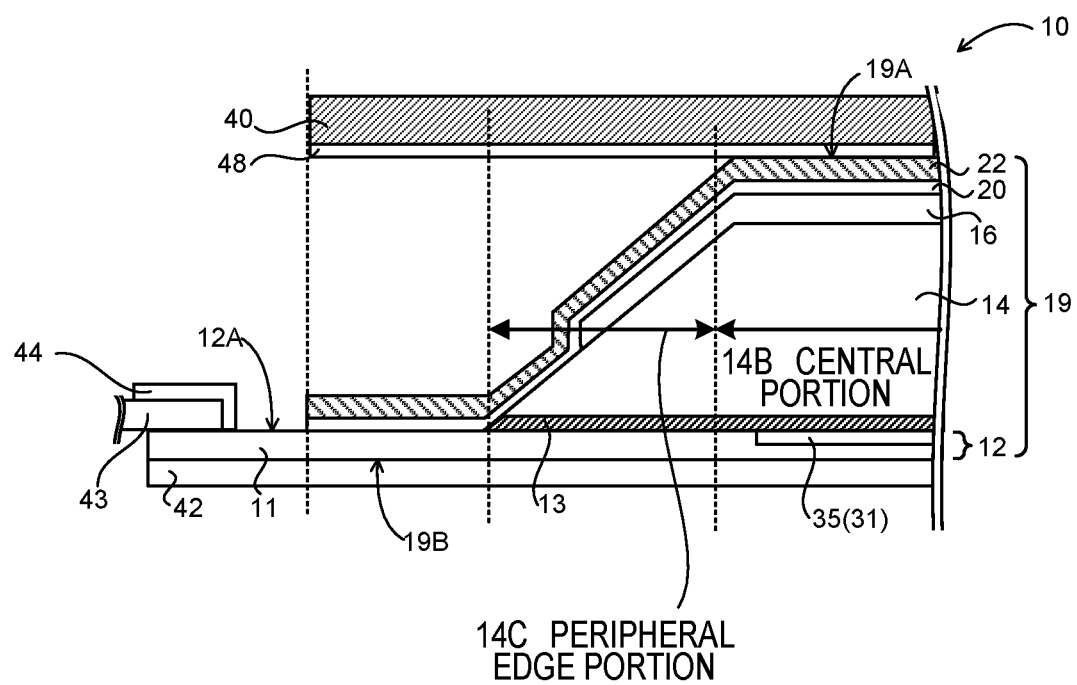
FIG. 15 is a cross-section illustrating another example of a radiation detector of an exemplary embodiment.

Moreover, the sizes of the reinforcement substrate 40 and the reinforcement substrate 41 are not limited to those of the exemplary embodiments described above. For example, as in the example illustrated in FIG. 15, end portions (outer peripheries) of the reinforcement substrate 40 and the adhesion layer 48 may be provided at similar positions to outer end portions (outer peripheries) of the protective layer 22 and the bonding layer 20. Note that a wider region than the region where the conversion layer 14 covers the first surface 12A of the TFT substrate 12 is preferably covered by at least one out of the reinforcement substrate 40 or the reinforcement substrate 41.

Figure 16:
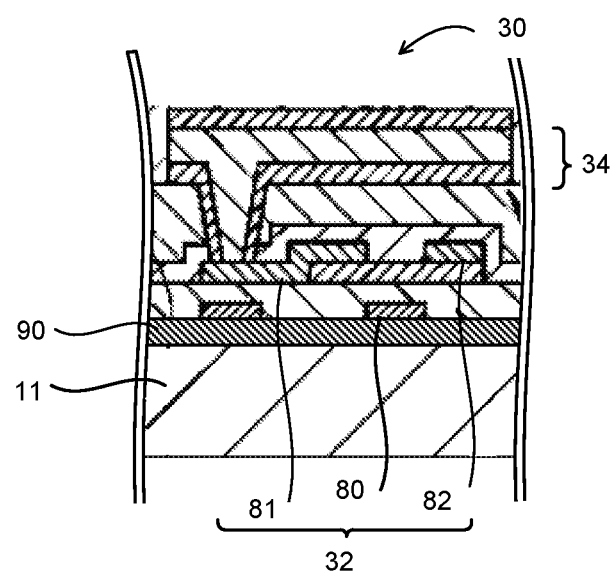
FIG. 16 is a cross-section illustrating a location corresponding to a single pixel in another example of a radiation detector of an exemplary embodiment.

As in the example illustrated in FIG. 16, a layer 90 configured of an inorganic material is preferably provided between the base member 11 and the pixels 30, and in particular between the base member 11 and gate electrodes 80 of the TFTs 32 of the pixels 30. Examples of the inorganic material employed in the example illustrated in FIG. 16 include SiNx, SiOx, and the like. Drain electrodes 81 and source electrodes 82 of the TFTs 32 are formed in the same layer as each other, and the gate electrodes 80 are formed between the base member 11 and the layer formed with the drain electrodes 81 and the source electrodes. The layer 90 that is configured of an inorganic material is provided between the base member 11 and the gate electrodes 80.

Figure 17:
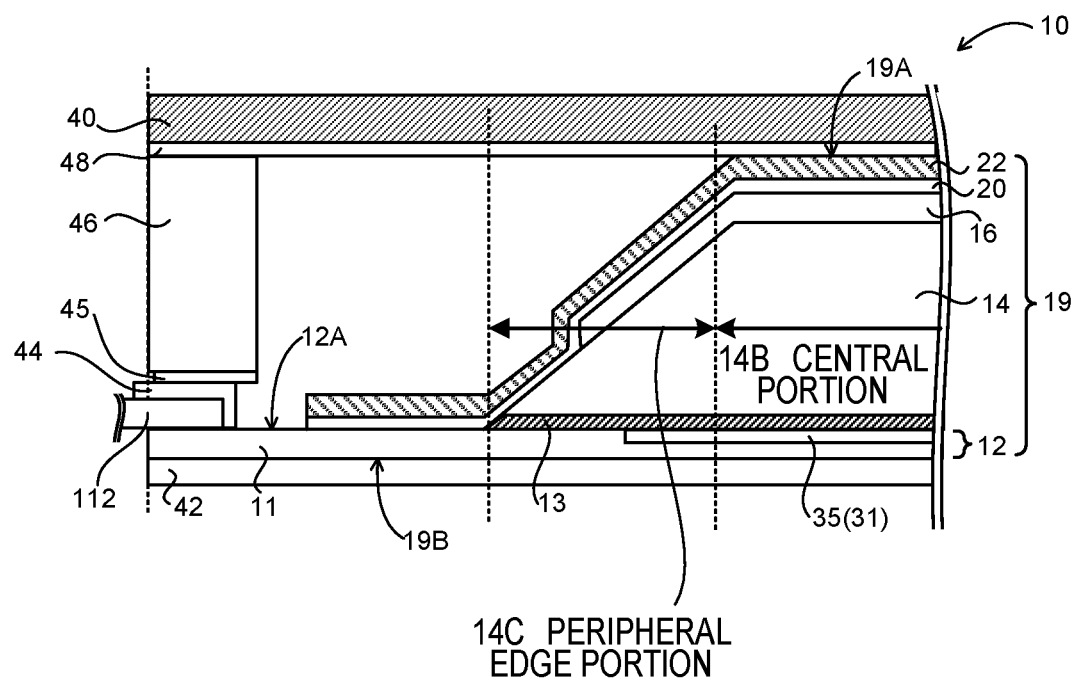
FIG. 17 is a cross-section illustrating another example of a radiation detector of an exemplary embodiment.

The size of the pixel array 31 (pixel region 35) is not limited to that in the exemplary embodiments described above. For example, in the second to fifth exemplary embodiments, explanation has been given regarding embodiments in which the size of the pixel array 31 (pixel region 35) is smaller than the size of the central portion 14B of the conversion layer 14, such that the outer periphery of the pixel array 31 (pixel region 35) is within the central portion 14B. However, the pixel array 31 (pixel region 35) is not limited to these embodiments, and as illustrated in the radiation detector 10 in the example in FIG. 17, the size of the pixel array 31 (pixel region 35) may be larger than the size of the central portion 14B of the conversion layer 14, such that the outer periphery of the pixel array 31 (pixel region 35) may reach the peripheral edge portion 14C of the conversion layer 14. Note that since the amount of light converted from radiation by the conversion layer 14 tends to decrease as the thickness of the conversion layer 14 becomes thinner, in embodiments in which the outer periphery of the pixel array 31 (pixel region 35) is within the central portion 14B similarly to in the radiation detectors 10 of the exemplary embodiments described above, the conversion layer 14 has a substantially uniform thickness on top of the pixel array 31 (pixel region 35), thus improving the sensitivity characteristics of the pixel region 35. Conversely, the radiation detector 10 of the example illustrated in FIG. 17 enables the overall size of the radiation detector 10 to be made smaller.

In the exemplary embodiments described above, explanation has been given regarding embodiments in which the pixels 30 are arrayed on a two-dimensional matrix as illustrated in FIG. 1. However, there is no limitation thereto, and the pixels 30 may be arrayed in one dimension, or may be arrayed in a honeycomb formation. The shape of the pixels is not limited, and the pixels may be rectangular or polygonal, for example hexagonal, in shape. Obviously the shape of the pixel array 31 (pixel region 35) is likewise not limited.

The shape and the like of the conversion layer 14 are also not limited to that of the exemplary embodiments described above. In the exemplary embodiments described above, explanation has been given regarding embodiments in which the shape of the conversion layer 14 is a rectangular shape similar to the shape of the pixel array 31 (pixel region 35). However, the shape of the conversion layer 14 does not have to be a similar shape to that of the pixel array 31 (pixel region 35). Moreover, instead of being rectangular, the shape of the pixel array 31 (pixel region 35) may for example be another polygonal shape, or may be circular.

Note that in the exemplary embodiments described above, as an example, explanation has been given of a configuration in which the conversion layer 14 of the radiation detector 10 is configured by a scintillator containing CsI. However, the conversion layer 14 may be configured by a scintillator in which GOS or the like is dispersed in a binder such as a resin. A conversion layer 14 employing GOS is for example formed by directly coating the binder in which the GOS is dispersed on top of the TFT substrate 12, a separation layer, or the like, and then drying and solidifying. As the method for forming the conversion layer 14, for example, a geyser method may be adopted in which a coating liquid is coated in a region for forming the conversion layer 14 while controlling the thickness of the coating film. Note that in such cases, prior to coating the binder in which the GOS is dispersed, surface processing may be performed to activate the front surface of the pixel array 31. Furthermore, an inter-layer insulating film, a surface protection film may be provided on the front surface of the pixel array 31.

Note that in the radiation detectors 10 of the exemplary embodiments described above, either an ISS approach, in which radiation is irradiated from the TFT substrate 12 side, may be adopted for the radiographic imaging device, or a penetration side sampling PSS approach, in which radiation is irradiated from the conversion layer 14 side, may be adopted for the radiographic imaging device.

Figure 18:
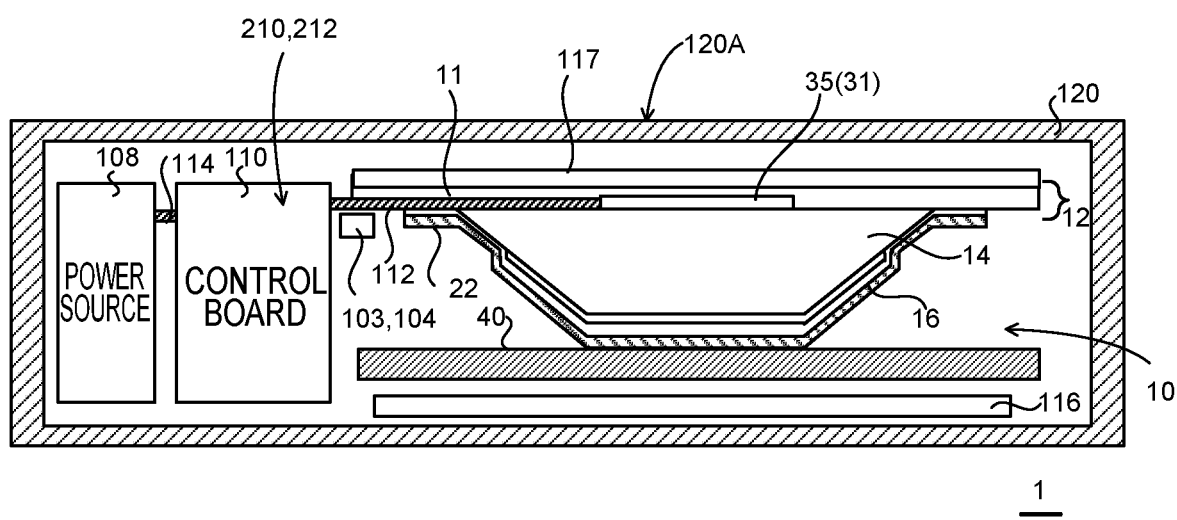
FIG. 18 is a cross-section illustrating an example of a radiographic imaging device applied with a radiation detector of an exemplary embodiment.

FIG. 18 is a cross-section illustrating an example of a state in which a radiographic imaging device 1 employing an ISS approach is applied with the radiation detector 10 of the first exemplary embodiment.

As illustrated in FIG. 18, the radiation detector 10, a power source section 108, and a control board 110 are provided arranged inside a case 120 in a direction intersecting a direction in which radiation is incident. In the radiation detector 10, the side of the pixel array 31 not provided with the conversion layer 14 is provided opposing an imaging face 120A side of the case 120 that is irradiated with radiation that has passed through the imaging subject.

The control board 110 is a substrate formed with image memory 210 configured to store image data according to the electrical charges read from the pixels 30 of the pixel array 31, a control section 212 configured to control reading of the electrical charges from the pixels 30, and the like. The control board 110 is electrically connected to the pixels 30 of the pixel array 31 through the flexible cable 112 including the plural signal lines. Note that in the radiographic imaging device 1 illustrated in FIG. 18, the drive section 103 that controls the switching states of the TFTs 32 of the pixels 30 under the control of the control section 212, and the signal processing section 104 that generates and outputs image data corresponding to the electrical charges read from the pixels 30 are configured by the COF provided on top of the flexible cable 112. However, at least one out of the drive section 103 or the signal processing section 104 may be formed on the control board 110.

A power source line 114 connects the control board 110 to the power source section 108 so as to supply electrical power to the image memory 210, the control section 212, and the like formed on the control board 110.

The case 120 is preferably lightweight, has a low absorption ratio of the radiation R, in particular X-rays, and high rigidity, and is preferably configured from a material that has a sufficiently high elastic modulus. A material having a bending elastic modulus of at least 10,000 MPa is preferably employed as the material of the case 120. Examples of materials that may be suitably employed as the material of the case 120 include carbon or carbon fiber reinforced plastic (CFRP) having a bending elastic modulus of around 20,000 MPa to 60,000 MPa.

During capture of radiographic images by the radiographic imaging device 1, a load is applied to the imaging face 120A of the case 120 from the imaging subject. If the rigidity of the case 120 were insufficient, the load from the imaging subject would cause the TFT substrate 12 to bend, and there would be a concern of faults occurring such as damage to the pixels 30. Housing the radiation detector 10 inside the case 120 configured from a material having a bending elastic modulus of at least 10,000 MPa enables bending of the TFT substrate 12 due to the load from the imaging subject to be suppressed.

A sheet 116 is provided inside the case 120 of the radiographic imaging device 1 illustrated in FIG. 18 on the side where radiation that has passed through the radiation detector 10 is emitted. The sheet 116 may, for example, be a copper sheet. A copper sheet does not readily generate secondary radiation from incident radiation, and thus has a function of preventing scattering toward the rear, namely toward the conversion layer 14 side. Note that the sheet 116 at least covers the entire surface on the radiation emission side of the conversion layer 14 and preferably covers the entire conversion layer 14.

A protective layer 117 is further provided inside the case 120 of the radiographic imaging device 1 illustrated in FIG. 18 on the side to which radiation is incident (the imaging face 120A side). The protective layer 117 may, for example, be configured by a moisture-proof film such as an ALPET (registered trademark) sheet in which aluminum is stacked by for example bonding aluminum foil to an insulating sheet (film), or an insulating sheet such as a Parylene (registered trademark) film or PET. The protective layer 117 has a moisture-proof function and an anti-static function with respect to the pixel array 31. Accordingly, the protective layer 117 preferably covers at least the entire surface of the pixel array 31 on the side to which the radiation is incident, and preferably covers the entire surface of the TFT substrate 12 on the side to which the radiation is incident.

Note that FIG. 18 illustrates an embodiment in which both the power source section 108 and the control board 110 are provided on one side of the radiation detector 10, specifically on the side of one edge of the rectangular pixel array 31. However, the positions at which the power source section 108 and the control board 110 are provided are not limited to those of the embodiment illustrated in FIG. 18. For example, the power source section 108 and the control board 110 may be provided distributed between two opposing edges of the pixel array 31, or may be provided distributed between two adjacent edges of the pixel array 31.

Figure 56:
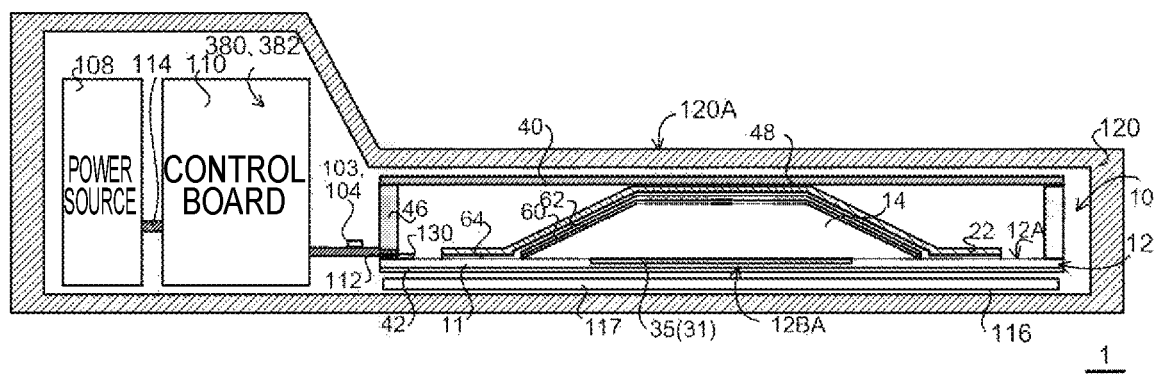
FIG. 56 is a cross-section illustrating an example of configuration of a radiographic imaging device of an exemplary embodiment of technology disclosed herein.
Figure 57:
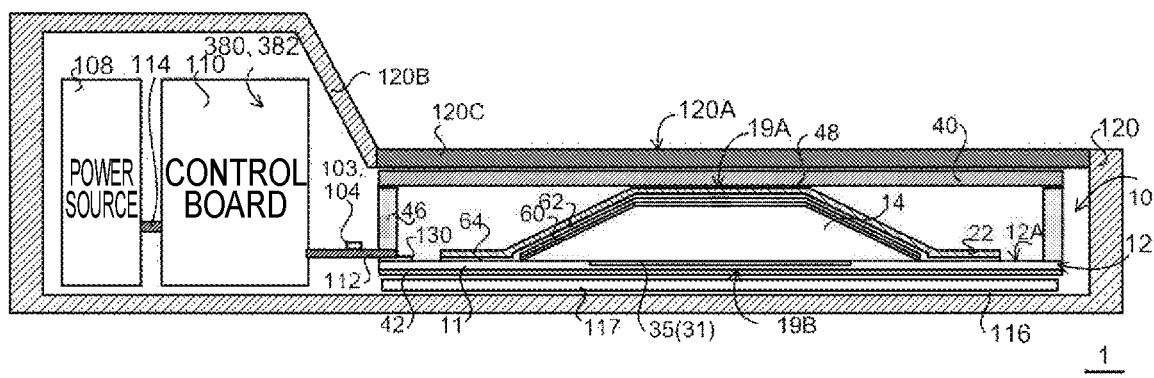
FIG. 57 is a cross-section illustrating an example of configuration of a radiographic imaging device of an exemplary embodiment of technology disclosed herein.

For example, locations of the case 120 provided with the power source section 108 and the control board 110 and a location of the case 120 provided with the radiation detector 10 may have different thicknesses to each other. As illustrated in FIG. 18, the power source section 108 and the control board 110 are often each thicker than the radiation detector 10. In such cases, the thickness of the location of the case 120 where the radiation detector 10 is provided may be thinner than the thickness of the locations of the case 120 where the power source section 108 and the control board 110 are provided (see FIG. 56 to FIG. 58, described in detail later). In cases in which the thickness is varied between the locations of the case 120 where the power source section 108 and the control board 110 are respectively provided and the location of the case 120 where the radiation detector 10 is provided in this manner, since there might be a concern of causing discomfort to the imaging subject who touches a boundary where a step is created at a boundary between these locations, the boundary is preferably provided with a slope.

As another example, the case 120 may be configured of different materials at the locations of the case 120 where the power source section 108 and the control board 110 are provided and the location of the case 120 where the radiation detector 10 is provided. Moreover, for example, the locations of the case 120 where the power source section 108 and the control board 110 are provided and the location of the case 120 where the radiation detector 10 is provided may be configured separately to each other.

Figure 19:
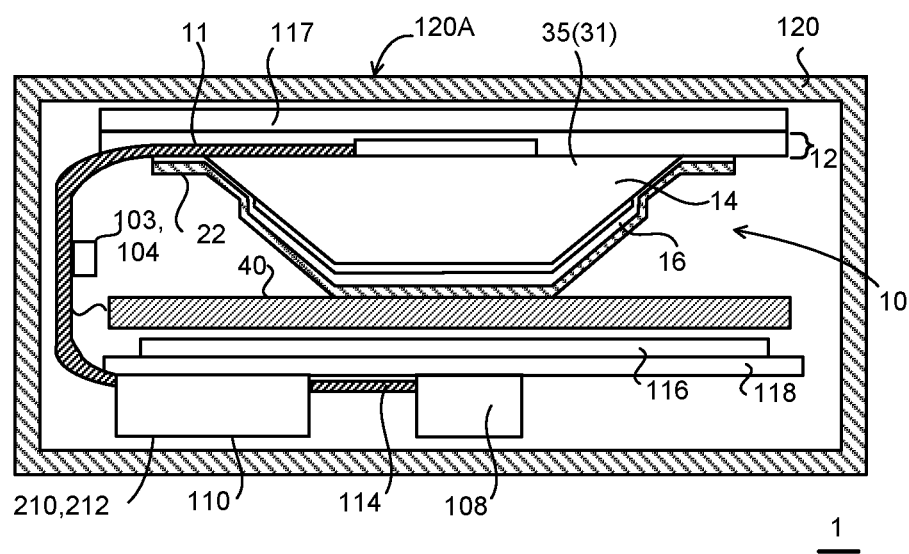
FIG. 19 is a cross-section illustrating another example of a radiographic imaging device applied with a radiation detector of an exemplary embodiment.

FIG. 19 is a cross-section illustrating another example of a state in which the radiation detector 10 of the first exemplary embodiment is applied to a radiographic imaging device 1 employing an ISS approach.

As illustrated in FIG. 19, the power source section 108 and the control board 110 are provided arranged inside the case 120 in a direction intersecting the direction in which radiation is incident, and the radiation detector 10 and the power source section 108 and control board 110 are provided arranged inside the case 120 along the direction in which radiation is incident.

In the radiographic imaging device 1 illustrated in FIG. 19, a base 118 is provided between the control board 110 and power source section 108 and the sheet 116 to support the radiation detector 10 and the control board 110. For example, carbon or the like is employed for the base 118.

The configurations and manufacturing methods of the radiation detector 10 and so on of the exemplary embodiments described above are merely examples thereof, and obviously modifications are possible according to circumstances within a range not departing from the spirit of the present invention.

Other Exemplary Embodiments

First, explanation follows regarding other exemplary embodiments of the reinforcement substrate 40, with reference to FIG. 20 to FIG. 41.

As illustrated in FIG. 20 to FIG. 40, an adhesion layer 60, a reflective layer 62, a bonding layer 64, the protective layer 22, and the adhesion layer 48 may be provided between the conversion layer 14 and the reinforcement substrate 40.

The adhesion layer 60 covers the entire front surface of the conversion layer 14, including the central portion 14B and the peripheral edge portion 14C of the conversion layer 14. The adhesion layer 60 includes a function to fix the reflective layer 62 onto the conversion layer 14. The adhesion layer 60 preferably has light-transmitting properties. Examples of materials that may be employed for the adhesion layer 60 include acrylic-based adhesives, hot-melt-based adhesives, silicone-based bonding agents, and the like. Examples of acrylic-based adhesives include urethane acrylates, acrylic resin acrylates, epoxy acrylates, and the like. Examples of hot-melt-based adhesives include thermoplastic plastics such as copolymer resins of ethylene vinyl acetate (EVA), copolymer resins of ethylene and acrylic acid (EAA), copolymer resins of ethylene and ethyl acrylate (EEA), copolymers of ethylene/methyl methacrylate (EMMA), and the like. The thickness of the adhesion layer 60 is preferably from 2 µm to 7 µm. Making the thickness of the adhesion layer 60 no less than 2 µm enables the effect of fixing the reflective layer 62 onto the conversion layer 14 to be sufficiently exhibited. Furthermore, this also enables the risk of an air layer being formed between the conversion layer 14 and the reflective layer 62 to be suppressed. Were an air layer to be formed between the conversion layer 14 and the reflective layer 62, then there would be concern that multiple reflection of the light emitted from the conversion layer 14 might occur, with the light being repeatedly reflected between the air layer and the conversion layer 14, and between the air layer and the reflective layer 62. Moreover, making the thickness of the adhesion layer 60 no greater than 7 µm enables a reduction in modulation transfer function (MTF) and detective quantum efficiency (DQE) to be suppressed.

The reflective layer 62 covers the entire front surface of the adhesion layer 60. The reflective layer 62 has a function of reflecting light converted by the conversion layer 14. The reflective layer 62 is preferably configured from an organic material. Examples of materials that may be employed for the reflective layer 62 include white PET, $TiO_2$, $Al_2O_3$, foamed white PET, polyester-based high reflectivity sheets, specular reflective aluminum, and the like. The thickness of the reflective layer 62 is preferably from 10 µm to 40 µm.

The bonding layer 64 covers the entire front surface of the reflective layer 62. An end portion of the bonding layer 64 extends as far as the front surface of the TFT substrate 12. Namely, the bonding layer 64 is bonded to the TFT substrate 12 at this end portion. The bonding layer 64 has a function to fix the reflective layer 62 and the protective layer 22 to the conversion layer 14. The same materials as the materials that may be employed as the adhesion layer 60 may also be employed as the material of the bonding layer 64. However, the bonding strength of the bonding layer 64 is preferably greater than the bonding strength of the adhesion layer 60.

The protective layer 22 covers the entire front surface of the bonding layer 64. Namely, the protective layer 22 is provided so as to cover the entirety of the conversion layer 14, and an end portion of the protective layer 22 also covers a portion of the TFT substrate 12. The protective layer 22 functions as a moisture-proof film to prevent the ingress of moisture into the conversion layer 14. Examples of materials that may be employed as the material of the protective layer 22 include organic films containing an organic material such as PET, PPS, OPP, PEN, PI, and the like. Moreover, an ALPET (registered trademark) sheet may be employed as the protective layer 22.

The reinforcement substrate 40 is provided on the front surface of the protective layer 22, with the adhesion layer 48 interposed therebetween. The same materials as the materials that may be employed for the adhesion layer 60 and the adhesion layer 48 may, for example, also be employed as the material of the adhesion layer 48.

Figure 20:
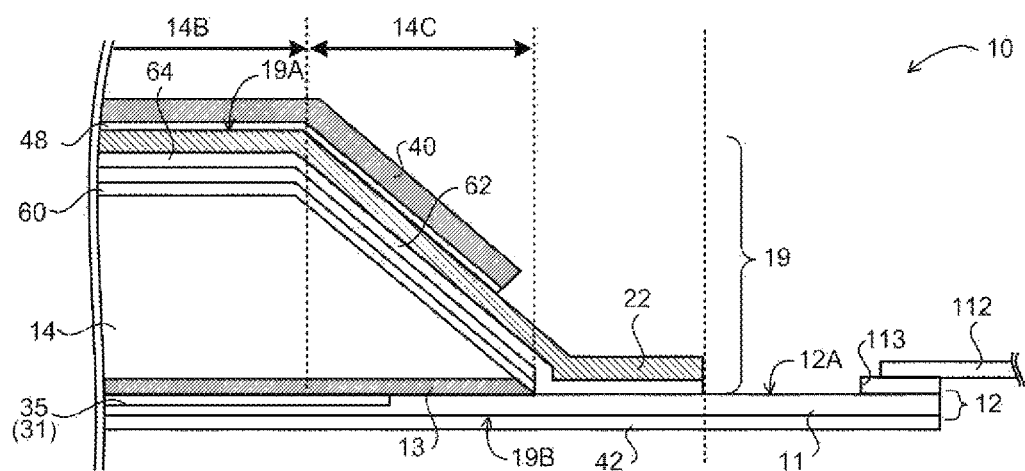
FIG. 20 is a cross-section illustrating an example of configuration of a radiation detector of an exemplary embodiment of technology disclosed herein.

In the example illustrated in FIG. 20, the reinforcement substrate 40 extends over regions corresponding to the central portion 14B and the peripheral edge portion 14C of the conversion layer 14, with an outer peripheral portion of the reinforcement substrate 40 angled so as to follow the slope of the peripheral edge portion 14C of the conversion layer 14. The reinforcement substrate 40 is bonded to the protective layer 22 through the adhesion layer 48 at both the region corresponding to the central portion 14B and the region corresponding to the peripheral edge portion 14C of the conversion layer 14. In the example illustrated in FIG. 20, an end portion of the reinforcement substrate 40 is disposed at the region corresponding to the peripheral edge portion 14C of the conversion layer 14.

Figure 21:
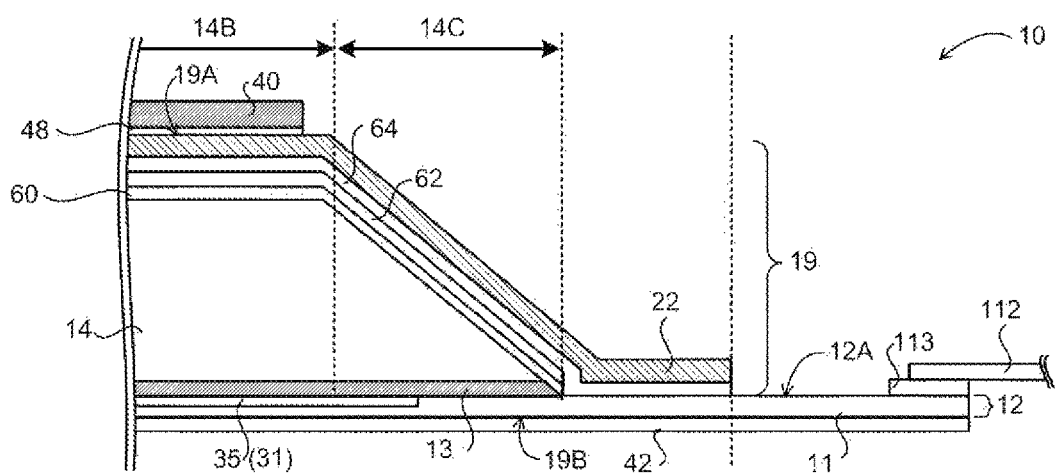
FIG. 21 is a cross-section illustrating an example of configuration of a radiation detector of an exemplary embodiment of technology disclosed herein.

As illustrated in FIG. 21, the reinforcement substrate 40 may be provided only at the region corresponding to the central portion 14B of the conversion layer 14. In such cases, the reinforcement substrate 40 is bonded to the protective layer 22 through the adhesion layer 48 at the region corresponding to the central portion 14B of the conversion layer 14.

Figure 22:
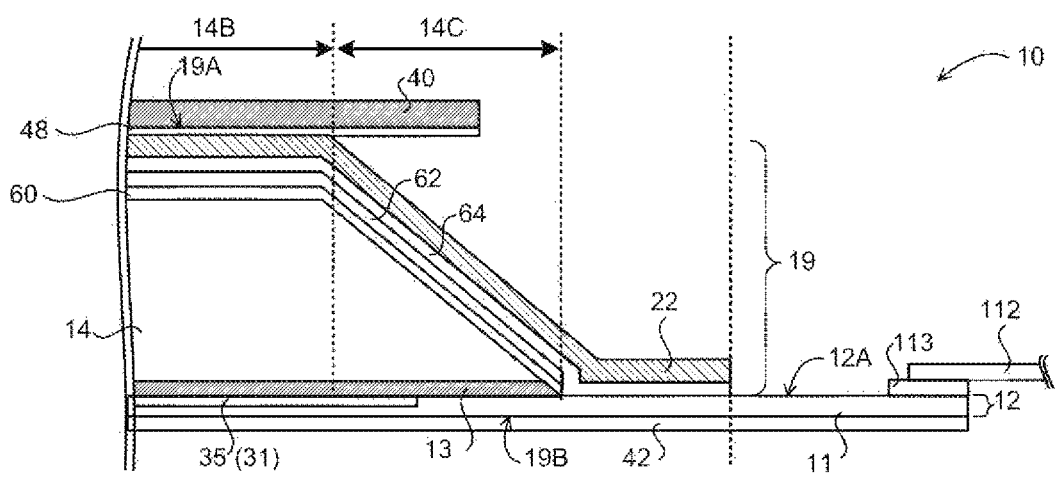
FIG. 22 is a cross-section illustrating an example of configuration of a radiation detector of an exemplary embodiment of technology disclosed herein.

As illustrated in FIG. 22, in cases in which the reinforcement substrate 40 extends over the regions corresponding to both the central portion 14B and the peripheral edge portion 14C of the conversion layer 14, the reinforcement substrate 40 may be configured without providing an angled portion to follow the slope of the outer peripheral portion of the conversion layer 14. In such cases, the reinforcement substrate 40 is bonded to the protective layer 22 through the adhesion layer 48 at the region corresponding to the central portion 14B of the conversion layer 14. A space corresponding to the slope of the peripheral edge portion 14C of the conversion layer 14 is formed between the conversion layer 14 (the protective layer 22) and the reinforcement substrate 40 at the region corresponding to the peripheral edge portion 14C of the conversion layer 14.

Note that the flexible cable 112 is connected to terminals 113 provided in a connection region at the outer peripheral portion of the TFT substrate 12. The TFT substrate 12 is connected to a control board (the control board 110, see FIG. 54, etc.) through the flexible cable 112. There is a concern that the flexible cable 112 might detach from the TFT substrate 12 or positional misalignment might arise when bending of the TFT substrate 12 occurs. In such cases it is necessary to perform a task to reconnect the flexible cable 112 and the TFT substrate 12. This task to reconnect the flexible cable 112 and the TFT substrate 12 is called re-work. As illustrated in FIG. 20 to FIG. 22, by arranging the end portion of the reinforcement substrate 40 at the inner side of the end portion of the conversion layer 14, re-work can be performed more easily than in cases in which the reinforcement substrate 40 extends as far as the vicinity of the connection region.

As illustrated in FIG. 23 to FIG. 26, the end portion of the reinforcement substrate 40 may be disposed at the outer side of the end portion of the conversion layer 14, and may be provided so as to be aligned with the end portions of the bonding layer 64 and the protective layer 22 that both extend over the TFT substrate 12. Note that there is no need for the position of the end portion of the reinforcement substrate 40 to align exactly with the position of the end portions of the bonding layer 64 and the protective layer 22.

Figure 23:
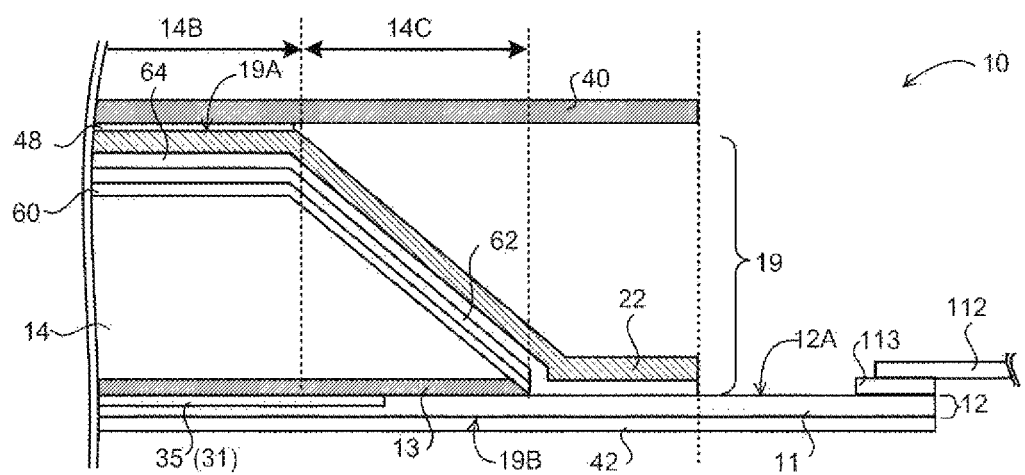
FIG. 23 is a cross-section illustrating an example of configuration of a radiation detector of an exemplary embodiment of technology disclosed herein.

In the example illustrated in FIG. 23, the reinforcement substrate 40 is bonded to the protective layer 22 through the adhesion layer 48 at the region corresponding to the central portion 14B of the conversion layer 14, and a space corresponding to the slope at the peripheral edge portion 14C of the conversion layer 14 is formed between the conversion layer 14 (the protective layer 22) and the reinforcement substrate 40 at the region corresponding to the peripheral edge portion 14C of the conversion layer 14 and also at a region at the outer side thereof.

Figure 24:
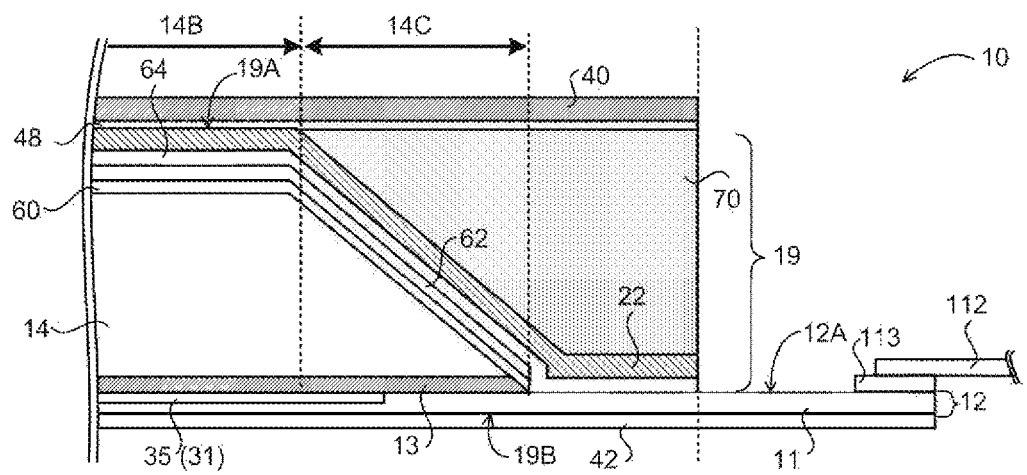
FIG. 24 is a cross-section illustrating an example of configuration of a radiation detector of an exemplary embodiment of technology disclosed herein.

In the example illustrated in FIG. 24, the filler 70 is provided in the space formed between the conversion layer 14 (the protective layer 22) and the reinforcement substrate 40 at the region corresponding to the peripheral edge portion 14C of the conversion layer 14 and also at the region at the outer side thereof. The material of the filler 70 is not particularly limited, and examples of materials that may be employed therefor include resins. Note that in the example illustrated in FIG. 24, the adhesion layer 48 is provided across the entire region between the reinforcement substrate 40 and the filler 70 in order to fix the reinforcement substrate 40 to the filler 70.

The method of forming the filler 70 is not particularly limited. For example, after forming the adhesion layer 48 and the reinforcement substrate 40 in sequence on top of the conversion layer 14 covered by the adhesion layer 60, the reflective layer 62, the bonding layer 64, and the protective layer 22, flowable filler 70 may be poured into the space formed between the conversion layer 14 (the protective layer 22) and the reinforcement substrate 40, and the filler 70 then cured. Alternatively, for example, after forming the conversion layer 14, the adhesion layer 60, the reflective layer 62, the bonding layer 64, and the protective layer 22 in sequence on top of the TFT substrate 12, the filler 70 may be formed, and the adhesion layer 48 and the reinforcement substrate 40 may then be formed in sequence so as to cover the conversion layer 14 covered by the adhesion layer 60, the reflective layer 62, the bonding layer 64, and the protective layer 22, and also cover the filler 70.

By filling the filler 70 into the space formed between the conversion layer 14 (the protective layer 22) and the reinforcement substrate 40 in this manner, the reinforcement substrate 40 can be better suppressed from detaching from the conversion layer 14 (the protective layer 22) than in the embodiment illustrated in FIG. 23. Furthermore, due to adopting a structure in which the conversion layer 14 is fixed to the TFT substrate 12 by both the reinforcement substrate 40 and the filler 70, the conversion layer 14 can be suppressed from detaching from the TFT substrate 12.

Figure 25:
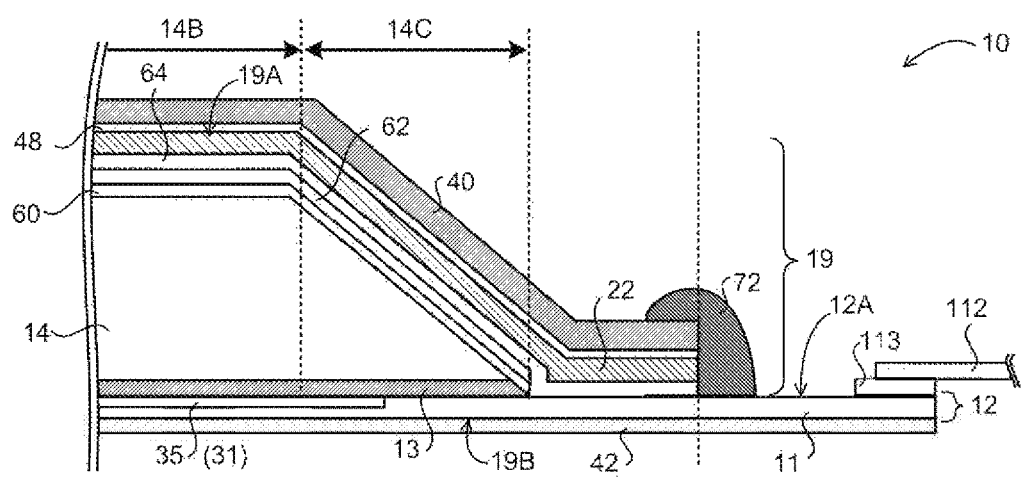
FIG. 25 is a cross-section illustrating an example of configuration of a radiation detector of an exemplary embodiment of technology disclosed herein.

In the example illustrated in FIG. 25, the outer peripheral portion of the reinforcement substrate 40 is angled so as to follow the slope of the peripheral edge portion 14C of the conversion layer 14, and so as also to cover the portions of the bonding layer 64 and the protective layer 22 that cover over the TFT substrate 12. Moreover, the end portion of the reinforcement substrate 40 and the end portions of the bonding layer 64 and the protective layer 22 are aligned with each other. Note that there is no need for the position of the end portion of the reinforcement substrate 40 to align exactly with the position of the end portions of the bonding layer 64 and the protective layer 22.

The end portions of the reinforcement substrate 40, the adhesion layer 48, the protective layer 22, and the bonding layer 64 are sealed with a sealing member 72. The sealing member 72 is preferably provided in a region spanning from the front surface of the TFT substrate 12 to the front surface of the reinforcement substrate 40, and in a region not covering the pixel region 35. Resins may be employed as the material of the sealing member 72, and thermoplastic resins are particularly preferably employed therefor. Specifically, glues such as acrylic glues, urethane based glues, and the like may be employed as the sealing member 72. The reinforcement substrate 40 has a higher rigidity than that of the protective layer 22, and there is a concern that restoring force due to the angle attempting to straighten out at the angled portion of the reinforcement substrate 40 might act to cause the protective layer 22 to detach therefrom. Sealing the end portions of the reinforcement substrate 40, the adhesion layer 48, the protective layer 22, and the bonding layer 64 using the sealing member 72 enables such detachment of the protective layer 22 to be suppressed.

Figure 26:
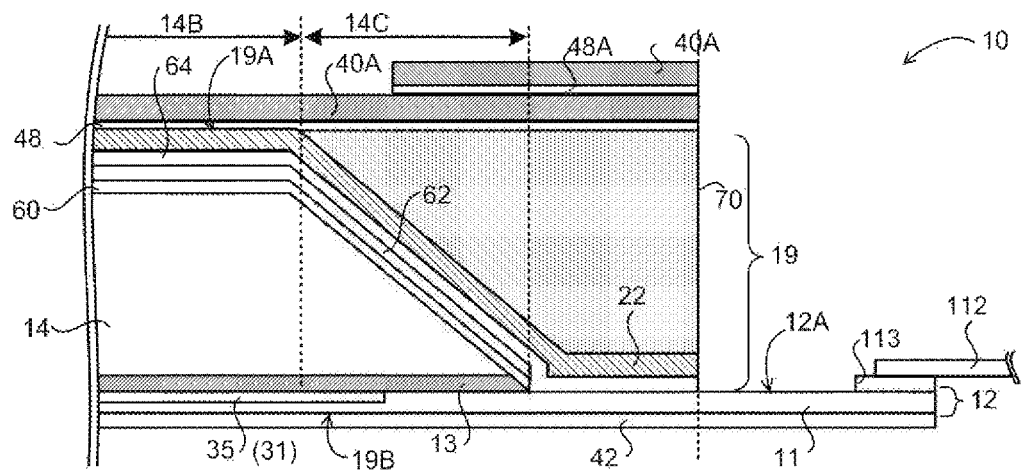
FIG. 26 is a cross-section illustrating an example of configuration of a radiation detector of an exemplary embodiment of technology disclosed herein.

Similarly to in the embodiment illustrated in FIG. 24, in the example illustrated in FIG. 26, the filler 70 is provided in a space formed between the conversion layer 14 (the protective layer 22) and the reinforcement substrate 40 at the region corresponding to the peripheral edge portion 14C of the conversion layer 14 and also at the region at the outer side thereof. Moreover, at the region corresponding to the end portion of the conversion layer 14, an additional and separate reinforcement substrate 40A is stacked on the front surface of the reinforcement substrate 40 with an adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multi-layer structure using the reinforcement substrates 40 and 50A at the region corresponding to the end portion of the conversion layer 14 enables the effect of suppressing bending of the TFT substrate 12 at the end portion of the conversion layer 14 to be enhanced.

As illustrated in FIG. 23 to FIG. 26, in cases in which the end portion of the reinforcement substrate 40 is disposed further to the outer side than the end portion of the conversion layer 14 and is provided so as to be aligned with the end portions of the bonding layer 64 and the protective layer 22, re-work can also be performed more easily than in cases in which the reinforcement substrate 40 extends as far as the vicinity of the connection region.

As illustrated in FIG. 27 to FIG. 30, a configuration may be adopted in which the end portion of the reinforcement substrate 40 is provided so as to be positioned further toward the outer side than the end portions of the bonding layer 64 and the protective layer 22 that extend as far as on top of the TFT substrate 12, and so as to be positioned at the inner side of the end portion of the TFT substrate 12.

Figure 27:
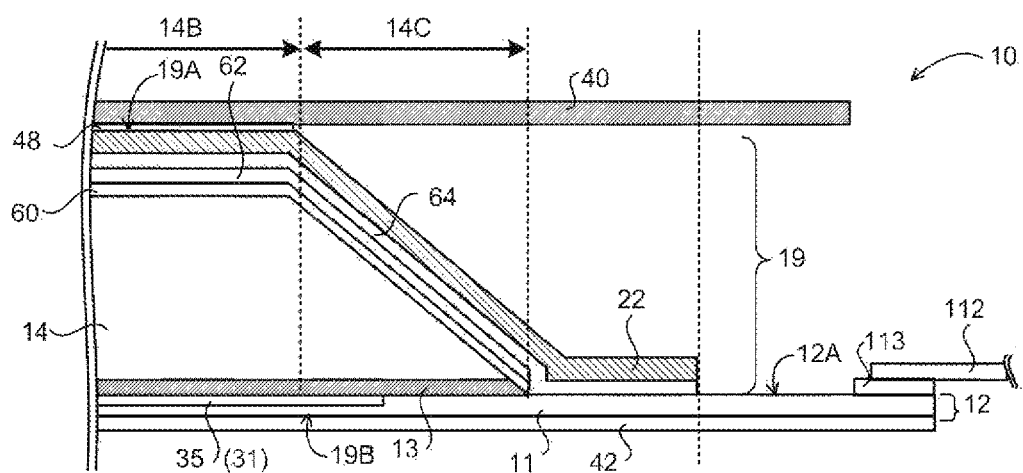
FIG. 27 is a cross-section illustrating an example of configuration of a radiation detector of an exemplary embodiment of technology disclosed herein.

In the example illustrated in FIG. 27, the reinforcement substrate 40 is bonded to the protective layer 22 through the adhesion layer 48 at the region corresponding to the central portion 14B of the conversion layer 14. A space corresponding to the slope of the peripheral edge portion 14C of the conversion layer 14 is formed between the conversion layer 14 (the protective layer 22) and the reinforcement substrate 40, and between the TFT substrate 12 and the reinforcement substrate 40, at the region corresponding to the peripheral edge portion 14C of the conversion layer 14 and also at the region at the outer side thereof.

Figure 28:
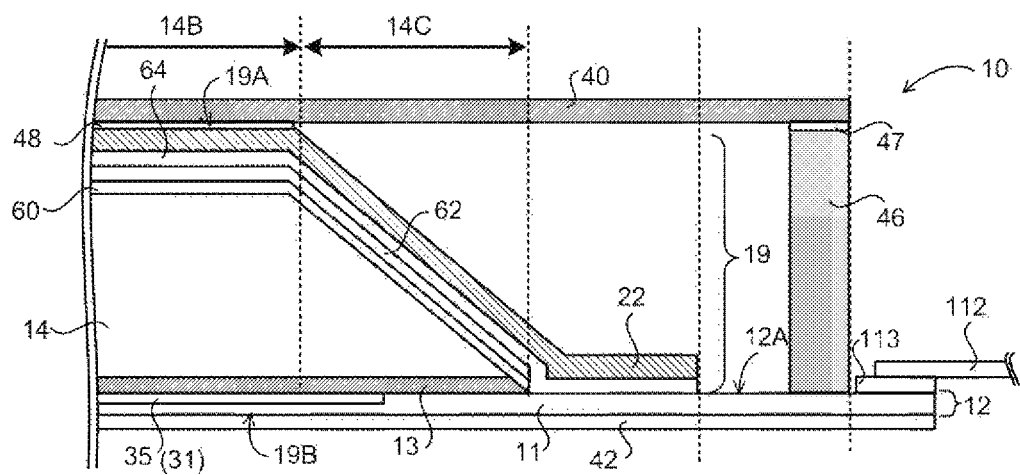
FIG. 28 is a cross-section illustrating an example of configuration of a radiation detector of an exemplary embodiment of technology disclosed herein.

In the example illustrated in FIG. 28, the end portion of the reinforcement substrate 40 is supported by the spacer 46. Namely, one end of the spacer 46 is connected to the second surface 12A of the TFT substrate 12, and the other end of the spacer 46 is connected to the end portion of the reinforcement substrate 40 through a bonding layer 47. By using the spacer 46 to support the end portion of the reinforcement substrate 40 that extends so as to form a space between itself and the TFT substrate 12, detachment of the reinforcement substrate 40 can be suppressed. Moreover, the bending suppression effect from the reinforcement substrate 40 can be caused to act as far as the vicinity of the end portion of the TFT substrate 12. Note that instead of providing the spacer 46, or in addition to providing the spacer 46, a filler may be filled into the space formed between the conversion layer 14 (the protective layer 22) and the reinforcement substrate 40, and between the TFT substrate 12 and the reinforcement substrate 40, in a similar manner to the example illustrated in FIG. 24.

Figure 29:
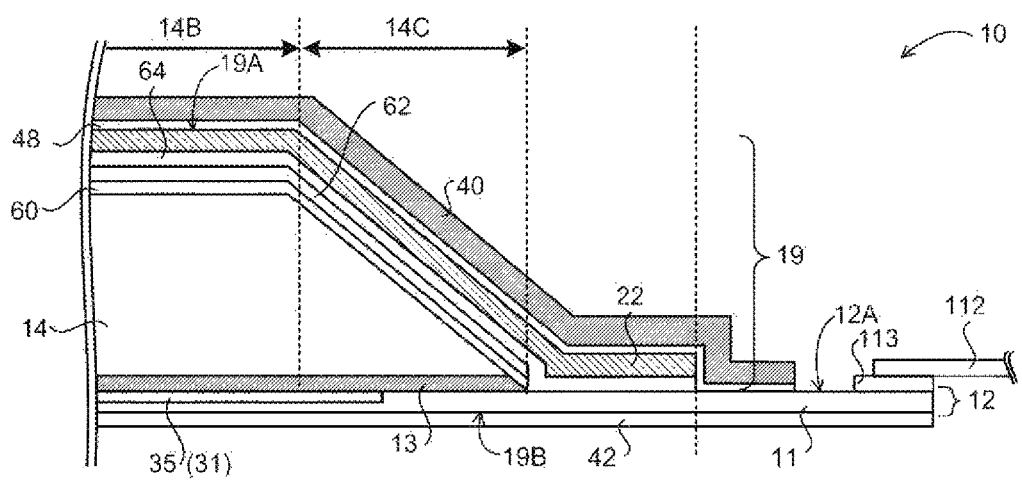
FIG. 29 is a cross-section illustrating an example of configuration of a radiation detector of an exemplary embodiment of technology disclosed herein.

In the example illustrated in FIG. 29, the outer peripheral portion of the reinforcement substrate 40 is angled so as to follow the slope at the peripheral edge portion 14C of the conversion layer 14, and covers the portion where the bonding layer 64 and the protective layer 22 cover over the TFT substrate 12 and also covers over the TFT substrate 12 at the outer side thereof. Namely, the end portions of the bonding layer 64 and the protective layer 22 are sealed by the reinforcement substrate 40. The portion of the reinforcement substrate 40 that extends over the TFT substrate 12 is bonded to the TFT substrate 12 through the adhesion layer 48. By covering the end portions of the bonding layer 64 and the protective layer 22 using the reinforcement substrate 40 in this manner, detachment of the protective layer 22 can be suppressed. Note that the sealing member 72 may be employed to seal the end portion of the reinforcement substrate 40, in a similar manner to the example illustrated in FIG. 25.

Figure 30:
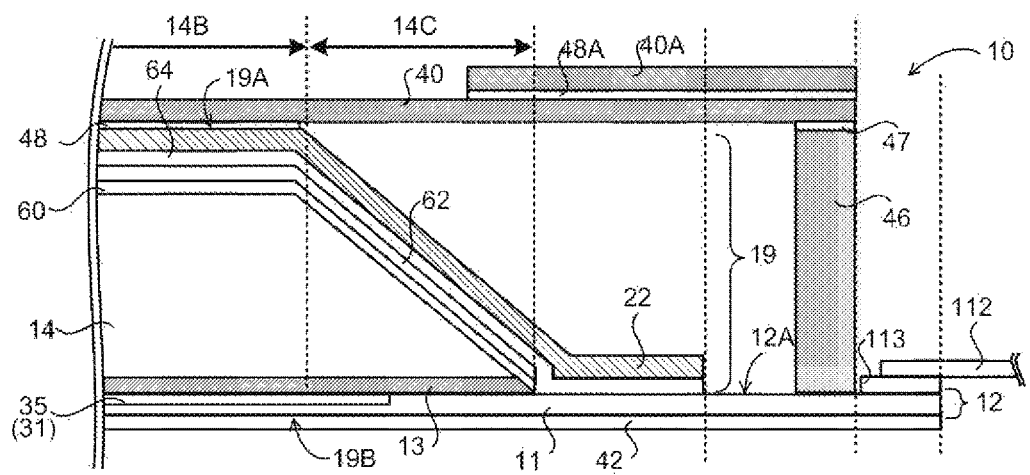
FIG. 30 is a cross-section illustrating an example of configuration of a radiation detector of an exemplary embodiment of technology disclosed herein.

The example illustrated in FIG. 30 is an embodiment in which the end portion of the reinforcement substrate 40 is supported by the spacer 46, and the additional and separate reinforcement substrate 40A is stacked on the front surface of the reinforcement substrate 40 at the region corresponding to the end portion of the conversion layer 14, with the adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multilayer structure using the reinforcement substrates 40 and 50A at the region corresponding to the end portion of the conversion layer 14 enables the effect of suppressing bending of the TFT substrate 12 at the end portion of the conversion layer 14 to be enhanced. Note that instead of providing the spacer 46, the filler 70 may be filled into the space formed between the conversion layer 14 (the protective layer 22) and the reinforcement substrate 40, and between the TFT substrate 12 and the reinforcement substrate 40, in a similar manner to the example illustrated in FIG. 24.

As illustrated in FIG. 31 to FIG. 35, the end portion of the reinforcement substrate 40 may be provided so as to be aligned with the end portion of the TFT substrate 12. Note that there is no need for the position of the end portion of the reinforcement substrate 40 to align exactly with the position of the end portion of the TFT substrate 12.

Figure 31:
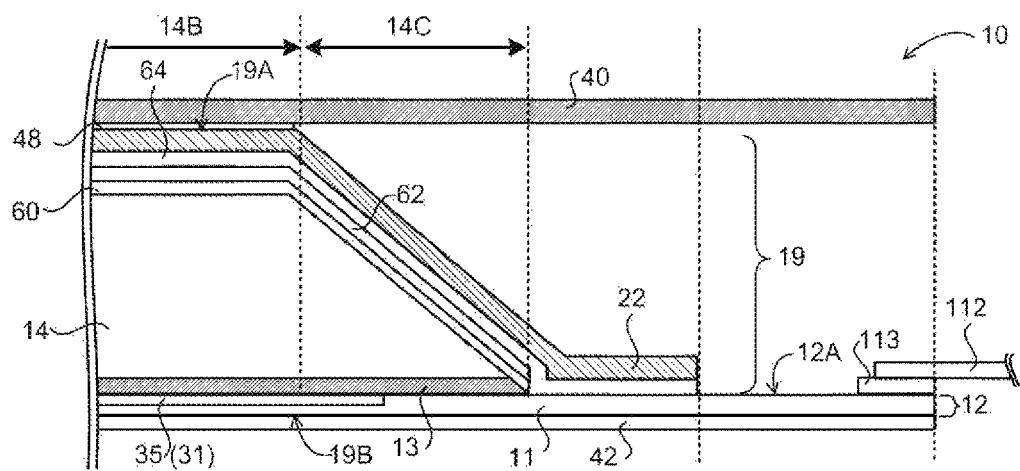
FIG. 31 is a cross-section illustrating an example of configuration of a radiation detector of an exemplary embodiment of technology disclosed herein.

In the example illustrated in FIG. 31, the reinforcement substrate 40 is bonded to the protective layer 22 through the adhesion layer 48 at the region corresponding to the central portion 14B of the conversion layer 14. A space corresponding to the slope of the peripheral edge portion 14C of the conversion layer 14 is formed between the conversion layer 14 (the protective layer 22) and the reinforcement substrate 40, and between the TFT substrate 12 and the reinforcement substrate 40, at the region corresponding to the peripheral edge portion 14C of the conversion layer 14 and also at the region at the outer side thereof.

Figure 32:
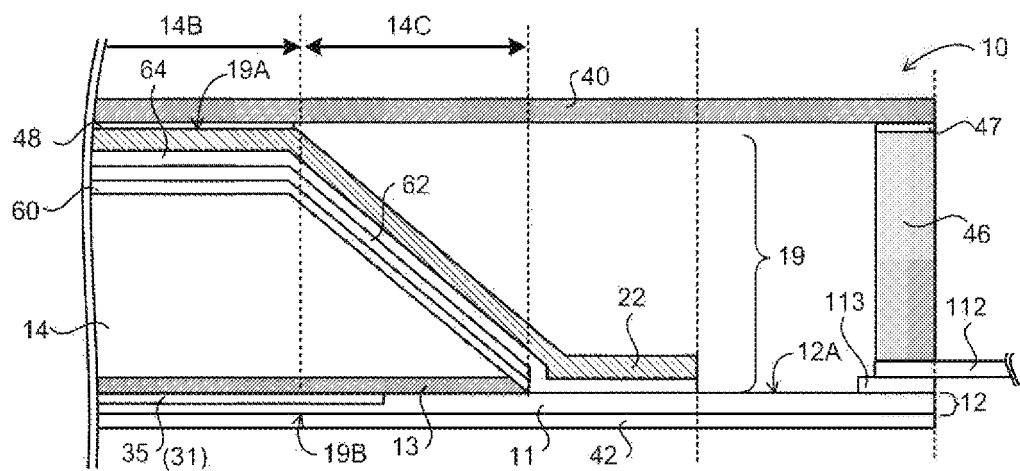
FIG. 32 is a cross-section illustrating an example of configuration of a radiation detector of an exemplary embodiment of technology disclosed herein.

In the example illustrated in FIG. 32, the end portion of the reinforcement substrate 40 is supported by the spacer 46. Namely, one end of the spacer 46 is connected to the flexible cable 112 provided at the end portion of the TFT substrate 12, and the other end of the spacer 46 is connected to the end portion of the reinforcement substrate 40 through the bonding layer 47. By using the spacer 46 to support the end portion of the reinforcement substrate 40 that extends so as to form the space between itself and the TFT substrate 12, detachment of the reinforcement substrate 40 can be suppressed. Moreover, the bending suppression effect from the reinforcement substrate 40 can be caused to act as far as the vicinity of the end portion of the TFT substrate 12.

Figure 33:
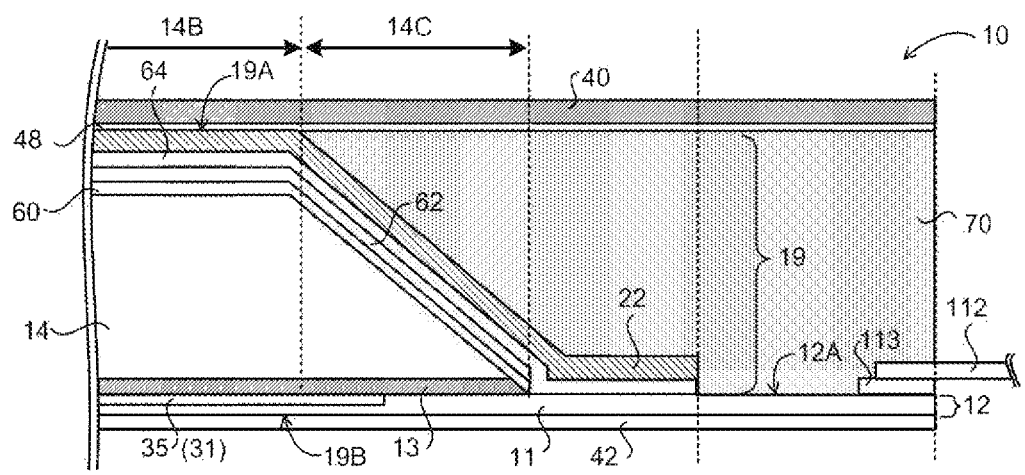
FIG. 33 is a cross-section illustrating an example of configuration of a radiation detector of an exemplary embodiment of technology disclosed herein.

In the example illustrated in FIG. 33, the filler 70 is filled into the space formed between the conversion layer 14 (the protective layer 22) and the reinforcement substrate 40, and between the TFT substrate 12 and the reinforcement substrate 40. In the present exemplary embodiment, the connection portions between the flexible cable 112 and the terminals 113 are covered by the filler 70. By filling the filler 70 into the space formed between the conversion layer 14 (the protective layer 22) and the reinforcement substrate 40 and between the TFT substrate 12 and the reinforcement substrate 40 in this manner, the reinforcement substrate 40 can be better suppressed from detaching from the conversion layer 14 (the protective layer 22) than in the embodiment illustrated in FIG. 31. Furthermore, the structure in which the conversion layer 14 is fixed to the TFT substrate 12 by both the reinforcement substrate 40 and the filler 70 enables the conversion layer 14 to be suppressed from detaching from the TFT substrate 12. Moreover, since the connection portions between the flexible cable 112 and the terminals 113 are covered by the filler 70, detachment of the flexible cable 112 can be suppressed.

Figure 34:
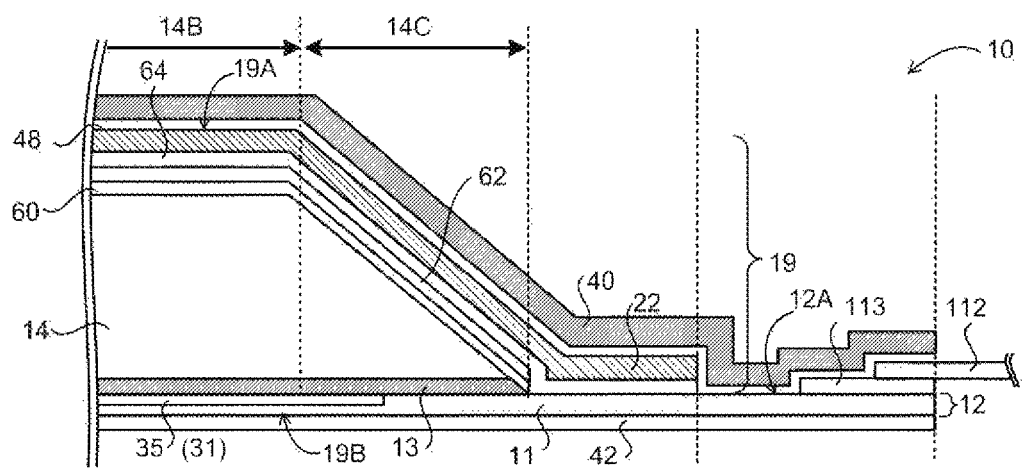
FIG. 34 is a cross-section illustrating an example of configuration of a radiation detector of an exemplary embodiment of technology disclosed herein.

In the example illustrated in FIG. 34, the outer peripheral portion of the reinforcement substrate 40 is angled so as to follow the slope of the peripheral edge portion 14C of the conversion layer 14, and covers a portion where the bonding layer 64 and the protective layer 22 cover over the TFT substrate 12, a portion on top of the substrate at the outer side thereof, and the connection portions between the flexible cable 112 and the terminals 113. The portions of the reinforcement substrate 40 extending over the TFT substrate 12 and over the flexible cable 112 are respectively bonded to the TFT substrate 12 and the flexible cable 112 through the adhesion layer 48. The connection portions between the flexible cable 112 and the terminals 113 are covered by the bent reinforcement substrate 40, enabling detachment of the flexible cable 112 to be suppressed. Moreover, since another end of the flexible cable 112 is anticipated to be connected to a control board mounted with electronic components, there is a concern regarding comparatively large bending of the TFT substrate 12 occurring at the connection portions between the flexible cable 112 and the terminals 113. Since the connection portions between the flexible cable 112 and the terminals 113 are covered by the reinforcement substrate 40, such bending of the TFT substrate 12 at these portions can be suppressed.

Figure 35:
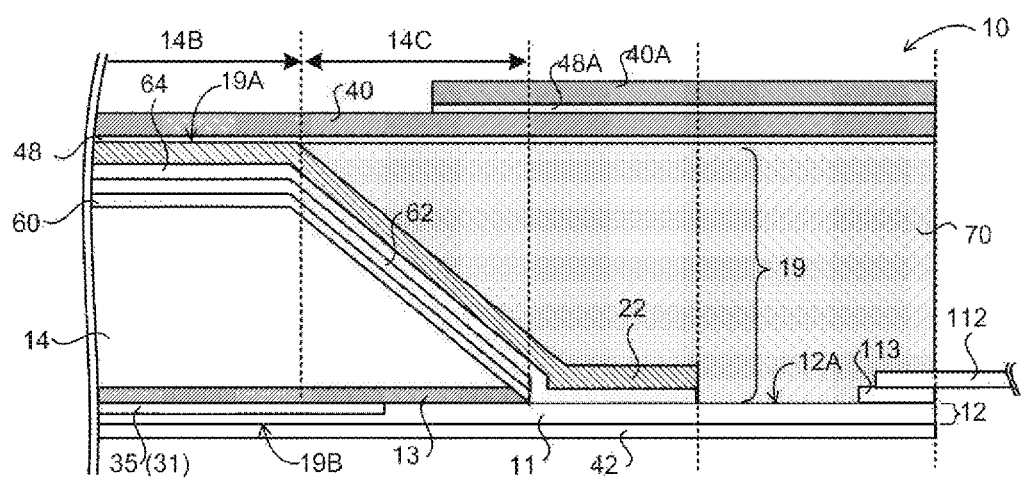
FIG. 35 is a cross-section illustrating an example of configuration of a radiation detector of an exemplary embodiment of technology disclosed herein.

In the example illustrated in FIG. 35, a space formed between the conversion layer 14 (the protective layer 22) and the reinforcement substrate 40, and between the TFT substrate 12 and the reinforcement substrate 40, is filled with the filler 70. Moreover, the additional and separate bending reinforcement substrate 40A is stacked on the front surface of the reinforcement substrate 40 at the region corresponding to the end portion of the conversion layer 14, with the adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multi-layer structure using the reinforcement substrates 40 and 50A at the region corresponding to the end portion of the conversion layer 14 enables the effect of suppressing bending of the TFT substrate 12 to be enhanced at the end portion of the conversion layer 14.

As illustrated in FIG. 36 to FIG. 40, the end portion of the reinforcement substrate 40 may be provided so as to be positioned at the outer side of the end portion of the TFT substrate 12.

Figure 36:
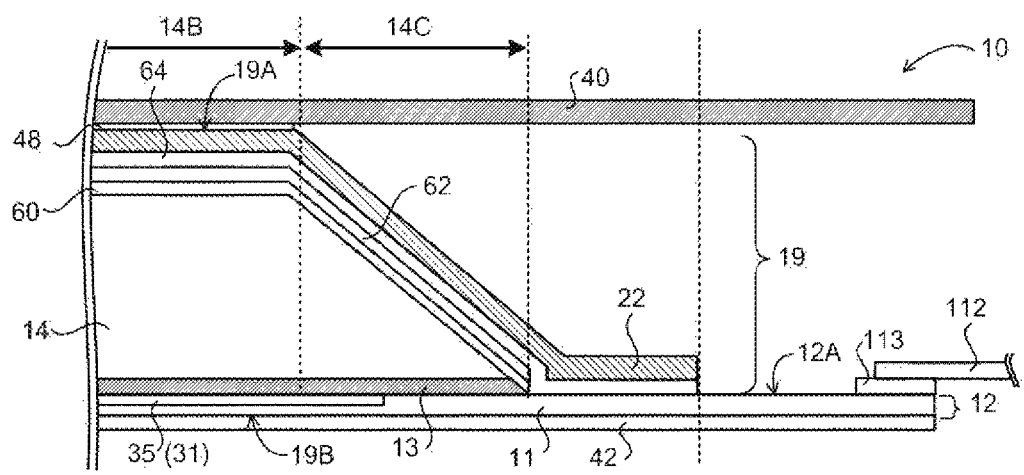
FIG. 36 is a cross-section illustrating an example of configuration of a radiation detector of an exemplary embodiment of technology disclosed herein.

In the example illustrated in FIG. 36, the reinforcement substrate 40 is bonded to the protective layer 22 through the adhesion layer 48 at the region corresponding to the central portion 14B of the conversion layer 14. A space corresponding to the slope of the peripheral edge portion 14C of the conversion layer 14 is formed between the conversion layer 14 (the protective layer 22) and the reinforcement substrate 40, and between the TFT substrate 12 and the reinforcement substrate 40, at the region corresponding to the peripheral edge portion 14C of the conversion layer 14 and also at the region at the outer side thereof.

Figure 37:
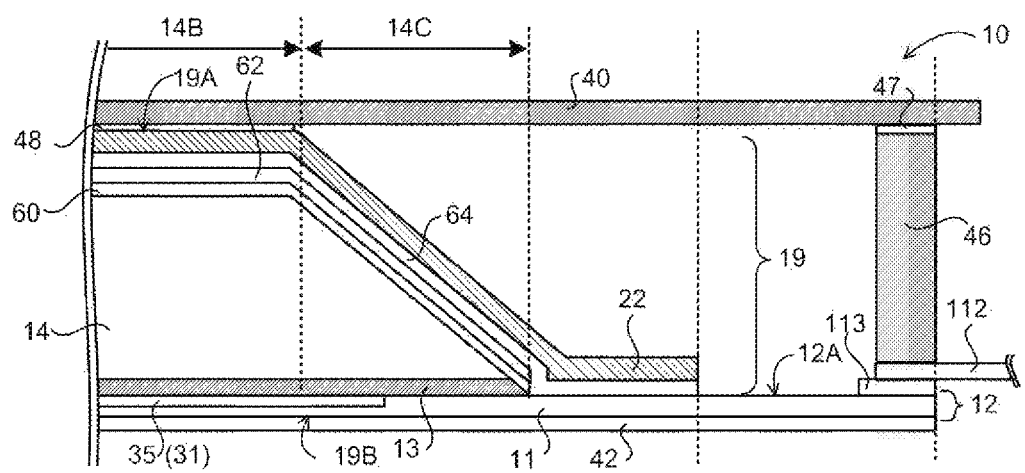
FIG. 37 is a cross-section illustrating an example of configuration of a radiation detector of an exemplary embodiment of technology disclosed herein.

In the example illustrated in FIG. 37, the end portion of the reinforcement substrate 40 is supported by the spacer 46. Namely, one end of the spacer 46 is connected to the flexible cable 112 provided at the end portion of the TFT substrate 12, and the other end of the spacer 46 is connected to the end portion of the reinforcement substrate 40 through the bonding layer 47. By using the spacer 46 to support the end portion of the reinforcement substrate 40 that extends so as to form the space between itself and the TFT substrate 12, detachment of the reinforcement substrate 40 can be suppressed. Moreover, the bending suppression effect from the reinforcement substrate 40 can be caused to act as far as the vicinity of the end portion of the TFT substrate 12.

Figure 38:
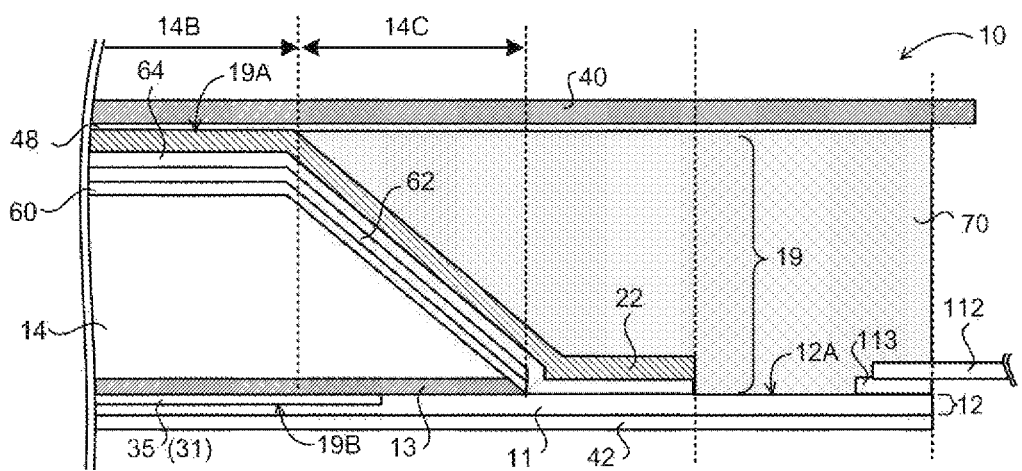
FIG. 38 is a cross-section illustrating an example of configuration of a radiation detector of an exemplary embodiment of technology disclosed herein.

In the example illustrated in FIG. 38, the filler 70 is filled into the space formed between the conversion layer 14 (the protective layer 22) and the reinforcement substrate 40, and between the TFT substrate 12 and the reinforcement substrate 40. In the present exemplary embodiment, the connection portions between the flexible cable 112 and the terminals 113 are covered by the filler 70. By filling the filler 70 into the space formed between the conversion layer 14 (the protective layer 22) and the reinforcement substrate 40 and between the TFT substrate 12 and the reinforcement substrate 40 in this manner, the reinforcement substrate 40 can be better suppressed from detaching from the conversion layer 14 (the protective layer 22) than in the embodiment illustrated in FIG. 36. Furthermore, the structure in which the conversion layer 14 is fixed to the TFT substrate 12 by both the reinforcement substrate 40 and the filler 70 enables the conversion layer 14 to be suppressed from detaching from the TFT substrate 12. Moreover, since the connection portions between the flexible cable 112 and the terminals 113 are covered by the filler 70, detachment of the flexible cable 112 can be suppressed.

Figure 39:
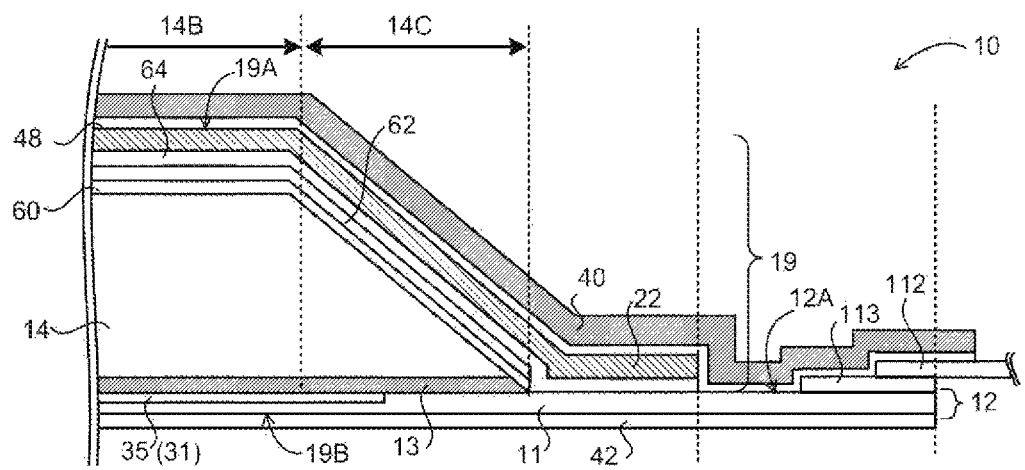
FIG. 39 is a cross-section illustrating an example of configuration of a radiation detector of an exemplary embodiment of technology disclosed herein.

In the example illustrated in FIG. 39, the outer peripheral portion of the reinforcement substrate 40 is angled so as to follow the slope of the peripheral edge portion 14C of the conversion layer 14. The outer peripheral portion of the reinforcement substrate 40 also covers the portion where the bonding layer 64 and the protective layer 22 cover over the TFT substrate 12, the portion on top of the substrate at the outer side thereof, and the connection portions between the terminals 113 and the flexible cable 112. The portions of the reinforcement substrate 40 extending over the TFT substrate 12 and over the flexible cable 112 are respectively bonded to the TFT substrate 12 and the flexible cable 112 through the adhesion layer 48. By covering the connection portions between the flexible cable 112 and the terminals 113 with the reinforcement substrate 40, detachment of the flexible cable 112 can be suppressed. Moreover, since the other end of the flexible cable 112 is anticipated to be connected to a control board mounted with electronic components, there is a concern regarding comparatively large bending of the TFT substrate 12 at the connection portions between the flexible cable 112 and the terminals 113. Since the connection portions between the flexible cable 112 and the terminals 113 are covered by the reinforcement substrate 40, such bending of the TFT substrate 12 at these portions can be suppressed.

Figure 40:
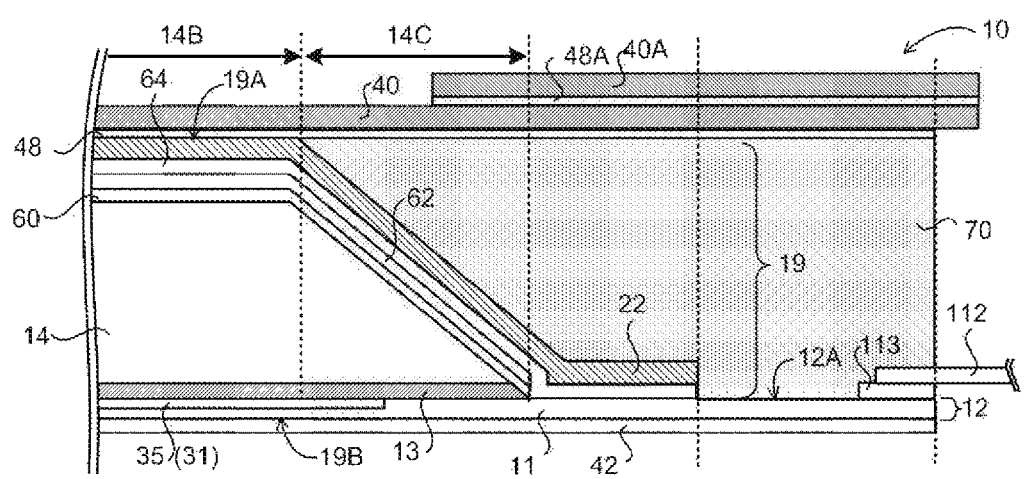
FIG. 40 is a cross-section illustrating an example of configuration of a radiation detector of an exemplary embodiment of technology disclosed herein.
Figure 41:
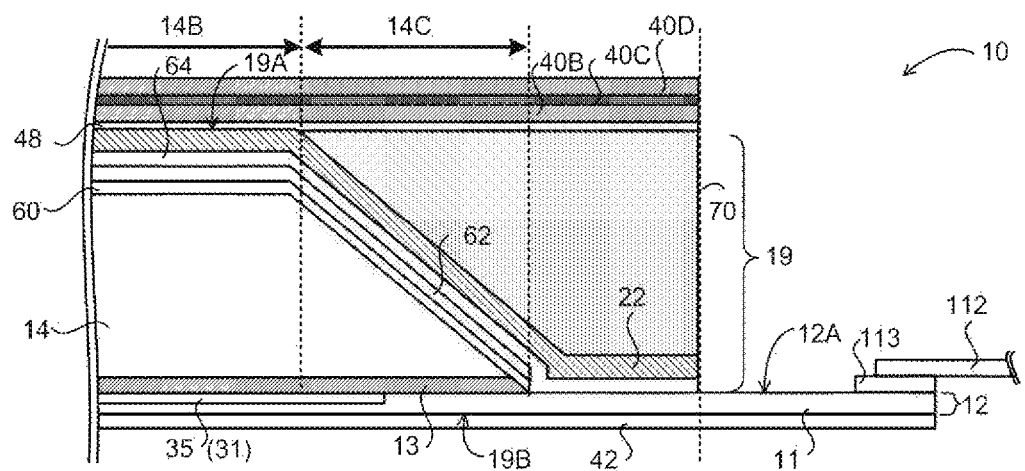
FIG. 41 is a cross-section illustrating an example of configuration of a radiation detector of an exemplary embodiment of technology disclosed herein.

In the example illustrated in FIG. 40, the filler 70 is filled into the space formed between the conversion layer 14 (the protective layer 22) and the reinforcement substrate 40 and between the TFT substrate 12 and the reinforcement substrate 40. Moreover, the additional and separate reinforcement substrate 40A is stacked on the front surface of the reinforcement substrate 40 at the region corresponding to the end portion of the conversion layer 14, with the adhesion layer 48A interposed therebetween. More specifically, the reinforcement substrate 40A is provided at a region straddling the end portion (outer edge, edge) of the conversion layer 14. The reinforcement substrate 40A may be configured from the same materials as the reinforcement substrate 40. In the radiation detector 10, the amount of bending of the TFT substrate 12 is comparatively large at the end portion of the conversion layer 14. Forming a multi-layer structure using the reinforcement substrates 40 and 50A at the region corresponding to the end portion of the conversion layer 14 enables the effect of suppressing bending of the TFT substrate 12 to be enhanced at the end portion of the conversion layer 14.

As described previously, in processes to manufacture the radiation detector 10, the flexible TFT substrate 12 is affixed onto the support body 50, for example a glass substrate, through the separation layer 52. After stacking the conversion layer 14 on top of the TFT substrate 12, the support body 50 is separated from the TFT substrate 12. Bending occurs in the flexible TFT substrate 12 when this is performed, and so there is a concern that the pixels 30 formed on top of the TFT substrate 12 might be damaged thereby. By stacking the reinforcement substrate 40 on top of the conversion layer 14 as in the embodiments illustrated in the examples of FIG. 20 to FIG. 40 prior to separating the support body 50 from the TFT substrate 12, the bending of the TFT substrate 12 that occurs when the support body 50 is being separated from the TFT substrate 12 can be suppressed, enabling the risk of damage to the pixels 30 to be reduced.

Moreover, the reinforcement substrate 40 is not limited to a single layer (one layer), and may be configured with multiple layers. For example, in the radiation detector 10 in the example illustrated in FIG. 41, the reinforcement substrate 40 is a multi-layered film configured of three layers in which a first reinforcement substrate 40B, a second reinforcement substrate 40C, and a third reinforcement substrate 40D are stacked in sequence from the side closest to the conversion layer 14.

In cases in which the reinforcement substrate 40 has multiple layers, each of the layers included in the reinforcement substrate 40 preferably has a different function. For example, in the example illustrated in FIG. 41, the first reinforcement substrate 40B and the third reinforcement substrate 40D may be configured as layers having a non-conductive anti-static function, while the second reinforcement substrate 40C may be configured as a conductive layer such that the reinforcement substrate 40 has an electromagnetic shielding function. In such cases, the first reinforcement substrate 40B and the third reinforcement substrate 40D may employ an anti-static film such as a film employing the anti-static coating COLCOAT (trade name, manufactured by COLCOAT Co., Ltd.). The second reinforcement substrate 40C may employ a conductive sheet, or a conductive mesh sheet made of Cu or the like.

Figure 59:
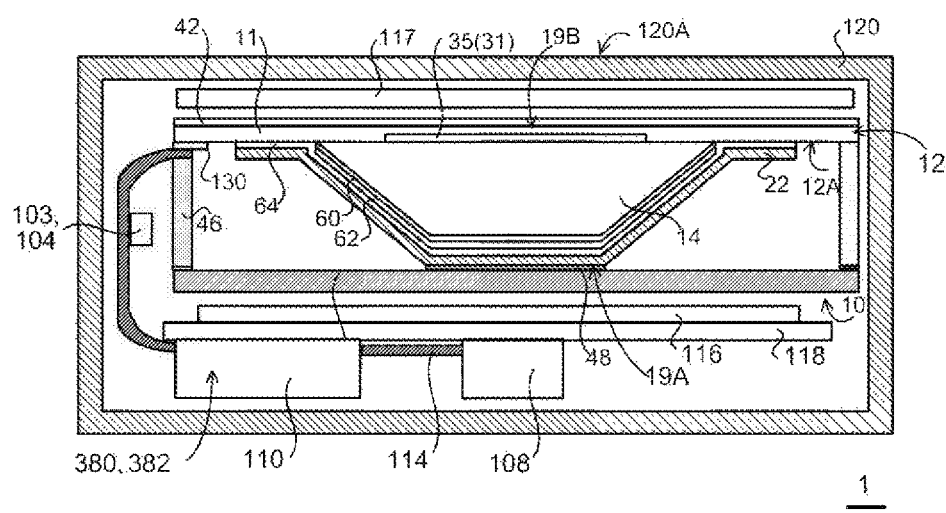
FIG. 59 is a cross-section illustrating an example of configuration of a radiographic imaging device of an exemplary embodiment of technology disclosed herein.

For example, in cases in which the reading approach of the radiation detector 10 is an ISS approach, the control board 110, the power source section 108, and the like may be provided on the conversion layer 14 side (see FIG. 59). Providing the reinforcement substrate 40 with an anti-static function in this manner enables electromagnetic noise from the control board 110 and the power source section 108 to be shielded.

Figure 42:
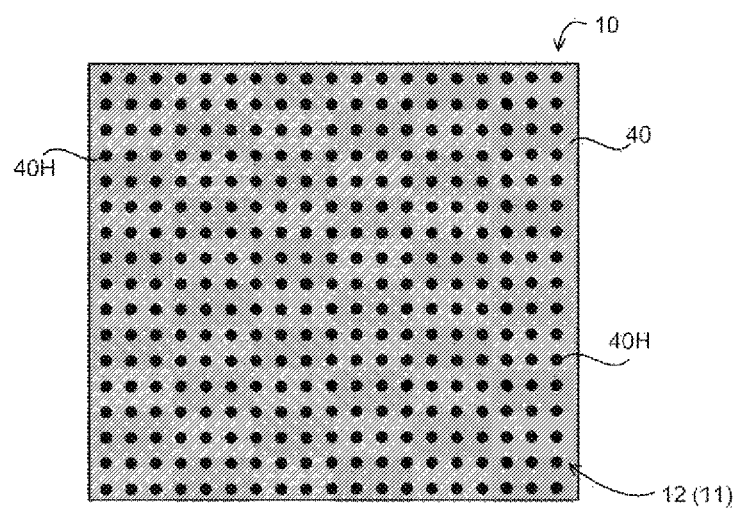
FIG. 42 is a plan view illustrating an example of a structure of a bending suppression member of an exemplary embodiment of technology disclosed herein.

FIG. 42 is a plan view illustrating an example of a structure of the reinforcement substrate 40. A main face of the reinforcement substrate 40 may include plural through holes 40H. The size and pitch of the through holes 40H is prescribed so as to obtain the desired rigidity of the reinforcement substrate 40.

Including the plural through holes 40H in the reinforcement substrate 40 enables air introduced at the joining face of the reinforcement substrate 40 to the conversion layer 14 to escape through the through holes 40H. This enables air bubbles to be suppressed from being generated at the joining face of the reinforcement substrate 40 to the conversion layer 14.

There is a concern that air bubbles might be generated at the joining face of the reinforcement substrate 40 to the conversion layer 3 if no mechanism is provided to allow air introduced at the joining face to escape. For example, were air bubbles generated at the joining face to expand due to heat during operation of the radiographic imaging device 1, there would be a drop in the cohesion between the reinforcement substrate 40 and the conversion layer 14. This would lead to a concern that the bending suppression effect from the reinforcement substrate 40 might not be sufficiently exhibited. By employing the reinforcement substrate 40 including the plural through holes 50A as illustrated in FIG. 42, the generation of air bubbles at the joining face of the reinforcement substrate 40 to the conversion layer 14 can be suppressed as described above, enabling the cohesion between the reinforcement substrate 40 and the conversion layer 14 to be maintained. This enables the bending suppression effect from the reinforcement substrate 40 to be maintained.

Figure 43:
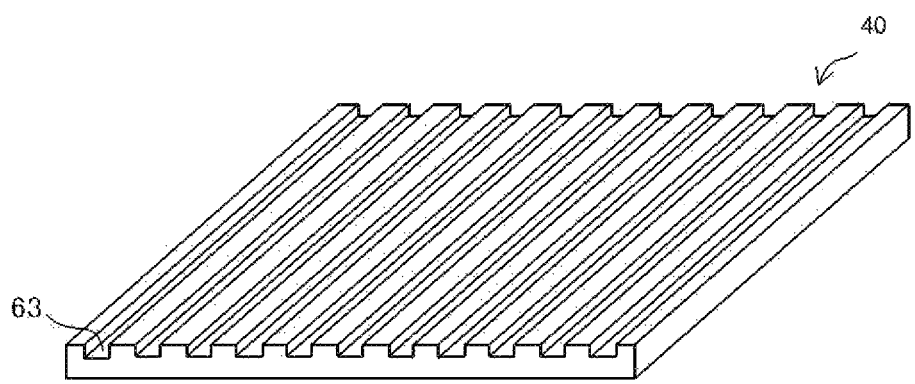
FIG. 43 is a perspective view illustrating an example of a structure of a bending suppression member of an exemplary embodiment of technology disclosed herein.
Figure 44:
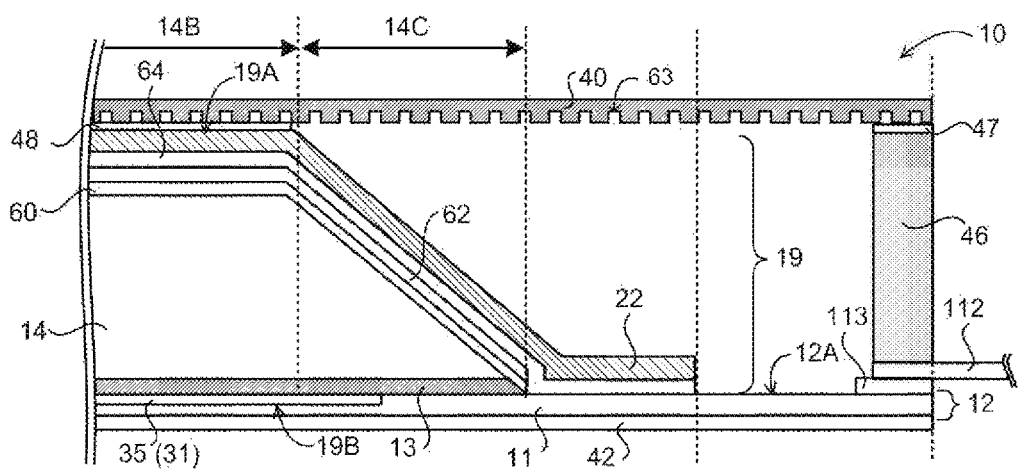
FIG. 44 is a cross-section illustrating an example of configuration of a radiation detector of an exemplary embodiment of technology disclosed herein.

FIG. 43 is a perspective view illustrating another example of the structure of the reinforcement substrate 40. In the example illustrated in FIG. 43, the reinforcement substrate 40 includes an indented-and-protruding structure on the joining face to the conversion layer 14. The indented-and-protruding structure may be configured including plural grooves 63 arranged parallel to each other, as illustrated in FIG. 43. The surface of the reinforcement substrate 40 that includes the indented-and-protruding structure configured from the plural grooves 63 is, for example as illustrated in FIG. 44, joined to the conversion layer 14 that has been covered by the reflective layer 62. Due to the reinforcement substrate 40 including the indented-and-protruding structure on the joining face to the conversion layer 14 in this manner, any air introduced to the joining portion of the reinforcement substrate 40 and the conversion layer 14 is able to escape through the grooves 63. Similarly to in the embodiment illustrated in FIG. 42, this accordingly enables the generation of air bubbles at the joining face of the reinforcement substrate 40 to the conversion layer 14 to be suppressed. This enables the cohesion between the reinforcement substrate 40 and the conversion layer 14 to be maintained, and enables the bending suppression effect from the reinforcement substrate 40 to be maintained.

Figure 45:
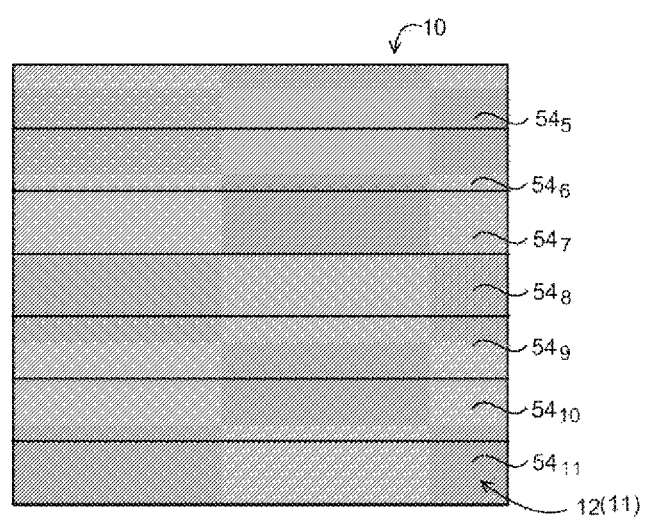
FIG. 45 is a plan view illustrating an example of a structure of a bending suppression member of an exemplary embodiment of technology disclosed herein.
Figure 46:
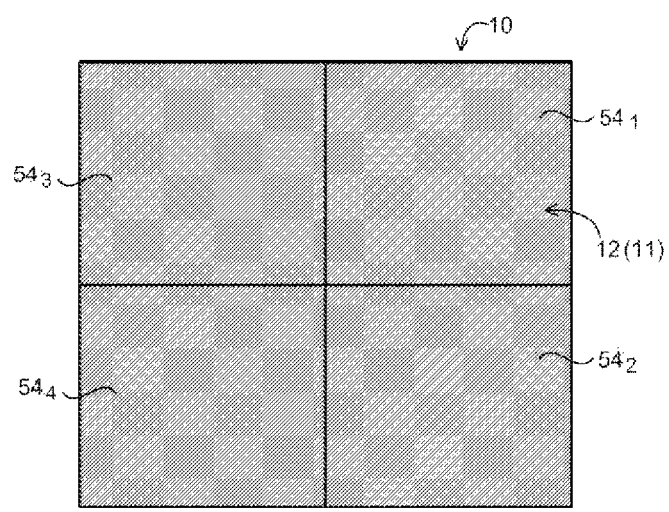
FIG. 46 is a plan view illustrating an example of a structure of a bending suppression member of an exemplary embodiment of technology disclosed herein.

FIG. 45 and FIG. 46 are plan views illustrating other examples of structures of the reinforcement substrate 40. As illustrated in FIG. 45 and FIG. 46, the reinforcement substrate 40 may be segmented into plural pieces 54. The reinforcement substrate 40 may, as illustrated in FIG. 45, be segmented into the plural pieces 54 (FIGS. $54_5$ to $54_{11}$) arrayed along one direction. Alternatively, the reinforcement substrate 40 may, as illustrated in FIG. 46, be segmented into the plural pieces 54 (FIGS. $54_1$ to $54_4$) arrayed in both a longitudinal direction and a lateral direction.

The greater the surface area of the reinforcement substrate 40, the more readily air bubbles are generated at the joining face of the reinforcement substrate 40 to the conversion layer 14. As illustrated in FIG. 45 and FIG. 46, segmenting the reinforcement substrate 40 into the plural pieces 54 enables the generation of air bubbles at the joining face of the reinforcement substrate 40 to the conversion layer 14 to be suppressed. This enables the cohesion between the reinforcement substrate 40 and the conversion layer 14 to be maintained, and thereby enables the bending suppression effect from the reinforcement substrate 40 to be maintained.

A reinforcement member 53 may be provided on the opposite side of the reinforcement substrate 41 to the side contacting the TFT substrate 12 (the second surface 19B). FIG. 47 to FIG. 51 are cross-sections respectively illustrating examples of embodiments of installation of the reinforcement member 53.

In the examples illustrated in FIG. 47 to FIG. 51, the reinforcement member 53 is stacked on an opposite-side surface of the reinforcement substrate 41 to the surface on the TFT substrate 12 side, with a bonding layer 51 interposed therebetween. The reinforcement member 53 may be configured from the same materials as the reinforcement substrate 40. In cases in which the radiation detector 10 employs an ISS approach, the reinforcement member 53 is preferably provided only at an outer peripheral portion of the TFT substrate 12 so as to keep the surface area of locations where the reinforcement member 53 and the pixel region 35 overlap each other as small as possible. Namely, the reinforcement member 53 may have a ring shape with an opening 61 at a location corresponding to the pixel region 35, as illustrated in FIG. 47 to FIG. 51. Forming a multi-layer structure with the reinforcement substrate 41 and the reinforcement member 53 at the outer peripheral portion of the TFT substrate 12 in this manner enables the rigidity of the outer peripheral portion of the TFT substrate 12 that is comparatively susceptible to bending to be reinforced.

Figure 47:
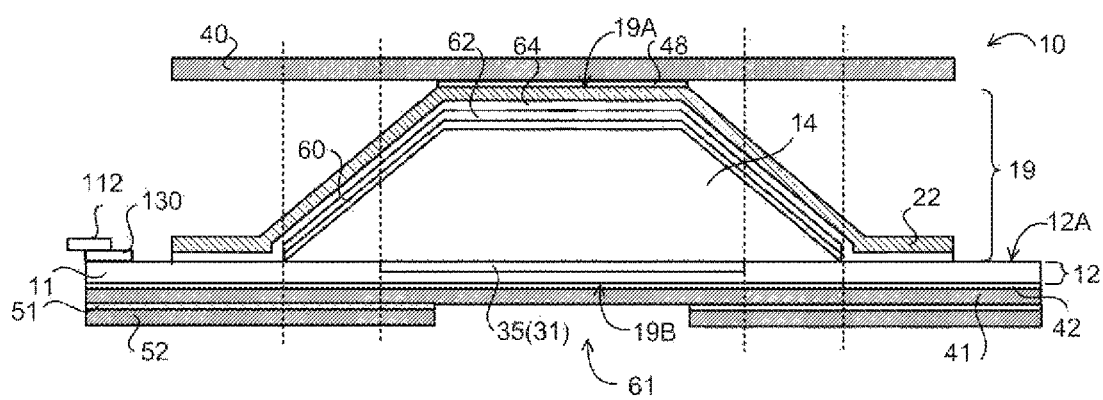
FIG. 47 is a cross-section illustrating an example of configuration of a radiation detector of an exemplary embodiment of technology disclosed herein.
Figure 48:
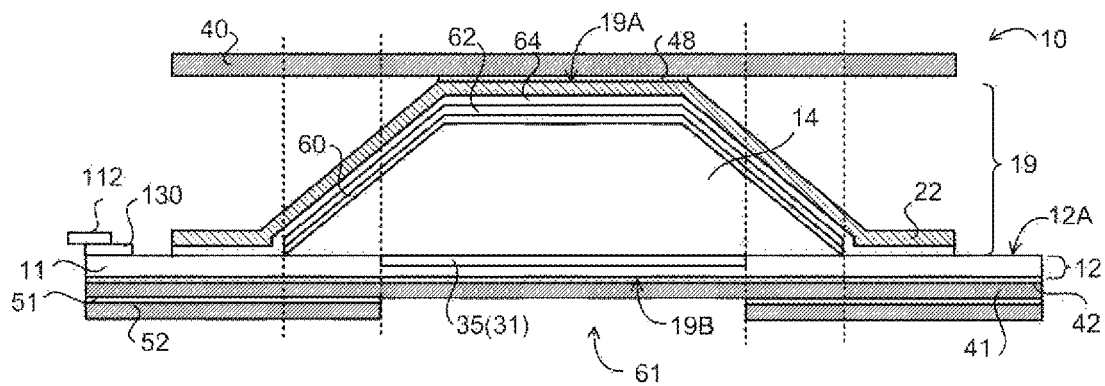
FIG. 48 is a cross-section illustrating an example of configuration of a radiation detector of an exemplary embodiment of technology disclosed herein.
Figure 49:
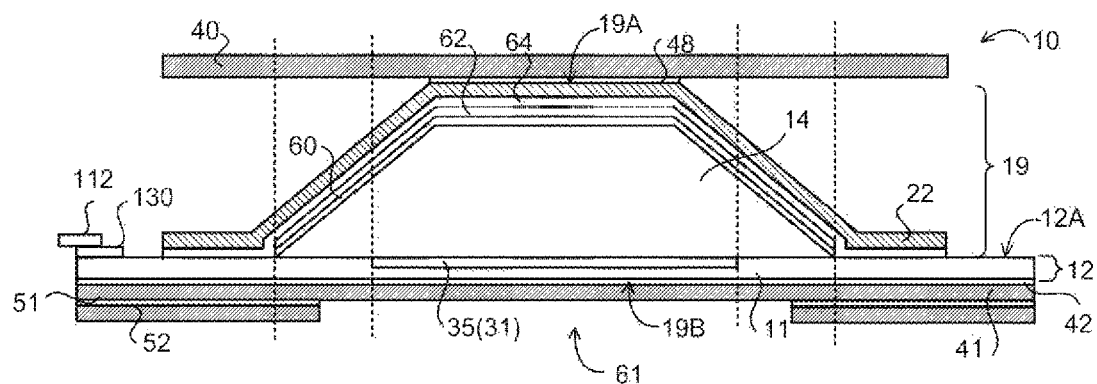
FIG. 49 is a cross-section illustrating an example of configuration of a radiation detector of an exemplary embodiment of technology disclosed herein.

In the examples illustrated in FIG. 47 to FIG. 49, the reinforcement member 53 is provided at a region straddling the end portion (outer edge, edge) of the conversion layer 14. In the radiation detector 10, the amount of bending of the TFT substrate 12 is comparatively large at the end portion of the conversion layer 14. Forming a multi-layer structure using the reinforcement substrate 41 and the reinforcement member 53 at the region corresponding to the end portion of the conversion layer 14 enables the effect of suppressing bending of the TFT substrate 12 to be enhanced at the end portion of the conversion layer 14.

In cases in which an ISS approach is employed in the radiation detector 10, there is a concern that were a portion of the reinforcement member 53 to overlap with the pixel region 35 as illustrated in FIG. 47, this might have an impact on the images, depending on the material employed in the reinforcement member 53. Thus, in cases in which a portion of the reinforcement member 53 overlaps with the pixel region 35, a plastic is preferably employed for the material of the reinforcement member 53.

As illustrated in FIG. 48 and FIG. 49, an embodiment is most preferably adopted in which the reinforcement member 53 straddles the end portion (outer edge, edge) of the conversion layer 14 but does not overlap with the pixel region 35 (namely, an embodiment in which an edge of the opening 61 in the reinforcement member 53 is disposed at the outer side of the pixel region 35). In the example illustrated in FIG. 48, the position of the edge of the opening 61 in the reinforcement member 53 is substantially aligned with the position of the end portion of the pixel region 35. In the example illustrated in FIG. 49, the edge of the opening 61 in the reinforcement member 53 is disposed between the end portion of the pixel region 35 and the end portion of the conversion layer 14.

Figure 50:
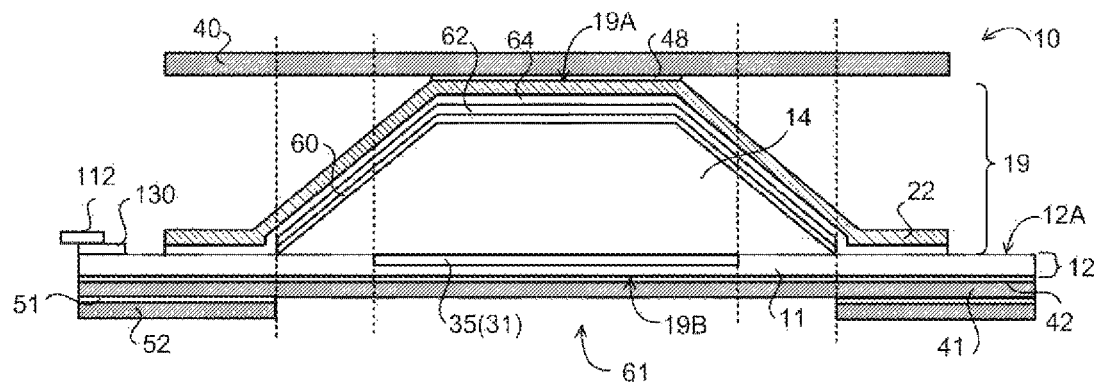
FIG. 50 is a cross-section illustrating an example of configuration of a radiation detector of an exemplary embodiment of technology disclosed herein.
Figure 51:
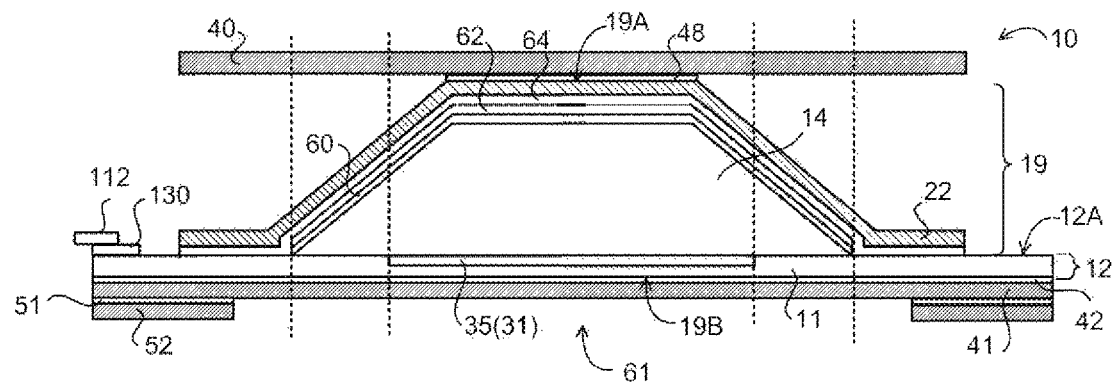
FIG. 51 is a cross-section illustrating an example of configuration of a radiation detector of an exemplary embodiment of technology disclosed herein.

Moreover, the position of the edge of the opening 61 in the reinforcement member 53 may be disposed so as to be substantially aligned with the position of the end portion of the conversion layer 14 as illustrated in FIG. 50, or may be disposed so as to be further toward the outer side than the end portion of the conversion layer 14 as illustrated in FIG. 51. In such cases, there is no structure present where the reinforcement member 53 straddles the end portion (outer edge, edge) of the conversion layer 14, and so there might be a concern regarding a lessening of the effect of suppressing bending of the TFT substrate 12 at the end portion of the conversion layer 14. However, due to forming a stacked structure using the reinforcement substrate 41 and the reinforcement member 53 at the outer peripheral portion of the TFT substrate 12 where the connection portions between the flexible cable 112 and the terminals 113 are present, the effect of suppressing bending of the TFT substrate 12 at the connection portions between the flexible cable 112 and the terminals 113 is maintained.

In the radiation detectors 10 of the exemplary embodiments described above, explanation has been given regarding embodiments in which the size of the TFT substrate 12 (base member 11) and the size of the reinforcement substrate 41 are the same as each other. However, the size of the TFT substrate 12 and the size of the reinforcement substrate 41 may be different to each other.

For example, when the radiation detector 10 is applied to the radiographic imaging device 1, the radiation detector 10 may be employed fixed to the case 120 (see FIG. 7, etc.) or the like that houses the radiation detector 10. In such cases, as in the example illustrated in FIG. 52A, the reinforcement substrate 41 may be made larger than the TFT substrate 12 and provided with a flap or the like in order to fix the radiation detector 10 using the location of the flap or the like. For example, an embodiment may be configured in which holes are provided in a flap portion of the reinforcement substrate 41, and screws are passed through the holes to fix the reinforcement substrate 41 to the case 120 (see FIG. 7, etc.).

Figure 52A:
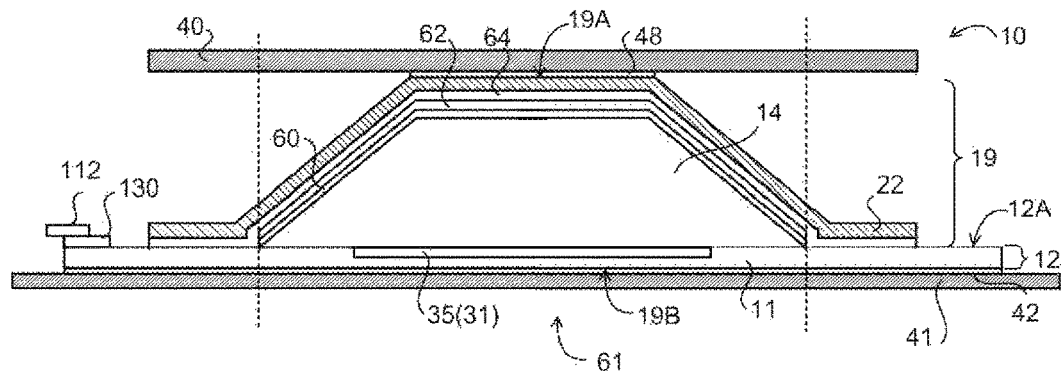
FIG. 52A is a cross-section illustrating an example of configuration of a radiation detector of an exemplary embodiment of technology disclosed herein.
Figure 52B:
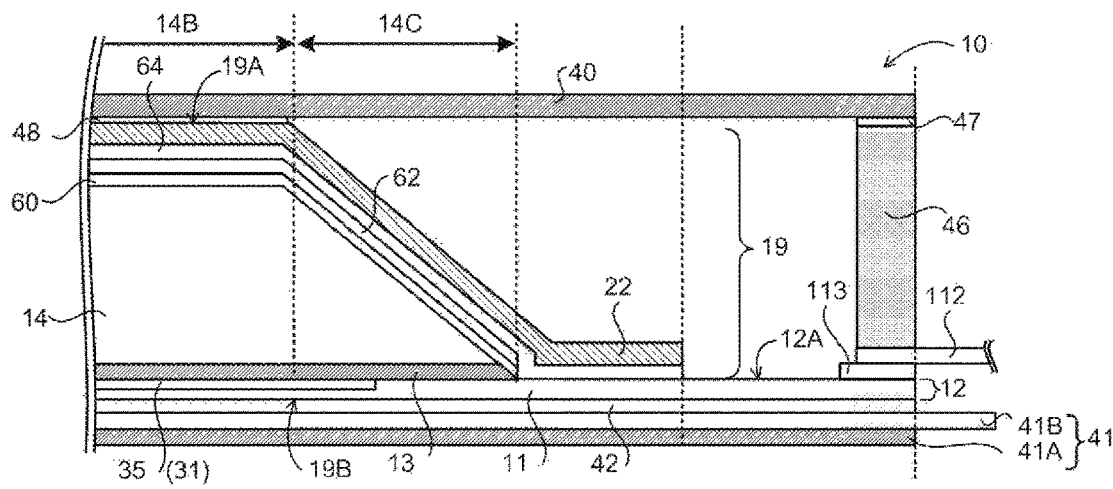
FIG. 52B is a cross-section illustrating an example of configuration of a radiation detector of an exemplary embodiment of technology disclosed herein.

Note that embodiments in which the reinforcement substrate 41 is larger than the TFT substrate 12 are not limited to the embodiment illustrated in FIG. 52A. An embodiment may be configured in which the reinforcement substrate 41 is configured with plural stacked layers, with some of these layers being larger than the TFT substrate 12. For example, as illustrated in FIG. 52B, the reinforcement substrate 41 may be configured with a dual-layer structure including a first layer 41A of similar size to the TFT substrate 12 (the base member 11) and a second layer 41B that is larger than the TFT substrate 12. The first layer 41A is affixed to the second layer 41B using double-sided tape, an adhesion layer, or the like (not illustrated in the drawings). For example, the first layer 41A is preferably formed of similar materials to those of the reinforcement substrate 41 described above so as to possess similar properties to the reinforcement substrate 41. The second layer 41B is affixed to the second surface 19B of the base member 11 using double-sided tape, an adhesion layer, or the like (not illustrated in the drawings). For example, ALPET (registered trademark) may be applied as the second layer 41B. In cases in which the reinforcement substrate 41 is configured with plural layers, conversely to the embodiment illustrated in FIG. 52B, an embodiment may be configured in which the first layer 41A is affixed to the second surface 19B of the base member 11, as illustrated in FIG. 52C.

As described above, in cases in which the radiation detector 10 is fixed to the case 120 (see FIG. 7, etc.) or the like using a flap or the like provided to the reinforcement substrate 41, such fixing may be performed in a state in which the flap portion is bent. The thinner the thickness thereof, the more easily the flap portion of the reinforcement substrate 41 will bend, enabling the flap portion alone to be bent without affecting the main body of the radiation detector 10. Accordingly, in cases in which the flap portion or the like is to be bent, an embodiment in which the reinforcement substrate 41 is configured of plural stacked layers with some of these layers being configured larger than the TFT substrate 12 as illustrated in the examples of FIG. 52B and FIG. 52C is preferable.

Figure 52C:
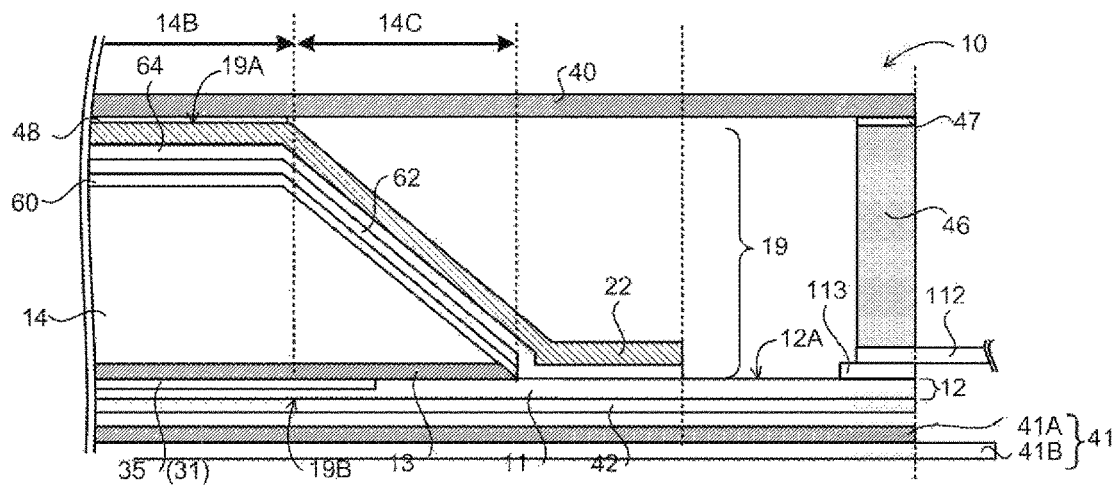
FIG. 52C is a cross-section illustrating an example of configuration of a radiation detector of an exemplary embodiment of technology disclosed herein.
Figure 53:
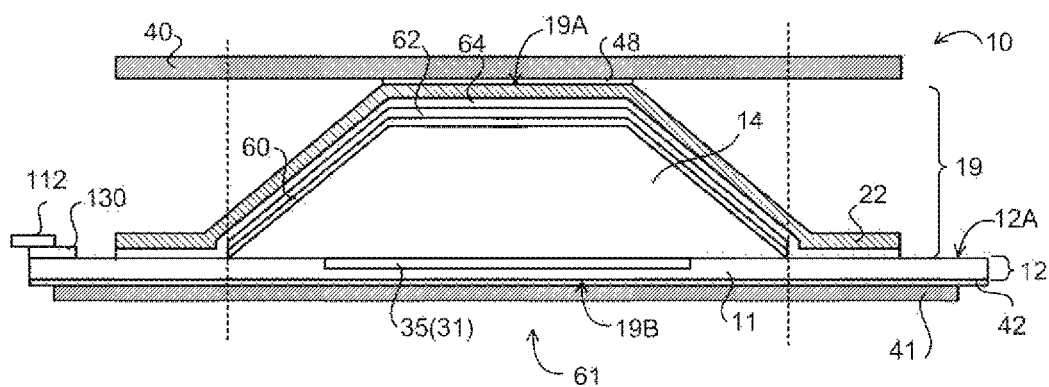
FIG. 53 is a cross-section illustrating an example of configuration of a radiation detector of an exemplary embodiment of technology disclosed herein.

As in the example illustrated in FIG. 53, conversely to the radiation detectors 10 in FIG. 52A to FIG. 52C, the reinforcement substrate 41 may be smaller than the TFT substrate 12. Positioning an end portion of the TFT substrate 12 at the outer side of an end portion of the reinforcement substrate 41 facilitates checking of the position of the end portion of the TFT substrate 12 during assembly, for example when housing the radiation detector 10 inside the case 120 (see FIG. 7, etc.), thus enabling positioning precision to be improved. Note that there is no limitation to the embodiment illustrated in FIG. 53, since as long as at least a portion of the end portion of the TFT substrate 12 (the base member 11) is positioned at the outer side of the reinforcement substrate 41, similar advantageous effects can be obtained and is therefore preferable Explanation follows regarding examples of the radiographic imaging device 1 in which the radiation detector 10 is housed inside the case 120, with reference to FIG. 54 to FIG. 60. FIG. 54 to FIG. 60 are diagrams illustrating other configuration examples of the radiographic imaging device 1.

Figure 54:
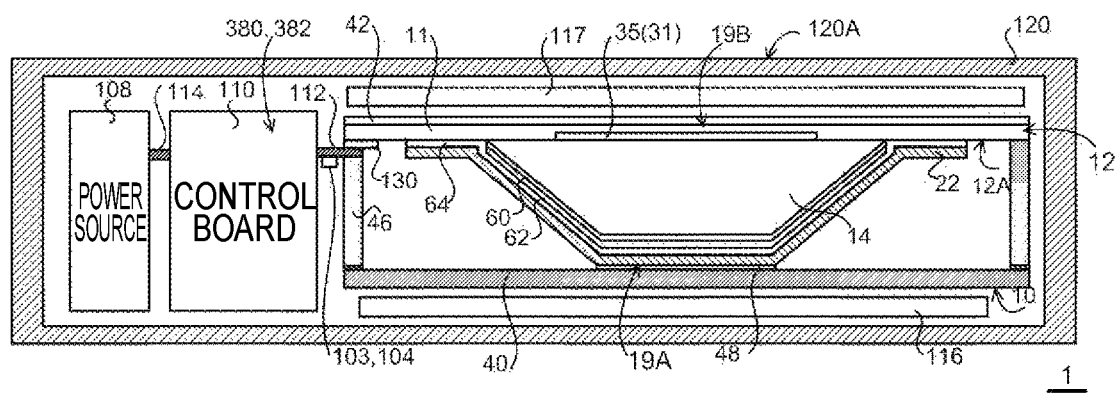
FIG. 54 is a cross-section illustrating an example of configuration of a radiographic imaging device of an exemplary embodiment of technology disclosed herein.
Figure 55:
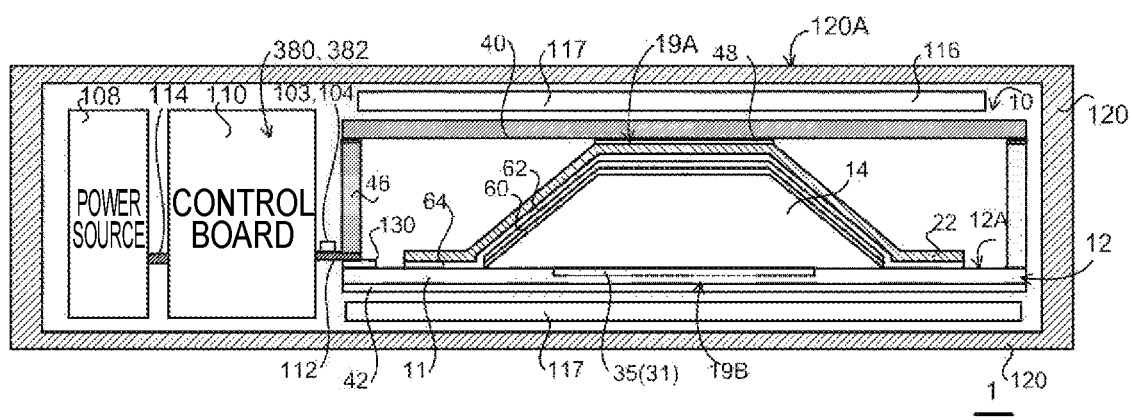
FIG. 55 is a cross-section illustrating an example of configuration of a radiographic imaging device of an exemplary embodiment of technology disclosed herein.

The example illustrated in FIG. 54 is a radiographic imaging device 1 employing an ISS approach, similarly to the radiographic imaging device 1 illustrated in FIG. 18. The example illustrated in FIG. 55 is a radiographic imaging device 1 employing a PSS approach. In the examples illustrated in FIG. 54 and FIG. 55, the radiation detector 10, the control board 110, and the power source section 108 are arranged alongside one another in the lateral direction of the respective drawings.

In the examples illustrated in FIG. 54 and FIG. 55, the protective layer 117 is further provided between the radiation detector 10 and the inner wall of the imaging face 120A of the case 120. In other words, the protective layer 117 is further provided on the imaging face 120A side, this being the side to which the radiation R is incident. The protective layer 117 may, for example, be configured by a moisture-proof film such as an ALPET (registered trademark) sheet in which aluminum is stacked by for example bonding aluminum foil to an insulating sheet (film), or an insulating sheet such as a Parylene (registered trademark) film or polyethylene terephthalate. The protective layer 117 has a moisture-proof function and an anti-static function with respect to the pixel region 35. Accordingly, the protective layer 117 preferably covers at least the entire surface of the pixel region 35 on the side to which the radiation R is incident, and preferably covers the entire surface of the TFT substrate 12 on the side to which the radiation R is incident.

Note that FIG. 54 and FIG. 55 illustrate embodiments in which both the power source section 108 and the control board 110 are provided on one side of the radiation detector 10, specifically on the side of one edge of the rectangular pixel region 35. However, the positions at which the power source section 108 and the control board 110 are provided are not limited to those of the embodiments illustrated in FIG. 54 and FIG. 55. For example, the power source section 108 and the control board 110 may be provided distributed between two opposing edges of the pixel region 35, or may be provided distributed between two adjacent edges of the pixel region 35.

As in the examples illustrated in FIG. 54 and FIG. 55, in cases in which the radiation detector 10, the control board 110, and the power source section 108 are arranged in a direction intersecting the direction in which the TFT substrate 12 and the conversion layer 14 are stacked (a stacking direction P), the thickness of the case 120 may be varied between the locations of the case 120 where the power source section 108 and the control board 110 are respectively provided, and the location of the case 120 where the radiation detector 10 is provided.

As described previously, the power source section 108 and the control board 110 are often each thicker than the radiation detector 10, as in the example illustrated in FIG. 55. In such cases, as in the example illustrated in FIG. 56, the thickness of the location of the case 120 where the radiation detector 10 is provided may be thinner than the thickness of the locations of the case 120 where the power source section 108 and the control board 110 are provided. In cases in which the thickness is varied between the locations of the case 120 where the power source section 108 and the control board 110 are respectively provided and the location of the case 120 where the radiation detector 10 is provided in this manner, since there might be a concern of causing discomfort to the imaging subject who touches a boundary 120B where a step is created at a boundary between these locations, the boundary 120B is preferably provided with a slope.

So doing enables an ultra-thin portable electronic cassette to be configured according to the thickness of the radiation detector 10.

As another example, in such cases, the case 120 may be configured of different materials at the locations of the case 120 where the power source section 108 and the control board 110 are provided and the location of the case 120 where the radiation detector 10 is provided. Moreover, for example, the locations of the case 120 where the power source section 108 and the control board 110 are provided and the location of the case 120 where the radiation detector 10 is provided may be configured separately to each other.

Moreover, as described previously, the case 120 preferably has a low absorption ratio of the radiation R, in particular X-rays, and high rigidity, and is preferably configured from a material that has a sufficiently high elastic modulus. However, as in the example illustrated in FIG. 57, a location 120C of the case 120 corresponding to the imaging face 120A may be configured with a low absorption ratio of the radiation R and high rigidity, and be configured from a material that has a sufficiently high elastic modulus, while other locations of the case 120 are configured from a different material than the location 120C, for example a material having a lower elastic modulus than the location 120C.

Figure 58:
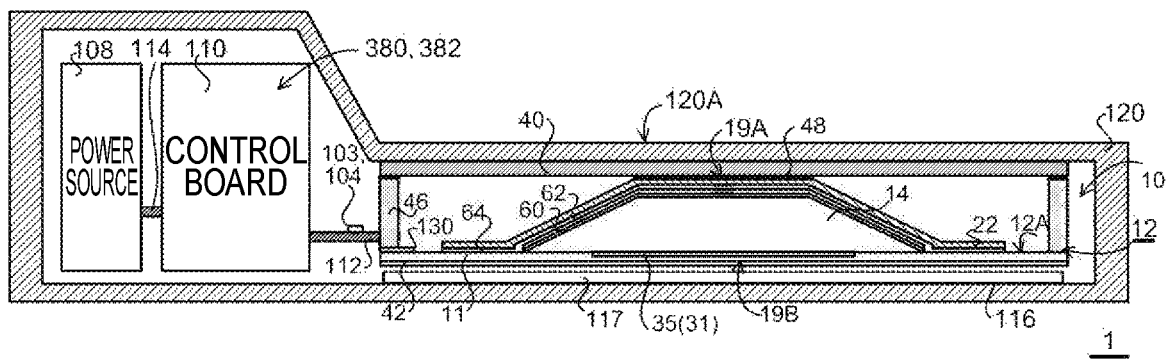
FIG. 58 is a cross-section illustrating an example of configuration of a radiographic imaging device of an exemplary embodiment of technology disclosed herein.

Alternatively, the radiation detector 10 and an inner wall face of the case 120 may contact each other as in the example illustrated in FIG. 58. In such cases, the radiation detector 10 and the inner wall face of the case 120 may be bonded through a bonding layer, or may simply be in contact with each other without providing a bonding layer. Such contact between the radiation detector 10 and the inner wall face of the case 120 further secures the rigidity of the radiation detector 10.

Figure 60:
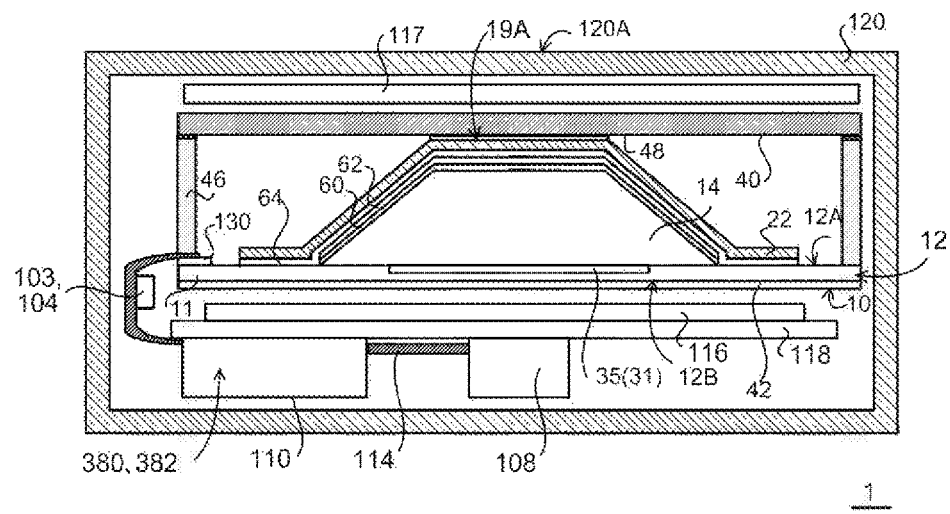
FIG. 60 is a cross-section illustrating an example of configuration of a radiographic imaging device of an exemplary embodiment of technology disclosed herein.

FIG. 59 illustrates an example of a radiographic imaging device 1 employing an ISS approach, similarly to the radiographic imaging device 1 illustrated in FIG. 19. FIG. 60 illustrates an example of a radiographic imaging device 1 employing a PSS approach. In the examples illustrated in FIG. 59 and FIG. 60, the TFT substrate 12 is provided on one side, and the control board 110 and the power source section 108 are provided on the other side of the sheet 116 and the base 118. This configuration enables the size of the radiographic imaging device 1 in plan view to be reduced in comparison to cases in which the radiation detector 10, the control board 110, and the power source section 108 are arranged in the lateral direction in the drawings (see FIG. 54 to FIG. 58).

The disclosures of Japanese Patent Application Nos. 2018-051690, 2018-219696, 2019-022148, 2018-119356, 2018-219699, and 2019-022126 are incorporated in their entirety by reference herein.

All cited documents, patent applications, and technical standards mentioned in the present specification are incorporated by reference in the present specification to the same extent as if each individual cited document, patent application, or technical standard was specifically and individually indicated to be incorporated by reference.

What is claimed is:
1. A radiation detector comprising:
  a stacked body configured by stacking:
    a substrate comprising a base member and a plurality of pixels, the base member formed of a resin, having a flexibility, and including, at a first surface, a fine particle layer containing inorganic fine particles having a mean particle size of from 0.05 μm to 2.5 μm, the plurality of pixels accumulate electrical charges generated in response to light converted from radiation in a pixel region, the plurality of pixels formed at a second surface, which is an opposite-side surface of the first surface of the base member; and
    a conversion layer provided at the second surface of the base member provided with the pixel region and configured to convert the radiation into light; and
  a reinforcement substrate provided to at least one out of a surface on a side of the substrate of the stacked body, or a surface on a side of the conversion layer of the stacked body.

2. The radiation detector of claim 1, wherein the base member has a coefficient of thermal expansion no greater than 20 ppm/K at 300° C. to 400° C.

3. The radiation detector of claim 1, wherein the base member having at least one characteristic out of:
   a heat shrinkage ratio in a machine direction at 400° C. and at a thickness of 25 μm of no greater than 0.5%; or
   a modulus of elasticity at 500° C. of no less than 1 GPa.

4. The radiation detector of claim 1, wherein the inorganic fine particles include an element having an atomic number that is greater than an atomic number of elements configuring the base member and that is an atomic number not exceeding 30.

5. The radiation detector of claim 1, wherein the reinforcement substrate has a bending elastic modulus of from 150 MPa to 2500 MPa.

6. The radiation detector of claim 1, wherein a ratio of a coefficient of thermal expansion of the reinforcement substrate with a respect to a coefficient of thermal expansion of the conversion layer is from 0.5 to 2.

7. The radiation detector of claim 1, wherein the reinforcement substrate has a coefficient of thermal expansion of from 30 ppm/K to 80 ppm/K.

8. The radiation detector of claim 1, wherein the reinforcement substrate contains a material having a yield point.

9. The radiation detector of claim 1, wherein the reinforcement substrate has a higher rigidity than the base member.

10. The radiation detector of claim 1, wherein a thickness of the reinforcement substrate is thicker than a thickness of the base member.

11. The radiation detector of claim 1, wherein:
    the conversion layer covers the pixel region and is provided in a region corresponding to a part of the second surface of the base member provided with the pixel region; and
    the reinforcement substrate is provided in a wider region than the pixel region, where the conversion layer is provided.

12. The radiation detector of claim 1, wherein:
    the reinforcement substrate is provided at the surface on the side of the substrate of the stacked body, and at the surface on the side of the conversion layer of the stacked body; and
    a thickness of the reinforcement substrate provided at the surface on the side of the conversion layer of the stacked body is thicker than a thickness of the reinforcement substrate provided at the surface on the side of the substrate of the stacked body.

13. The radiation detector of claim 1, further comprising:
    a buffer layer provided between the substrate and the conversion layer, the buffer layer buffers a difference between a coefficient of thermal expansion of the conversion layer and a coefficient of thermal expansion of the substrate.

14. The radiation detector of claim 1, wherein:
    the reinforcement substrate is provided at the surface on the side of the substrate of the stacked body and at the surface on the side of the conversion layer of the stacked body, and
    the radiation detector further comprises a sealing member provided between the reinforcement substrate and the second surface of the base member so as to seal a side face of the conversion layer.

15. The radiation detector of claim 1, further comprising:
    a reflective adhesion layer for reflecting light produced by the conversion layer;
    a bonding layer covering a region including a region spanning from an end portion of the reflective adhesion layer to a front surface of the substrate; and
    a protective layer covering the reflective adhesion layer and the bonding layer,
    wherein the stacked body further includes a location at the surface on the side of the conversion layer of the stacked body, where the reflective adhesion layer, the bonding layer, and the protective layer are stacked in this sequence, and
    the reinforcement substrate is provided to at least one out of the surface on the side of the substrate of the stacked body or a surface on a side of the protective layer of the stacked body.

16. The radiation detector of claim 1, further comprising:
    a reflective adhesion layer for reflecting light produced by the conversion layer, and covering a region including the conversion layer and spanning a front surface of the substrate; and
    a protective layer covering the reflective adhesion layer,
    wherein the stacked body further includes a location at the surface on the side of the conversion layer of the stacked body, where the reflective adhesion layer and the protective layer are stacked in this sequence, and
    the reinforcement substrate is provided to at least one out of the surface on the side of the substrate of the stacked body or a surface on a side of the protective layer of the stacked body.

17. The radiation detector of claim 1, wherein the conversion layer includes columnar crystals of CsI.

18. A radiographic imaging device comprising:
    a radiation detector of claim 1;
    a controller that outputs a control signal for reading the electrical charges accumulated in the plurality of pixels;
    a driver that reads the electrical charges from the plurality of pixels in response to the control signal; and
    a signal processor that is input with an electrical signal according to the electrical charges read from the plurality of pixels, and the signal processor generates image data according to the input electrical signal and outputs the image data to the controller.

19. The radiographic imaging device of claim 18, further comprising: a case that includes an irradiated face for an irradiation with radiation, and the case houses the radiation detector in a state in which out of the substrate and the conversion layer of the radiation detector, it is the substrate that opposes the irradiated face.

20. A manufacturing method for a radiation detector, the manufacturing method comprising:
    a process of coating an adhesion layer onto a reinforcement substrate having a size according to a size of a radiation detector;
    a process of forming a substrate on a support body with a separation layer interposed between the support body and the substrate, the substrate being provided with a base member that is flexible and made of a resin, and the base member is provided with, at a first surface of the base member, a fine particle layer including inorganic fine particles having a mean particle size of from 0.05 μm to 2.5 μm, and the substrate is provided with a plurality of pixels configured to accumulate electrical charges generated in response to light converted from radiation in a pixel region at a second surface, which is an opposite-side surface of the first surface of the base member;

a process of forming a conversion layer configured to convert the radiation into light at the second surface of the base member provided with the pixel region;
a process of connecting wiring to the substrate in order to connect the plurality of pixels to a circuit section;
a process of affixing the reinforcement substrate to an opposite-side surface of the conversion layer to a surface opposing the substrate; and
a process of separating the substrate provided with the conversion layer and the reinforcement substrate, and to which the wiring is connected from the support body.

* * * * *